United States Patent
Yu et al.

(10) Patent No.: US 10,772,958 B2
(45) Date of Patent: *Sep. 15, 2020

(54) HUMANIZED ANTI-CD40 ANTIBODIES AND METHODS OF ADMINISTERING THEREOF

(71) Applicant: Primatope Therapeutics Inc., Newton, MA (US)

(72) Inventors: Bo Yu, Newton, MA (US); Rijian Wang, Newton, MA (US); Keith Reimann, Newton, MA (US)

(73) Assignee: Primatope Therapeutics Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/234,110

(22) Filed: Dec. 27, 2018

(65) Prior Publication Data

US 2019/0117771 A1 Apr. 25, 2019

Related U.S. Application Data

(60) Continuation of application No. 15/955,393, filed on Apr. 17, 2018, now Pat. No. 10,201,608, which is a division of application No. 15/829,352, filed on Dec. 1, 2017, now Pat. No. 9,974,855, which is a continuation of application No. PCT/US2016/050114, filed on Sep. 2, 2016.

(60) Provisional application No. 62/214,411, filed on Sep. 4, 2015.

(51) Int. Cl.
*A61K 39/395* (2006.01)
*C07K 16/28* (2006.01)
*A61K 45/06* (2006.01)
*A61K 31/436* (2006.01)
*C07K 16/18* (2006.01)
*A61K 38/00* (2006.01)
*A61K 39/00* (2006.01)

(52) U.S. Cl.
CPC ...... *A61K 39/39558* (2013.01); *A61K 31/436* (2013.01); *A61K 39/395* (2013.01); *A61K 39/3955* (2013.01); *A61K 45/06* (2013.01); *C07K 16/18* (2013.01); *C07K 16/2866* (2013.01); *C07K 16/2878* (2013.01); *A61K 38/00* (2013.01); *A61K 2039/505* (2013.01); *C07K 2317/24* (2013.01); *C07K 2317/33* (2013.01); *C07K 2317/76* (2013.01); *C07K 2317/92* (2013.01); *C07K 2317/94* (2013.01); *Y02A 50/414* (2018.01); *Y02A 50/423* (2018.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,677,165 A | 10/1997 | de Boer et al. |
| 5,693,761 A | 12/1997 | Queen et al. |
| 5,693,762 A | 12/1997 | Queen et al. |
| 5,801,227 A | 9/1998 | Fanslow, III et al. |
| 5,874,082 A | 2/1999 | de Boer |
| 6,004,552 A | 12/1999 | de Boer et al. |
| 6,051,228 A | 4/2000 | Aruffo et al. |
| 6,054,297 A | 4/2000 | Carter et al. |
| 6,056,959 A | 5/2000 | de Boer et al. |
| 6,132,978 A | 10/2000 | Gelfand et al. |
| 6,280,957 B1 | 8/2001 | Sayegh et al. |
| 6,312,693 B1 | 11/2001 | Aruffo et al. |
| 6,315,998 B1 | 11/2001 | de Boer et al. |
| 6,413,514 B1 | 7/2002 | Aruffo et al. |
| 6,632,927 B2 | 10/2003 | Adair et al. |
| 7,063,845 B2 | 6/2006 | Mikayama et al. |
| 7,193,064 B2 | 3/2007 | Mikayama et al. |
| 7,288,251 B2 | 10/2007 | Bedian et al. |
| 7,361,345 B2 | 4/2008 | de Boer et al. |
| 7,445,780 B2 | 11/2008 | Chu et al. |
| 7,498,032 B2 | 3/2009 | Siegall et al. |
| 7,537,763 B2 | 5/2009 | Mikayama et al. |
| 7,790,166 B2 | 9/2010 | de Boer et al. |
| 8,106,164 B2 | 1/2012 | Gellerfors et al. |
| 8,138,134 B2 | 3/2012 | Zhang et al. |
| 8,226,952 B2 | 7/2012 | Thomas, Jr. et al. |
| 8,277,810 B2 | 10/2012 | Long et al. |
| 8,303,955 B2 | 11/2012 | Presta et al. |

(Continued)

FOREIGN PATENT DOCUMENTS

| | | |
|---|---|---|
| EP | 1707627 A1 | 10/2006 |
| EP | 1682180 B1 | 11/2009 |

(Continued)

OTHER PUBLICATIONS

D'Angelo et al., Many Routes to an Antibody Heavy-Chain CDR3: Necessary, Yet Insufficient, for Specific Binding (Frontiers in Immunology vol. 9, Article 395 Mar. 2018; doi:10.3389/fimmu.2018. 00395). (Year: 2018).*

(Continued)

*Primary Examiner* — Phillip Gambel

(74) *Attorney, Agent, or Firm* — Clark & Elbing LLP

(57) ABSTRACT

The present disclosure relates to anti-CD40 antibodies, such as humanized anti-CD40 antibodies, that may be used in various therapeutic, prophylactic and diagnostic methods. The antibodies generally block the ability of CD40 to bind CD154 and do so without activating the cell expressing CD40 (e.g., a B cell). The present antibodies or fragments thereof may be used to reduce complications associated with organ or tissue transplantation.

26 Claims, 26 Drawing Sheets

Specification includes a Sequence Listing.

(56) References Cited

U.S. PATENT DOCUMENTS

| | | | |
|---|---|---|---|
| 8,435,514 B2 | 5/2013 | Perrin et al. | |
| 8,591,900 B2 | 11/2013 | Barrett et al. | |
| 8,784,823 B2 | 7/2014 | Burkly et al. | |
| 8,828,396 B2 | 9/2014 | Heusser et al. | |
| 8,911,726 B2 | 12/2014 | Takahashi et al. | |
| 9,023,360 B2 | 5/2015 | Takahashi et al. | |
| 9,023,361 B2 | 5/2015 | Takahashi et al. | |
| 9,125,893 B2 | 9/2015 | Endo et al. | |
| 9,475,879 B2 | 10/2016 | Suri et al. | |
| 9,598,494 B2 | 3/2017 | Takahashi et al. | |
| 9,974,855 B2 | 5/2018 | Yu et al. | |
| 9,987,356 B2 * | 6/2018 | Reimann | C07K 16/18 |
| 2002/0031512 A1 | 3/2002 | Pasch et al. | |
| 2003/0211100 A1 | 11/2003 | Bedian et al. | |
| 2004/0110226 A1 | 6/2004 | Lazar et al. | |
| 2004/0120948 A1 | 6/2004 | Mikayama et al. | |
| 2005/0118166 A1 | 6/2005 | Yellin et al. | |
| 2007/0110754 A1 | 5/2007 | Long et al. | |
| 2007/0190051 A1 | 8/2007 | Bedian et al. | |
| 2007/0218060 A1 | 9/2007 | Long et al. | |
| 2008/0085531 A1 | 4/2008 | Den Hartog et al. | |
| 2009/0123466 A1 | 5/2009 | Mikayama et al. | |
| 2009/0304706 A1 | 12/2009 | Lu et al. | |
| 2009/0311268 A1 | 12/2009 | Thomas et al. | |
| 2010/0098694 A1 | 4/2010 | Bedian et al. | |
| 2010/0234578 A1 | 9/2010 | Mikayama et al. | |
| 2010/0239575 A1 | 9/2010 | Banchereau et al. | |
| 2011/0027276 A1 | 2/2011 | Bernett et al. | |
| 2011/0243932 A1 | 10/2011 | Barrett et al. | |
| 2012/0121585 A1 | 5/2012 | Heusser et al. | |
| 2013/0323267 A1 | 12/2013 | Endo et al. | |
| 2014/0093497 A1 | 4/2014 | Reimann et al. | |
| 2018/0344845 A1 | 12/2018 | Reimann et al. | |

FOREIGN PATENT DOCUMENTS

| | | |
|---|---|---|
| EP | 1297017 B1 | 6/2012 |
| EP | 1945260 B1 | 10/2012 |
| JP | 2005-508176 A | 3/2005 |
| WO | WO-01/98357 A2 | 12/2001 |
| WO | WO-03/040170 A2 | 5/2003 |
| WO | WO-2005/044307 A2 | 5/2005 |
| WO | WO-2005/044854 A2 | 5/2005 |
| WO | WO-2007/053661 A2 | 5/2007 |
| WO | WO-2007/053767 A1 | 5/2007 |
| WO | WO-2007/075326 A2 | 7/2007 |
| WO | WO-2008/118356 A2 | 10/2008 |
| WO | WO-2009/062054 A1 | 5/2009 |
| WO | WO-2010/065819 A1 | 6/2010 |
| WO | WO-2012/065950 A1 | 5/2012 |
| WO | WO-2012/111762 A1 | 8/2012 |
| WO | WO-2012/125569 A2 | 9/2012 |
| WO | WO-2014/121099 A1 | 8/2014 |
| WO | WO-2016/119909 A1 | 8/2016 |
| WO | WO-2016/126702 A1 | 8/2016 |
| WO | WO-2017/004006 A1 | 1/2017 |

OTHER PUBLICATIONS

Piche-Nicholas et al., Changes in complemetarity-determining regions significantly alter IgG binding to the neonatal Fc receptor (FcRN) and pharmacokinetics (MABS 2018, vol. 10, No. 1, 81-94, doi.org/10.1080/19420862.2017.1389355). (Year: 2018).*

Vonderheide et al., Clin Cancer Res 19: 1035-1043 (2013). (Year: 2013).*

Malmborg Hager et al., "Affinity and epitope profiling of mouse anti-CD40 monoclonal antibodies," Scand J Immunol. 57(6):517-24 (2003).

Kasran et al., "Safety and tolerability of antagonist anti-human CD40 Mab ch5D12 in patients with moderate to severe Crohn's disease," Aliment Pharmacol Ther. 22(2):111-22 (2005).

Adams et al., "Development of a chimeric anti-CD40 monoclonal antibody that synergizes with LEA29Y to prolong islet allograft survival," J Immunol. 174(1):542-50 (2005).

Albach et al., "Safety, pharmacokinetics, and pharmacodynamics of single rising doses of BI 655064, an antagonistic anti-CD40 antibody in healthy subjects: a potential novel treatment for autoimmune disease," Eur J Clin Pharmacol. 74(2):161-169 (2018).

Almagro et al., "Humanization of antibodies," Front Biosci. 13:1619-33 (2008).

Aoyagi et al., "A human anti-CD40 monoclonal antibody, 4D11, for kidney transplantation in cynomolgus monkeys: induction and maintenance therapy," Am J Transplant. 9(8):1732-41 (2009).

Apexigen APX005M Briefing Materials, Oncologic Drugs Advisory Committee, Jun. 21, 2017 (22 pages).

Badell et al., "Nondepleting anti-CD40-based therapy prolongs allograft survival in nonhuman primates," Am J Transplant. 12(1):126-35 (2012).

Bankert et al., "Induction of an altered CD40 signaling complex by an antagonistic human monoclonal antibody to CD40," J Immunol. 194(9):4319-27 (2015).

Boon et al., "Preclinical assessment of anti-CD40 Mab 5D12 in cynomolgus monkeys," Toxicology. 174(1):53-65 (2002).

Boon et al., "Prevention of experimental autoimmune encephalomyelitis in the common marmoset (Callithrix jacchus) using a chimeric antagonist monoclonal antibody against human CD40 is associated with altered B cell responses," J Immunol. 167(5):2942-9 (2001).

Carpenter et al., "Activation of human B cells by the agonist CD40 antibody CP-870,893 and augmentation with simultaneous toll-like receptor 9 stimulation," J Transl Med. 7:93 (2009) (10 pages).

Carter et al., "Humanization of an anti-p185HER2 antibody for human cancer therapy," Proc Natl Acad Sci U.S.A. 89(10):4285-9 (1992).

Chamberlain, "Repeated administration of dapirolizumab pegol in a randomised phase I study is well tolerated and accompanied by improvements in several composite measures of systemic lupus erythematosus disease activity and changes in whole blood transcriptomic profiles," Ann Rheum Dis. 76(11):1837-44 (2017).

Chen et al., "Enhancement and destruction of antibody function by somatic mutation: unequal occurrence is controlled by V gene combinatorial associations," EMBO J. 14(12):2784-94 (1995).

Colman, "Effects of amino acid sequence changes on antibody-antigen interactions," Res Immunol. 145(1):33-6 (1994).

Cooper et al., "Platelet-associated antibodies, cellular immunity and FCGR3a genotype influence the response to rituximab in immune thrombocytopenia," Br J Haematol. 158(4):539-47 (2012).

Cordoba et al., "A novel, blocking, Fc-silent anti-CD40 monoclonal antibody prolongs nonhuman primate renal allograft survival in the absence of B cell depletion," Am J Transplant. 15(11):2825-36 (2015).

Daniluk et al., "SAT0147 Safety and Efficacy of BI 655064, An Antagonistic Anti-CD40 Antibody in Rheumatoid Arthritis (RA) Patients," Ann Rheum Dis. 75(2):718 (2016) (3 pages).

De Boer et al., "Generation of monoclonal antibodies to human lymphocyte cell surface antigens using insect cells expressing recombinant proteins," J Immunol Methods. 152(1):15-23 (1992).

Denton et al., "Central role for CD40/CD40 ligand (CD154) interactions in transplant rejection," Pediatr Transplant. 2(1):6-15 (1998). Abstract Only. Retrieved from <http://www.ncbi.nlm.nih.gov/pubmed/10084754> on Nov. 18, 2013.

Wu et al., "Simultaneous Humanization and Affinity Optimization of Monoclonal Antibodies," Antibody-Drug Conjugates in: Methods in Molecular Biology, ISSN 1064-3745; vol. 1045; [Methods in Molecular Biology, ISSN 1064-3745; vol. 1045], Humana Press, US, vol. 207, Jan. 1, 2003 (Jan. 1, 2003), pp. 197-212, XP009052628, ISBN: 978-1-62703-541-5.

European Search Report dated Apr. 26, 2018, corresponding to European Patent Application No. 16843066.8; (11 pages).

Gershoni et al., "Epitope mapping—the first step in developing epitope-based vaccines," BioDrugs. 21(3):145-56 (2007).

Gilson et al., "Anti-CD40 monoclonal antibody synergizes with CTLA4-Ig in promoting long-term graft survival in murine models of transplantation," J Immunol. 183(3):1625-35 (2009).

(56) References Cited

OTHER PUBLICATIONS

Grammer et al., "Abnormal germinal center reactions in systemic lupus erythematosus demonstrated by blockade of CD154-CD40 interactions," J Clin Invest. 112(10):1506-20 (2003).
Haanstra et al., "Prevention of kidney allograft rejection using anti-CD40 and anti-CD86 in primates." Transplantation. 75(5):637-43 (2003).
International Search Report and Written Opinion for International Applicaiton No. PCT/US2016/50114, dated Jan. 19, 2017 (14 pages).
Kettleborough et al., "Humanization of a mouse monoclonal antibody by CDR-grafting: the importance of framework residues on loop conformation," Protein Eng. 4(7):773-83 (1991).
Kim et al., "Costimulation blockade alters germinal center responses and prevents antibody-mediated rejection," Am J Transplant. 14(1):59-69 (2014).
Kim et al., "Fc-Silent Anti-CD154 Domain Antibody Effectively Prevents Nonhuman Primate Renal Allograft Rejection," Am J Transplant. 17:1182-92 (2017).
Kussie et al., "A single engineered amino acid substitution changes antibody fine specificity," J Immunol. 152(1):146-52 (1994).
Kuwana et al., "Effect of a single injection of humanized anti-CD154 monoclonal antibody on the platelet-specific autoimmune response in patients with immune thrombocytopenic purpura," Blood 103(4):1229-36 (2004).
Lazar et al., "A Molecular Immunology Approach to Antibody Humanization and Functional Optimization," Molecular Immunol, Pergamon, GB, vol. 44, No. 8, Dec. 1, 2006 (Dec. 1, 2006), pp. 1986-1998, XP005792736, ISSN: 0161-5890, DOI: 10.1016/J.MOLIMM.2006.09.029.
Lee et al.,"In vitro testing of an anti-CD40 monoclonal antibody, clone 2C10, in primates and pigs." Transpl Immunol. 33(3):185-191 (2015).
Liu et al., "Agonistic antibody to CD40 boosts the antitumor activity of adoptively transferred T cells in vivo," 35(3):276-82 (2012).
Lowe et al., "A novel monoclonal antibody to CD40 prolongs islet allograft survival," Am J Transplant. 12(8):2079-87 (2012).
Luqman et al., "The antileukemia activity of a human anti-CD40 antagonist antibody, HCD122, on human chronic lymphocytic leukemia cells," Blood. 112(3):711-20 (2008).
Mohiuddin et al., "Chimeric 2C10R4 anti-CD40 antibody therapy is critical for long-term survival of GTKO.hCD46.hTBM pig-to-primate cardiac xenograft." Nat Commun. 7(5): (2016) (10 pages).
Mohiuddin et al., "Role of anti-CD40 antibody-mediated costimulation blockade on non-Gal antibody production and heterotopic cardiac xenograft survival in a GTKO.hCD46Tg pig-to-baboon model." Xenotransplantation. 21(1): 35-45 (2013).
Molano et al., "Prolonged islet allograft survival in diabetic NOD mice by targeting CD45RB and CD154," Diabetes. 52(4):957-64 (2003).
Morris, Epitope mapping of protein antigens by competition ELISA. The Protein Protocols Handbook. Humana Press, 595-600 (1996).
Najafian et al., "CTLA4-Ig: a novel immunosuppressive agent," Expert Opin Investig Drugs. 9(9):2147-57 (2000).
O'Neill et al,. "Comparative Evaluation of alphaCD40 (2C10R4) and alphaCD154 (5C8H1 and IDEC-131) in a Nonhuman Primate Cardiac Allotransplant Model," Transplantation 101(9):2038-47 (2017).

Okimura et al., "Characterization of ASKP1240, a fully human antibody targeting human CD40 with potent immunosuppressive effects," Am J Transplant. 14:1290-99 (2014).
Oura et al., "Long-term hepatic allograft acceptance based on CD40 blockade by ASKP1240 in nonhuman primates," Am J Transplant. 12(7):1740-54 (2012).
Pearson et al., "Anti-CD40 therapy extends renal allograft survival in rhesus macaques," Transplantation. 74(7):933-40 (2002).
Queen et al.,"A humanized antibody that binds to the interleukin 2 receptor," Proc Natl Acad Sci U.S.A. 86(24):10029-33 (1989).
Roguska et al., "Humanization of murine monoclonal antibodies through variable domain resurfacing," Proc Natl Acad Sci U.S.A. 91(3):969-73 (1994).
Rudikoff et al., "Single amino acid substitution altering antigen-binding specificity," Proc Natl Acad Sci U S A. 79(6):1979-83 (1982).
Russo et al., "Platelet-activating factor mediates CD40-dependent angiogenesis and endothelial-smooth muscle cell interaction," J Immunol. 171(10):5489-97 (2003).
Schwabe et al., "FRI0168 Safety, Tolerability, Pharmacokinetics (PK) and Pharmacodynamics (PD) of BI 655064, An Antagonistic Anti-CD40 Antibody in Healthy Volunteers," Ann Rheum Dis. 74(2):484 (2015) (3 pages).
Sho et al., "Requirements for induction and maintenance of peripheral tolerance in stringent allograft models," Proc Natl Acad Sci USA. 102(37):13230-5 (2005).
Shock et al., "CDP7657, an anti-CD40L antibody lacking an Fc domain, inhibits CD40L-dependent immune responses without thrombotic complications: an in vivo study," Arthritis Res Ther 17(234):1-12 (2015).
Slade et al., "Assessment of Safety, Pharmacokinetics and Pharmacodynamics of a Novel Anti-CD40 Monoclonal Antibody, CFZ533, in Healthy Volunteers and in Rheumatoid Arthritis Patients," 2016 ACR/ARHP Annual Meeting, Sep. 2016, Abstract No. 1582 (2 pages).
Strohl, "Optimization of Fc-mediated effector functions of monoclonal antibodies," Curr Opin Biotechnol. 20(6):685-91 (2009).
Sutherland et al., "Anti-CD45RB antibody deters xenograft rejection by modulating T cell priming and homing," Int Immunol. 14(8):953-62 (2002).
Thompson et al., "CD40-specific costimulation blockade enhances neonatal porcine islet survival in nonhuman primates," Am J Transplant. 11(5):947-57 (2011).
Visvanathan et al., "FRI0231 Treatment with BI 655064 (Antagonistic Anti-CD40 Antibody) Modulates Biomarkers Associated with Rheumatoid Arthritis (RA)," Ann Rhem Dis. 75(2):517 (2016) (3 pages).
Visvanathan et al., "Treatment with BI 655064 (Antagonistic Anti-CD40 Antibody) Modulates Clinical and Biomarker Parameters Associated with Rheumatoid Arthritis (RA)," Scientific Abstracts, p. 517 Jun. 10, 2016.
Winter et al., "Humanized antibodies," Trends Pharmacol Sci. 14(5):139-43 (1993).
Yamniuk et al., "Functional Antagonism of Human CD40 Achieved by Targeting a Unique Species-Specific Epitope," J Mol Biol. 428(14):2860-79 (2016).

\* cited by examiner

Description: Mouse anti-CD40 clone 2C10
Heavy chain (signal peptide + V-region)
DNA
ATGGAAAGGCACTGGATCTTTCTCTTCCTGTTGTCAGTAACTGCAGGTGTCCAC
TCCCAGGTCCAGCTGCAACAGTCTGGGGCTGAACTGGCAAAACCTGGGGCCT
CAGTGAAGATGTCCTGTAAGGCTTCTGGCTACACCTTTACTAACTACTGGATGC
ACTGGGTAAAACAGAGGCCTGGACAGGGTCTGGAATGGATTGGATACATTAAT
CCTAGCAATGATTATACTAAGTACAATCAAAAGTTCAAGGACAAGGCCACATTG
ACTGCAGACAAATCCTCCAACACAGCCTACATGCAACTGGGTAGCCTGACATCT
GAGGACTCTGCAGTCTATTATTGTGCAAGACAGGGGTTTCCTTACTGGGGCCA
AGGGACTCTGGTCACTGTCTCT
Protein
MERHWIFLFLLSVTAGVHSQVQLQQSGAELAKPGASVKMSCKASGYTFTNYW
MHWVKQRPGQGLEWIGYINPSNDYTKYNQKFKDKATLTADKSSNTAYMQLGSL
TSEDSAVYYCARQGFPYWGQGTLVTVS Light chain (signal peptide + V-region)
DNA
ATGGATTTTCAAGTGCAGATTTTCAGCTTCCTGCTAATCAGTGCCTCAGTCATAA
TATCCAGAGGACAAATTGTTCTCACCCAGTCTCCAGCAATCATGTCTGCATCTCC
AGGGGAGAAGGTCACCATGACCTGCAGTGCCAGCTCAAGTGTAAGTTACATGC
ACTGGTACCACCAGAGGTCAGGCACCTCCCCCAAAAGATGGATTTATGACACA
TCCAAACTGGCTTCTGGAGTCCCTGCTCGCTTCAGTGGCAGTGGGTCTGGGAC
CTCTTACTCTCTCACAATCAGCAGCATGGAGGCTGAAGATGCTGCCACTTATTAC
TGCCACCAGTTGAGTAGTGACCCATTCACGTTCGGCTCGGGGACAAAGTTGGA
AATAAAA
Protein
MDFQVQIFSFLLISASVIISRGQIVLTQSPAIMSASPGEKVTMTCSASSSVSYMHW
YHQRSGTSPKRWIYDTSKLASGVPARFSGSGSGTSYSLTISSMEAEDAATYYCHQL
SSDPFTFGSGTKLEIK

FIG. 1

```
2C10_VH   QVQLQQSGAELAKPGASVKMSCKASG YTFTNYWMH WVKQRPGQGLEWIG YINPSNDYTKYNQKFKD
VH1-3     QVQLVQSGAEVKKPGASVKVSCKASG YTFTSYAMH WVRQRPGQRLEWMG WINAGNGNTKYSQKFQG
2C10_h1   QVQLVQSGAEVKKPGASVKVSCKASG YTFTNYWMH WVRQAPGQRLEWMG YINPSNDYTKYNQKFKD
2C10_h2   QVQLVQSGAEVKKPGASVKVSCKASG YTFTNYWMH WVRQAPGQRLEWMG YINPSNDYTKYNQKFKD
2C10_h3   QVQLVQSGAEVKKPGASVKVSCKASG YTFTNYWMH WVRQAPGQRLEWIG YINPSNDYTKYNQKFKD

2C10_VH   KATLTADKSSNTAYMQLGSLTSEDSAVYYCAR QGFPY WGQGTLVTVSA
VH-3      RVTITRDTSASTAYMELSSLRSEDTAVYYCAR ----- WGQGTLVTVSS
2C10_h1   RVTITRDTSASTAYMELSSLRSEDTAVYYCAR QGFPY WGQGTLVTVSS
2C10_h2   RVTITADKSASTAYMELSSLRSEDTAVYYCAR QGFPY WGQGTLVTVSS
2C10_h3   RATLTADKSANTAYMELSSLRSEDTAVYYCAR QGFPY WGQGTLVTVSS
```

FIG. 13A

```
2C10_VL   QIVLTQSPAIMSASPGEKVTMTC SASSSVS-YMH WYHQRSGTSPKRWIY DTSKLAS
VKW_11    EIVLTQSPATLSLSPGERATLSC RASQSVSSYLA WYQQKPGQAPRLLIY DASNRAT
2C10_11   EIVLTQSPATLSLSPGERATLSC SASSSVS-YMH WYQQKPGQAPRLLIY DTSKLAS
2C10_12   EIVLTQSPATLSLSPGERATLSC SASSSVS-YMH WYQQKPGQAPRRWIY DTSKLAS

2C10_VL   GVPARFSGSGSGTSYSLTISSMEAEDAATYYC HQLSSDPFT FGSGTKLEIK
VK3-11    GIPARFSGSGSGTDFTLTISSLEAEDFAVYYC --------- FGGGTKVEIK
2C10-11   GIPARFSGSGSGTDFTLTISSLEPEDFAVYYC HQLSSDPFT FGGGTKVEIK
2C10-12   GVPARFSGSGSGTDYTLTISSLEPEDFAVYYC HQLSSDPFT FGGGTKVEIK
```

FIG. 13B

```
2C10HP:   [CDR2] R--L---K-A-------------------- [CDR3]
2C10HB1:  [CDR2] R--L---T-T-------------------- [CDR3]
2C10HB2:  [CDR2] K--I---E-T-------------------- [CDR3]
```

FIG. 14

2C10HP:
QVQLVQSGAEVKKPGASVKVSCKASGYTFTNYWMHWVRQAPGQRLEWIGYIN
PSNDYTKYNQKFKDRATLTADKSANTAYMELSSLRSEDTAVYYCARQGFPYWGQGTL
VTVSS

2C10HB1:
QVQLVQSGAEVKKPGASVKVSCKASGYTFTNYWMHWVRQAPGQRLEWIGYIN
PSNDYTKYNQKFKDRATLTADISTNTAYMELSSLRSEDTAVYYCARQGFPYWGQGTL
VTVSS

2C10HB2:
QVQLVQSGAEVKKPGSSVKVSCKASGYTFTNYWMHWVRQAPGQGLEWIGYIN
PSNDYTKYNQKFKDKATITADESTNTAYMELSSLRSEDTAVYYCARQGFPYWGQGTLV
TVSS

2C10KP:
EIVLTQSPATLSLSPGERATLSCSASSSVSYMHWYQQKPGQAPRRWIYDTSKLAS
GVPARFSGSGSGTDYTLTISSLEPEDFAVYYCHQLSSDPFTFGGGTKVEIK

2C10KB1:
DIQMTQSPSTLSASVGDRVTITCSASSSVSYMHWYQQKPGKAPKLLIYDTSKLAS
GVPARFSGSGSGTEFTLTISSLQPDDFATYYCHQLSSDPFTFGQGTKVEVK

2C10KB2:
EIVLTQSPATLSLSPGERATLSCSASSSVSYMHWYQQKPGQAPRLLIYDTSKLASG
IPARFSGSGSGTDFTLTISSLEPEDFAVYYCHQLSSDPFTFGQGTKLEIK

FIG. 15

Heavy chain sequence

```
  1  atggactgga cctggaggat tctcttttg gtggcagcag ccacaggtgc
      M  D  W   T  W  R   I  L  F  L  V  A  A   A  T  G 51  ccactcccaa gtgcagcttg tccagtccgg agccgaggtg aaaaagcccg
      A  H  S  Q   V  Q  L   V  Q  S   G  A  E  V   K  K  P 101  gtgcctcagt aaaggtctcc tgcaaggcct ctggctatac tttcaccaat
      G  A  S   V  K  V  S   C  K  A   S  G  Y   T  F  T  N 151  tattggatgc actgggtgag gcaggctccc ggacagcgcc tcgaatggat
      Y  W  M   H  W  V   R  Q  A  P   G  Q  R   L  E  W 201  cggttatatc aacccatcta acgattacac caaatacaat cagaaattca
      I  G  Y  I   N  P  S   N  D  Y   T  K  Y  N   Q  K  F 251  aggaccgggc cacactgaca gctgataaaa gcgctaacac agcttacatg
      K  D  R   A  T  L  T   A  D  K   S  A  N   T  A  Y  M 301  gaacttagct ctctgcgaag cgaggatacc gctgtatact actgcgcaag
      E  L  S   S  L  R   S  E  D  T   A  V  Y  Y   C  A 351  gcagggcttt ccttactggg ggcagggcac tctcgttact gtgagtagtg
      R  Q  G  F   P  Y  W   G  Q  G   T  L  V  T   V  S  S 401  ctagcaccaa gggcccatcg gtcttccccc tggcgcctg ctccaggagc
      A  S  T   K  G  P  S   V  F  P   L  A  P   C  S  R  S 451  acctccgaga gcacagccgc cctgggctgc ctggtcaagg actacttccc
      T  S  E   S  T  A   A  L  G  C   L  V  K   D  Y  F 501  cgaaccggtg acggtgtcgt ggaactcagg cgccctgacc agcggcgtgc
      P  E  P  V   T  V  S   W  N  S   G  A  L  T   S  G  V 551  acaccttccc ggctgtccta cagtcctcag gactctactc cctcagcagc
      H  T  F   P  A  V  L   Q  S  S   G  L  Y   S  L  S  S 601  gtggtgaccg tgccctccag cagcttgggc acgaagacct acacctgcaa
      V  V  T  V   P  S   S  S  L  G   T  K  T   Y  T  C
```

FIG. 21a

```
 651  cgtagatcac aagcccagca acaccaaggt ggacaagaga gttgagtcca
       N  V  D  H  K  P  S  N  T  K  V  D  K  R  V  E  S
 701  aatatggtcc cccatgccca ccatgcccag cacctgagtt cctgggggga
       K  Y  G  P  P  C  P  P  C  P  A  P  E  F  L  G  G
 751  ccatcagtct tcctgttccc cccaaaaccc aaggacactc tcatgatctc
       P  S  V  F  L  F  P  P  K  P  K  D  T  L  M  I
 801  ccggacccct gaggtcacgt gcgtggtggt ggacgtgagc caggaagacc
       S  R  T  P  E  V  T  C  V  V  V  D  V  S  Q  E  D
 851  ccgaggtcca gttcaactgg tacgtggatg gcgtggaggt gcataatgcc
       P  E  V  Q  F  N  W  Y  V  D  G  V  E  V  H  N  A
 901  aagacaaagc cgcgggagga gcagttcaac agcacgtacc gtgtggtcag
       K  T  K  P  R  E  E  Q  F  N  S  T  Y  R  V  V
 951  cgtcctcacc gtcctgcacc aggactggct gaacggcaag gagtacaagt
       S  V  L  T  V  L  H  Q  D  W  L  N  G  K  E  Y  K
1001  gcaaggtctc caacaaaggc ctcccgtcct ccatcgagaa aaccatctcc
       C  K  V  S  N  K  G  L  P  S  S  I  E  K  T  I  S
1051  aaagccaaag ggcagccccg agagccacag gtgtacaccc tgcccccatc
       K  A  K  G  Q  P  R  E  P  Q  V  Y  T  L  P  P
1101  ccaggaggag atgaccaaga accaggtcag cctgacctgc ctggtcaaag
       S  Q  E  E  M  T  K  N  Q  V  S  L  T  C  L  V  K
1151  gcttctaccc cagcgacatc gccgtggagt gggagagcaa tgggcagccg
       G  F  Y  P  S  D  I  A  V  E  W  E  S  N  G  Q  P
1201  gagaacaact acaagaccac gcctcccgtg ctggactccg acggctcctt
       E  N  N  Y  K  T  T  P  P  V  L  D  S  D  G  S
1251  cttcctctac agcaggctca ccgtggacaa gagcaggtgg caggagggga
       F  F  L  Y  S  R  L  T  V  D  K  S  R  W  Q  E  G
1301  atgtcttctc atgctccgtg atgcatgagg ctctgcacaa ccactacaca
       N  V  F  S  C  S  V  M  H  E  A  L  H  N  H  Y  T
1351  cagaagagcc tctccctgtc tccgggtaaa tga
       Q  K  S  L  S  L  S  P  G  K
```

FIG. 21a (Cont.)

Light chain sequence

```
  1  atggaagccc cagctcagct tctcttcctc ctgctactct ggctcccaga
      M  E  A   P  A  Q    L  L  F  L   L  L  L    W  L  P
 51  taccaccgga gagattgtgc tgactcagtc accagcaaca ctgagtctct
      D  T  T   G  E  I  V  L  T  Q    S  P  A  T  L  S  L
101  ctcccggcga gcgtgctaca ctgtcctgtt ccgcaagcag ctcagtgtcc
      S  P  G   E  R  A  T   L  S  C   S  A  S    S  S  V  S
151  tacatgcact ggtatcagca aaagcccggc caggccccca gacggtggat
      Y  M  H    W  Y  Q  Q   K  P  G   Q  A  P   R  R  W
201  ctatgacaca tccaagttgg cttccggcgt ccccgcacgg ttttcaggct
      I  Y  D  T   S  K  L   A  S  G  V  P  A  R   F  S  G
251  caggaagcgg tactgattac actttgacca ttagctctct gaacctgag
      S  G  S   G  T  D  Y   T  L  T   I  S  S    L  E  P  E
301  gacttcgcag tatactactg ccaccagctg agttccgatc cttttacctt
      D  F  A   V  Y  Y   C  H  Q  L   S  S  D    P  F  T
351  tggtggtggt actaaggtcg agatcaaacg tacggtggct gcaccatctg
      F  G  G  G   T  K  V   E  I  K   R  T  V  A   A  P  S
401  tcttcatctt cccgccatct gatgagcagt tgaaatctgg aactgcctct
      V  F  I   F  P  P  S   D  E  Q   L  K  S    G  T  A  S
451  gttgtgtgcc tgctgaataa cttctatccc agagaggcca agtacagtg
      V  V  C   L  L  N    N  F  Y  P   R  E  A   K  V  Q
501  gaaggtggat aacgccctcc aatcgggtaa ctcccaggag agtgtcacag
      W  K  V  D   N  A  L   Q  S  G   N  S  Q  E   S  V  T
551  agcaggacag caaggacagc acctacagcc tcagcagcac cctgacgctg
      E  Q  D   S  K  D  S   T  Y  S   L  S  S    T  L  T  L
601  agcaaagcag actacgagaa acacaaagtc tacgcctgcg aagtcaccca
      S  K  A   D  Y  E    K  H  K  V   Y  A  C   E  V  T
651  tcagggcctg agctcgcccg tcacaaagag cttcaacagg ggagagtgtt
      H  Q  G  L   S  S  P   V  T  K   S  F  N  R   G  E  C
701  ag
```

FIG. 21b

SEQUENCE LISTING

```
<160> NUMBER OF SEQ ID NOS: 35

<210> SEQ ID NO 1
<211> LENGTH: 396
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
atggaaaggc actggatctt tctcttcctg ttgtcagtaa ctgcaggtgt ccactcccag     60
gtccagctgc aacagtctgg ggctgaactg gcaaaacctg gggcctcagt gaagatgtcc    120
tgtaaggctt ctggctacac ctttactaac tactggatgc actgggtaaa acagaggcct    180
ggacagggtc tggaatggat tggatacatt aatcctagca atgattatac taagtacaat    240
caaaagttca aggacaaggc cacattgact gcagacaaat cctccaacac agcctacatg    300
caactgggta gcctgacatc tgaggactct gcagtctatt attgtgcaag acaggggttt    360
ccttactggg gccaagggac tctggtcact gtctct                              396

<210> SEQ ID NO 2
<211> LENGTH: 132
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met Glu Arg His Trp Ile Phe Leu Phe Leu Leu Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Tyr Ile Asn Pro Ser Asn Asp Tyr Thr Lys Tyr Asn
65                  70                  75                  80
```

```
Gln Lys Phe Lys Asp Lys Ala Thr Leu Thr Ala Asp Lys Ser Ser Asn
                85                  90                  95

Thr Ala Tyr Met Gln Leu Gly Ser Leu Thr Ser Glu Asp Ser Ala Val
            100                 105                 110

Tyr Tyr Cys Ala Arg Gln Gly Phe Pro Tyr Trp Gly Gln Gly Thr Leu
        115                 120                 125

Val Thr Val Ser
        130

<210> SEQ ID NO 3
<211> LENGTH: 384
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
atggattttc aagtgcagat tttcagcttc ctgctaatca gtgcctcagt cataatatcc      60
agaggacaaa ttgttctcac ccagtctcca gcaatcatgt ctgcatctcc aggggagaag    120
gtcaccatga cctgcagtgc cagctcaagt gtaagttaca tgcactggta ccaccagagg    180
tcaggcacct cccccaaaag atggatttat gacacatcca aactggcttc tggagtccct    240
gctcgcttca gtggcagtgg gtctgggacc tcttactctc tcacaatcag cagcatggag    300
gctgaagatg ctgccactta ttactgccac cagttgagta gtgacccatt cacgttcggc    360
tcggggacaa agttggaaat aaaa                                          384

<210> SEQ ID NO 4
<211> LENGTH: 128
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr His Gln Arg Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Leu
            100                 105                 110

Ser Ser Asp Pro Phe Thr Phe Gly Ser Gly Thr Lys Leu Glu Ile Lys
        115                 120                 125

<210> SEQ ID NO 5
<211> LENGTH: 100
<212> TYPE: PRT
<213> ORGANISM: Artificial Sequence
<220> FEATURE:
<223> OTHER INFORMATION: Description of Artificial Sequence: Synthetic
``` construct

<400> SEQUENCE: 5

```
Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Ser Glu Ser Glu Phe Leu
        35                  40                  45

Asp Thr Trp Asn Arg Glu Thr Arg Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Leu His Cys Met Ser Glu Ser Cys
                85                  90                  95

Glu Ser Cys Val
            100
```

<210> SEQ ID NO 6
<211> LENGTH: 100
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

```
Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val
            100
```

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
ctaacactca ttcctgttga agctcttgac                                      30

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      construct -continued

<400> SEQUENCE: 8
gctgatgctg caccaactgt atcc                                          24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcaacgttg caggtctcgc                                               20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
ctggatctgc tgcccaaact aactcc                                        26

<210> SEQ ID NO 11
<211> LENGTH: 114
<212> TYPE: PRT
<213> ORGANISM: Mus sp.

<400> SEQUENCE: 11

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
                20                  25                  30

Trp Met His Trp Val Lys Gln Arg Pro Gly Gln Gly Leu Glu Trp Ile
            35                  40                  45

Gly Tyr Ile Asn Pro Ser Asn Asp Tyr Thr Tyr Asn Gln Lys Phe
        50                  55                  60

Lys Asp Lys Ala Thr Leu Thr Ala Asp Lys Ser Ser Asn Thr Ala Tyr
65                  70                  75                  80

Met Gln Leu Gly Ser Leu Thr Ser Glu Asp Ser Ala Val Tyr Tyr Cys
                85                  90                  95

Ala Arg Gln Gly Phe Pro Tyr Trp Gly Gln Gly Thr Leu Val Thr Val
                100                 105                 110

Ser Ala

<210> SEQ ID NO 12
<211> LENGTH: 106
<212> TYPE: PRT
<213> ORGANISM: Mus sp.

<400> SEQUENCE: 12

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

His Trp Tyr His Gln Arg Ser Gly Thr Ser Pro Lys Arg Trp Ile Tyr
            35                  40                  45

Asp Thr Ser Lys Leu Ala Ser Gly Val Pro Ala Arg Phe Ser Gly Ser

```
                50                  55                  60
Gly Ser Gly Thr Ser Tyr Ser Leu Thr Ile Ser Ser Met Glu Ala Glu
 65                  70                  75                  80

Asp Ala Ala Thr Tyr Tyr Cys His Gln Leu Ser Ser Asp Pro Phe Thr
                 85                  90                  95

Phe Gly Ser Gly Thr Lys Leu Glu Ile Lys
            100                 105
```

<210> SEQ ID NO 13
<211> LENGTH: 9
<212> TYPE: PRT
<213> ORGANISM: Mus sp.

<400> SEQUENCE: 13

```
Tyr Thr Phe Thr Asn Tyr Trp Met His
 1               5
```

<210> SEQ ID NO 14
<211> LENGTH: 17
<212> TYPE: PRT
<213> ORGANISM: Mus sp.

<400> SEQUENCE: 14

```
Tyr Ile Asn Pro Ser Asn Asp Tyr Thr Lys Tyr Asn Gln Lys Phe Lys
 1               5                  10                  15

Asp
```

<210> SEQ ID NO 15
<211> LENGTH: 5
<212> TYPE: PRT
<213> ORGANISM: Mus sp.

<400> SEQUENCE: 15

```
Gln Gly Phe Pro Tyr
 1               5
```

<210> SEQ ID NO 16
<211> LENGTH: 10
<212> TYPE: PRT
<213> ORGANISM: Mus sp.

<400> SEQUENCE: 16

```
Ser Ala Ser Ser Ser Val Ser Tyr Met His
 1               5                  10
```

<210> SEQ ID NO 17
<211> LENGTH: 7
<212> TYPE: PRT
<213> ORGANISM: Mus sp.

<400> SEQUENCE: 17

```
Asp Thr Ser Lys Leu Ala Ser
 1               5
```

<210> SEQ ID NO 18
<211> LENGTH: 9
<212> TYPE: PRT
<213> ORGANISM: Mus sp.

<400> SEQUENCE: 18

```
His Gln Leu Ser Ser Asp Pro Phe Thr
 1               5
```

```
<210> SEQ ID NO 19
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Arg Leu Glu Trp Met
        35                  40                  45

Gly Tyr Ile Asn Pro Ser Asn Asp Tyr Thr Lys Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Phe Pro Tyr Trp Gly Gln Gly Thr Leu Val Thr Val
            100                 105                 110

Ser Ser

<210> SEQ ID NO 20
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Arg Leu Glu Trp Met
        35                  40                  45

Gly Tyr Ile Asn Pro Ser Asn Asp Tyr Thr Lys Tyr Asn Gln Lys Phe
    50                  55                  60

Lys Asp Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Phe Pro Tyr Trp Gly Gln Gly Thr Leu Val Thr Val
            100                 105                 110

Ser Ser

<210> SEQ ID NO 21
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Arg Leu Glu Trp Ile
        35                  40                  45

Gly Tyr Ile Asn Pro Ser Asn Asp Tyr Thr Lys Tyr Asn Gln Lys Phe
    50                  55                  60

Lys Asp Arg Ala Thr Leu Thr Ala Asp Lys Ser Ala Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Gln Gly Phe Pro Tyr Trp Gly Gln Gly Thr Leu Val Thr Val
            100                 105                 110

Ser Ser

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Leu Ser Ser Asp Pro Phe Thr
            85                  90                  95

Phe Gly Gly Gly Thr Lys Val Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu

```
                65                  70                  75                  80
Asp Phe Ala Val Tyr Tyr Cys His Gln Leu Ser Ser Asp Pro Phe Thr
                    85                  90                  95

Phe Gly Gly Gly Thr Lys Val Glu Ile Lys
                100                 105
```

<210> SEQ ID NO 24
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Arg Leu Glu Trp Ile
            35                  40                  45

Gly Tyr Ile Asn Pro Ser Asn Asp Tyr Thr Lys Tyr Asn Gln Lys Phe
        50                  55                  60

Lys Asp Arg Ala Thr Leu Thr Ala Asp Lys Ser Ala Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Phe Pro Tyr Trp Gly Gln Gly Thr Leu Val Thr Val
                100                 105                 110

Ser Ser
```

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Arg Leu Glu Trp Ile
            35                  40                  45

Gly Tyr Ile Asn Pro Ser Asn Asp Tyr Thr Lys Tyr Asn Gln Lys Phe
        50                  55                  60

Lys Asp Arg Ala Thr Leu Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Phe Pro Tyr Trp Gly Gln Gly Thr Leu Val Thr Val
                100                 105                 110

Ser Ser
```

<210> SEQ ID NO 26
<211> LENGTH: 114

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Tyr Ile Asn Pro Ser Asn Asp Tyr Thr Lys Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Gly Phe Pro Tyr Trp Gly Gln Gly Thr Leu Val Thr Val
            100                 105                 110

Ser Ser

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys His Gln Leu Ser Ser Asp Pro Phe Thr
                85                  90                  95

Phe Gly Gly Gly Thr Lys Val Glu Ile Lys
            100                 105

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Ser Tyr Met
            20                  25                  30
```

```
His Trp Tyr Gln Gln Lys Pro Gly Lys Ala Pro Lys Leu Leu Ile Tyr
            35                  40                  45

Asp Thr Ser Lys Leu Ala Ser Gly Val Pro Ala Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys His Gln Leu Ser Ser Asp Pro Phe Thr
                 85                  90                  95

Phe Gly Gln Gly Thr Lys Val Glu Val Lys
            100                 105

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Val Ser Tyr Met
                 20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys His Gln Leu Ser Ser Asp Pro Phe Thr
                 85                  90                  95

Phe Gly Gln Gly Thr Lys Leu Glu Ile Lys
            100                 105

<210> SEQ ID NO 30
<211> LENGTH: 109
<212> TYPE: PRT
<213> ORGANISM: Homo sapiens

<400> SEQUENCE: 30

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Gln Gly Thr Leu Val Thr Val Ser Ser
            100                 105

<210> SEQ ID NO 31
```

<211> LENGTH: 98
<212> TYPE: PRT
<213> ORGANISM: Homo sapiens

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Phe Gly Gly Gly Thr Lys Val Glu
                85                  90                  95

Ile Lys

<210> SEQ ID NO 32
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| atggactgga | cctggaggat | tctctttttg | gtggcagcag | ccacaggtgc | ccactcccaa | 60 |
| gtgcagcttg | tccagtccgg | agccgaggtg | aaaaagcccg | tgcctcagt  | aaaggtctcc | 120 |
| tgcaaggcct | ctggctatac | tttcaccaat | tattggatgc | actgggtgag | gcaggctccc | 180 |
| ggacagcgcc | tcgaatggat | cggttatatc | aacccatcta | acgattacac | caaatacaat | 240 |
| cagaaattca | aggaccgggc | cacactgaca | gctgataaaa | gcgctaacac | agcttacatg | 300 |
| gaacttagct | ctctgcgaag | cgaggatacc | gctgtatact | actgcgcaag | cagggctttt | 360 |
| ccttactggg | gcagggcac  | tctcgttact | gtgagtagtg | ctagcaccaa | gggcccatcg | 420 |
| gtcttccccc | tggcgccctg | ctccaggagc | acctccgaga | gcacagccgc | cctgggctgc | 480 |
| ctggtcaagg | actacttccc | cgaaccggtg | acggtgtcgt | ggaactcagg | cgccctgacc | 540 |
| agcggcgtgc | acaccttccc | ggctgtccta | cagtcctcag | gactctactc | cctcagcagc | 600 |
| gtggtgaccg | tgccctccag | cagcttgggc | acgaagacct | acacctgcaa | cgtagatcac | 660 |
| aagcccagca | acaccaaggt | ggacaagaga | gttgagtcca | aatatggtcc | cccatgccca | 720 |
| ccatgcccag | cacctgagtt | cctgggggga | ccatcagtct | tcctgttccc | cccaaaaccc | 780 |
| aaggacactc | tcatgatctc | ccggacccct | gaggtcacgt | gcgtggtggt | ggacgtgagc | 840 |
| caggaagacc | ccgaggtcca | gttcaactgg | tacgtggatg | gcgtggaggt | gcataatgcc | 900 |
| aagacaaagc | cgcgggagga | gcagttcaac | agcacgtacc | gtgtggtcag | cgtcctcacc | 960 |
| gtcctgcacc | aggactggct | gaacggcaag | gagtacaagt | gcaaggtctc | caacaaaggc | 1020 |
| ctcccgtcct | ccatcgagaa | aaccatctcc | aaagccaaag | gcagccccg  | agagccacag | 1080 |
| gtgtacaccc | tgcccccatc | ccaggaggag | atgaccaaga | accaggtcag | cctgacctgc | 1140 |
| ctggtcaaag | gcttctaccc | cagcgacatc | gccgtggagt | gggagagcaa | tgggcagccg | 1200 |
| gagaacaact | acaagaccac | gcctcccgtg | ctggactccg | acggctcctt | cttcctctac | 1260 |

```
agcaggctca ccgtggacaa gagcaggtgg caggagggga atgtcttctc atgctccgtg    1320
atgcatgagg ctctgcacaa ccactacaca cagaagagcc tctccctgtc tccgggtaaa    1380
tga                                                                   1383
```

<210> SEQ ID NO 33
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Arg Leu
    50                  55                  60

Glu Trp Ile Gly Tyr Ile Asn Pro Ser Asn Asp Tyr Thr Lys Tyr Asn
65                  70                  75                  80

Gln Lys Phe Lys Asp Arg Ala Thr Leu Thr Ala Asp Lys Ser Ala Asn
                85                  90                  95

Thr Ala Tyr Met Glu Leu Ser Ser Leu Arg Ser Glu Asp Thr Ala Val
            100                 105                 110

Tyr Tyr Cys Ala Arg Gln Gly Phe Pro Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335
```

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
            355                 360                 365

Glu Glu Met Thr Lys Asn Gln Val Ser Leu Thr Cys Leu Val Lys Gly
370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 34
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggaagccc cagctcagct tctcttcctc ctgctactct ggctcccaga taccaccgga      60
gagattgtgc tgactcagtc accagcaaca ctgagtctct ctcccggcga gcgtgctaca     120
ctgtcctgtt ccgcaagcag ctcagtgtcc tacatgcact ggtatcagca aaagcccggc     180
caggccccca gacggtggat ctatgacaca tccaagttgg cttccggcgt ccccgcacgg     240
ttttcaggct caggaagcgg tactgattac actttgacca ttagctctct gaacctgag     300 gacttcgcag tatactactg ccaccagctg agttccgatc cttttacctt tggtggtggt     360
actaaggtcg agatcaaacg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702

<210> SEQ ID NO 35
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

-continued

```
Val Ser Tyr Met His Trp Tyr Gln Gln Lys Pro Gly Gln Ala Pro Arg
    50              55                  60
Arg Trp Ile Tyr Asp Thr Ser Lys Leu Ala Ser Gly Val Pro Ala Arg
65              70                  75                  80
Phe Ser Gly Ser Gly Ser Gly Thr Asp Tyr Thr Leu Thr Ile Ser Ser
                85                  90                  95
Leu Glu Pro Glu Asp Phe Ala Val Tyr Tyr Cys His Gln Leu Ser Ser
            100                 105                 110
Asp Pro Phe Thr Phe Gly Gly Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225             230
```

HUMANIZED ANTI-CD40 ANTIBODIES AND METHODS OF ADMINISTERING THEREOF

CROSS REFERENCE TO RELATED APPLICATION

This application is a continuation of U.S. patent application Ser. No. 15/955,393 filed Apr. 17, 2018, which is a division of U.S. patent application Ser. No. 15/829,352 filed Dec. 1, 2017, which is a continuation of International Patent Application No. PCT/US16/50114 filed Sep. 2, 2016, which claims benefit of U.S. Provisional Application No. 62/214,411 filed Sep. 4, 2015.

SEQUENCE LISTING

This application contains a Sequence Listing which has been filed electronically in ASCII format and is hereby incorporated by reference in its entirety. Said ASCII copy, created on Dec. 26, 2018, is named 11212_005211-US3_ST25.txt and is 33,416 bytes in size.

FIELD

The invention relates to humanized anti-CD40 antibodies and uses of such antibodies, for example, to reduce the likelihood of, or treat, transplant rejection, to induce immunosuppression, or to treat an autoimmune disorder.

BACKGROUND OF THE INVENTION

Suppression of the immune system, particularly the humoral immune system, is beneficial in organ transplantation and treatment of autoimmune disorders. Organ transplantation has emerged as a preferred method of treatment for many forms of life-threatening diseases that involve organ damage. However, transplantation rejection may occur when an organism receiving transplanted cells or tissue mounts an undesired immune response to that tissue. Transplant rejection may be minimized by tissue-type matching, but even matched tissue can be rejected by the donor. Thus, immunosuppressive therapies are now used for virtually all cases of tissue transplantation.

Improved results in clinical transplantation have been achieved primarily through the development of increasingly potent non-specific immunosuppressive drugs to inhibit rejection responses. While short-term results have improved, long-term outcomes remain inadequate. Life-long immunosuppressive agents may be required to combat chronic rejection of the transplanted organ, and the use of these agents dramatically increases the risks of cardiovascular disease, infections, and malignancies.

One potential target for reducing transplantation rejection is the CD40/CD154 interaction. CD40 is expressed primarily on the surface of B lymphocytes and other antigen-presenting cells (APCs) such as dendritic cells and macrophages. CD154 is expressed primarily on the surface of T cells. The interaction between these two proteins is associated with B cell activation, which triggers cytokine expression as well as expression of cell surface markers including CD23, CD80, and CD86, Kehry M. R., CD40-mediated signaling in B cells. Balancing cell survival, growth, and death, J. Immunol. 1996; 156: 2345-2348. Blockade of this interaction using anti-CD154 antibodies has been shown to reduce or eliminate rejection of transplanted tissues in non-human primates.

For any type of immunosuppression (e.g., in a transplantation procedure), a balance between efficacy and toxicity is a key factor for its clinical acceptance. Thus, there is a need for therapies that specifically target the immunological pathways involved in, for example, transplant rejection and autoimmune disorders.

SUMMARY

The present disclosure provides, for a humanized anti-CD40 antibody, or an antigen-binding portion thereof, comprising a heavy chain variable region, wherein the heavy chain variable region comprises three CDRs, CDR1, CDR2 and CDR3, having amino acid sequences about 80% to about 100% identical to the amino acid sequences set fonts in SEQ ID NOs: 13, 14 and 15, respectively.

The present disclosure also provides for a humanized anti-CD40 antibody, or an antigen-binding portion thereof, comprising a light chain variable region, wherein the light chain variable region comprises three CDRs, CDR1, CDR2 and CDR3, having amino acid sequences about 80% to about 100%, identical to the amino acid sequences set forth in SEQ ID NOs: 16, 17 and 18, respectively.

Also encompassed by the present disclosure is a humanized anti-CD40 antibody, or an antigen-binding portion thereof, comprising a heavy chain variable region and a light chain variable region, wherein the heavy chain variable region comprises three complementarity determining regions (CDRs), CDR1, CDR2 and CDR3 having amino acid sequences about 80% to about 100% identical to the amino acid sequences set forth in SEQ ID NOs: 13, 14 and 15, respectively, and wherein the light chain variable region comprises three CDRs, CDR1, CDR2 and CDR3, having amino acid sequences about 80% to about 100% identical to the amino acid sequences set forth in SEQ ID NOs: 16, 17 and 18, respectively.

The present disclosure provides for a humanized anti-CD40 antibody, or an antigen-binding portion thereof, comprising a heavy chain variable region and a light chain variable region, wherein the heavy chain variable region comprises an amino acid sequence about 80% to about 100% identical to any one of the amino acid sequences set forth in SEQ ID NOs. 11, 19, 20, 21, 24, 25 and 26.

The present disclosure provides for a humanized anti-CD40 antibody, or an antigen-binding portion thereof, comprising a heavy chain variable region and a light chain variable region, wherein the light chain variable region comprises an amino acid sequence about 80% to about 100% identical to any one of the amino acid sequences set forth in SEQ ID NOs: 12, 22, 23, 27, 28 and 29.

The present disclosure provides for a humanized anti-CD40 antibody, or an antigen-binding portion thereof, comprising a heavy chain variable region and a light chain variable region, wherein the heavy chain variable region comprises an amino acid sequence about 80% to about 100%, identical to any one of the amino acid sequences set forth in SEQ ID NOs: 11, 19, 20, 21, 24, 25 and 26, and wherein the light chain variable region comprises an amino acid sequence about 80% to about 100% identical to any one of the amino acid sequences set forth in SEQ ID NOs: 12, 22, 23, 27, 28 and 29.

The present disclosure provides for a humanized anti-CD40 antibody, or an antigen-binding portion thereof, comprising a heavy chain variable region and a light chain variable region, wherein the heavy chain variable region comprises an amino acid sequence about 80% to about 100% identical to any one of the amino acid sequences set forth in SEQ ID NOs: 19, 20 and 21, and wherein the light chain variable region comprises an amino acid sequence about 80% to about 100% identical to either of the amino acid sequences set forth in SEQ ID NOs: 22 and 23.

The present disclosure provides for a humanized anti-CD40 antibody or an antigen-binding portion thereof, comprising a heavy chain variable region and a light chain variable region, wherein the heavy chain variable region comprises an amino acid sequence about 80% to about 100% identical to any one of the amino acid sequences set forth in SEQ ID NOs: 24, 25 and 26, and wherein the light chain variable region comprises an amino acid sequence about 80% to about 100% identical to any one of the amino acid sequences set forth in SEQ ID NOs: 27, 28 and 29.

The present disclosure provides for a humanized anti-CD40 antibody, or an antigen-binding portion thereof, comprising a heavy chain variable region and a light chain variable region, wherein the heavy chain variable region comprises an amino acid sequence about 80% to about 100% identical to the amino acid sequences set forth in SEQ ID NO: 21, and wherein the light chain variable region comprises an amino acid sequence about 80% to about 100% identical to the amino acid sequences set forth in SEQ ID NO: 23.

The dissociation constant ($K_D$) of the antibody, or antigen-binding portion thereof, may be less than about $1\times10^{-9}$ M, or less than about $1\times10^{-8}$ M.

The present antibody or antigen-binding portion thereof may be: (a) a whole immunoglobulin molecule; (b) an scFv; (c) a Fab fragment; (d) an F(ab')2; and/or (e) a disulfide linked Fv.

The present antibody or antigen-binding portion thereof may comprise at least one constant domain selected from; a) an IgG constant domain; and (b) an IgA constant domain.

The present antibody or antigen-binding portion thereof may comprise at least one human constant domain.

The present antibody or antigen-binding portion thereof may bind to CD40 extracellular domain.

The CD40 may be human or rhesus CD40.

The present antibody or antigen-binding portion thereof may block B lymphocyte activation by CD154-expressing Jurkat cells in vitro.

The present antibody or antigen-binding portion thereof may inhibit B lymphocyte CD23, CD80, or CD86 expression.

Also encompassed by the present disclosure is a composition comprising the present antibody or antigen-binding portion thereof, and at least one pharmaceutically acceptable carrier.

The present disclosure provides for a polynucleotide encoding the present antibody or antigen-binding portion thereof. The present disclosure provides for a vector comprising the present polynucleotide, and a cell comprising the vector.

The present disclosure provides for an isolated polypeptide comprising the present antibody or antigen-binding portion thereof.

Also encompassed by the present disclosure is a method of producing the present antibody or antigen-binding portion thereof. The method may comprise the following steps: (a) culturing the present cells in culture medium under conditions wherein the polynucleotide encoding the present antibody or antigen-binding portion thereof is expressed, thereby producing at least one polypeptide comprising the antibody or antigen-binding portion thereof; and (b) recovering the polypeptide from the cells or culture medium.

The present disclosure also provides for a method of suppressing the immune system in a subject, comprising the step of administering to the subject an effective amount of the present antibody or antigen-binding portion thereof.

The present disclosure provides for a method of treating or treating prophylactically transplant rejection, or increasing the duration of time before transplant rejection occurs, in a subject in need thereof, the method comprising the step of administering to the subject an effective amount of the present antibody or antigen-binding portion thereof.

The present disclosure provides for a method of treating or treating prophylactically graft-versus-host disease, in a subject in need thereof, the method comprising the step of administering to the subject an effective amount of the present antibody or antigen-binding portion thereof.

The present disclosure provides for a method of treating or treating prophylactically an autoimmune disorder in a subject in need thereof, the method comprising the step of administering to the subject an effective amount of the present antibody or antigen-binding portion thereof.

The subject may have received, or is in need of, an organ transplantation, and/or a tissue transplantation. The organ may be a heart, kidney, lung, liver, pancreas, intestine, and thymus, or a portion thereof. The tissue may be bone, tendon, cornea, skin, heart valve, vein, or bone marrow.

The subject may be a human or a mammal.

The administration may be commenced prior to the transplantation. The administration may continue for at least one month following the transplantation. The administration may continue for at least six months following the transplantation of the graft.

The autoimmune disorder may be associated with or caused by the presence of an autoantibody.

The autoimmune disorder may be systemic lupus erythematosus (SLE), CREST syndrome (calcinosis, Raynaud's syndrome, esophageal dysmotility, sclerodactyl, and telangiectasia), opsoclonus, inflammatory myopathy (e.g., polymyositis, dermatomyositis, and inclusion-body myositis), systemic scleroderma, primary biliary cirrhosis, celiac disease (e.g., gluten sensitive enteropathy), dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis, Lambert-Eaton myasthenic syndrome, Hashimoto's thyroiditis, Graves' disease, Paraneoplastic cerebellar degeneration, Stiff person syndrome, limbic encephalitis. Isaacs Syndrome, Sydenham's chorea, pediatric autoimmune neuropsychiatric disease associated with Streptococcus (PANDAS), encephalitis, diabetes mellitus type 1, and/or Neuromyelitis optica.

The autoimmune disorder may be pernicious anemia, Addison's disease, psoriasis, inflammatory bowel disease, psoriatic arthritis, Sjögren's syndrome, lupus erythematosus (e.g., discoid lupus erythematosus, drug-induced lupus erythematosus, and neonatal lupus erythematosus), multiple sclerosis, and/or reactive arthritis.

The autoimmune disorder may be polymyositis, dermatomyositis, multiple endocrine failure, Schmidt's syndrome, autoimmune uveitis, adrenalins, thyroidites, autoimmune thyroid disease, gastric atrophy, chronic hepatis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, alopecia arcata, pemphigoid, scleroderma, progressive systemic sclerosis, adult onset diabetes mellitus (e.g., type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampler's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic facitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, Waldenstrom's macroglobuierma, Epstein-Barr virus infection, mumps, Evan's syndrome, and/or autoimmune gonadal failure.

The administration may be parenteral, intravenous, subcutaneous, intramuscular, transdermal, oral, topical, intrathecal, or local.

The present method may further comprise administration of an immunosuppressant within six months of the administration of the present antibody or antigen-binding portion thereof.

The immunosuppressant may be a calcineurin inhibitor, tacrolimus, an mTor inhibitor, fingolimod, myriocin, alemtuzumab, rituximab, an anti-CD4 monoclonal antibody, an anti-LFA1 monoclonal antibody, an anti-LFA3 monoclonal antibody, an anti-CD45 antibody, an anti-CD19 antibody, monabetacept, belatacept, indolyl-ASC; azathioprine, lymphocyte immune globulin and anti-thymocyte globulin [equine], mycophenotate mofetil, mycophenolate sodium, daclizumab, basiliximab, cyclophosphamide, prednisone, prednisolone, leflunomide, FK778, FK779, 15-deoxyspergualin, busulfan, fludarabine, methotrexate, 6-mercaptopurine, 15-deoxyspergualin, LF15-0195, bredinin, brequinar, and/or muromonab-CD3. The calcineurin inhibitor may be cyclosporin A or cyclosporine B. The mTor inhibitor may be sirolimus, temsirolimus, zotarolimus, or everolimus. The anti-CD45 antibody may be an anti-CD45RB antibody. In one embodiment, the immunosuppressant is belatacept.

The present antibody or antigen-binding portion thereof and the immunosuppressant may be administered within one month, or within one week, of each other.

BRIEF DESCRIPTION OF THE DRAWINGS

FIG. 1 shows the variable regions from the heavy chain and the light chain of the 2C10 antibody. The nucleotide sequence shown for the heavy chain (SEQ ID NO: 1) includes a signal peptide (nucleotides 1-57; underlined) and the heavy chain variable sequence (nucleotides 58-396). The corresponding amino acid sequence is shown below (SEQ ID NO: 2), where amino acids 1-19 corresponding to the signal sequence (underlined) and amino acids 20-132 correspond to the heavy chain variable region.

The nucleotide sequence shown for the light chain (SEQ ID NO: 3) includes a signal peptide (nucleotides 1-66; underlined) and the light chain variable sequence (nucleotides 67-384). The corresponding amino acid sequence is shown below (SEQ ID NO: 4), where amino acids 1-22 correspond to the signal peptide (underlined) and amino acids 23-128 correspond to the light chain variable region.

Figure 2A:
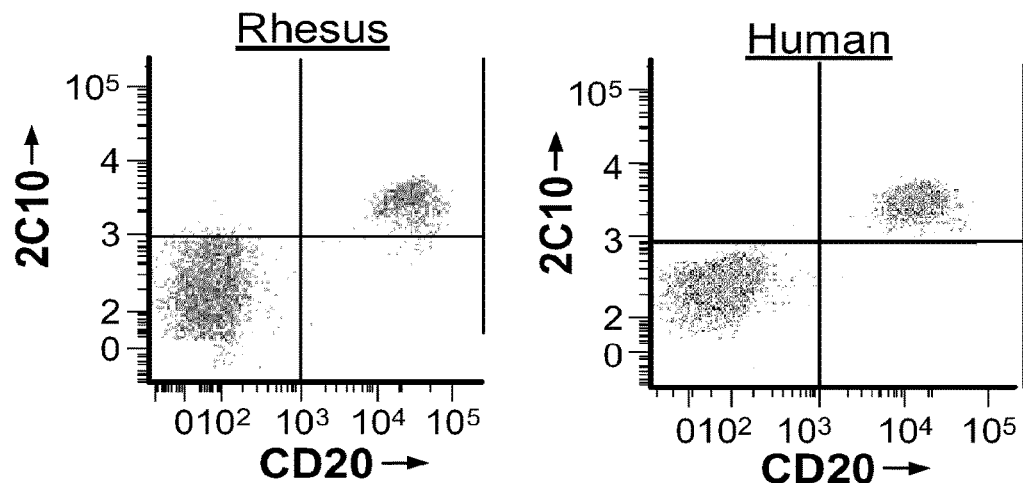

FIG. 2a is a plot showing flow cytometry data confirming the binding of 2C10 to human and rhesus CD20+ B cells.

Figure 2B:
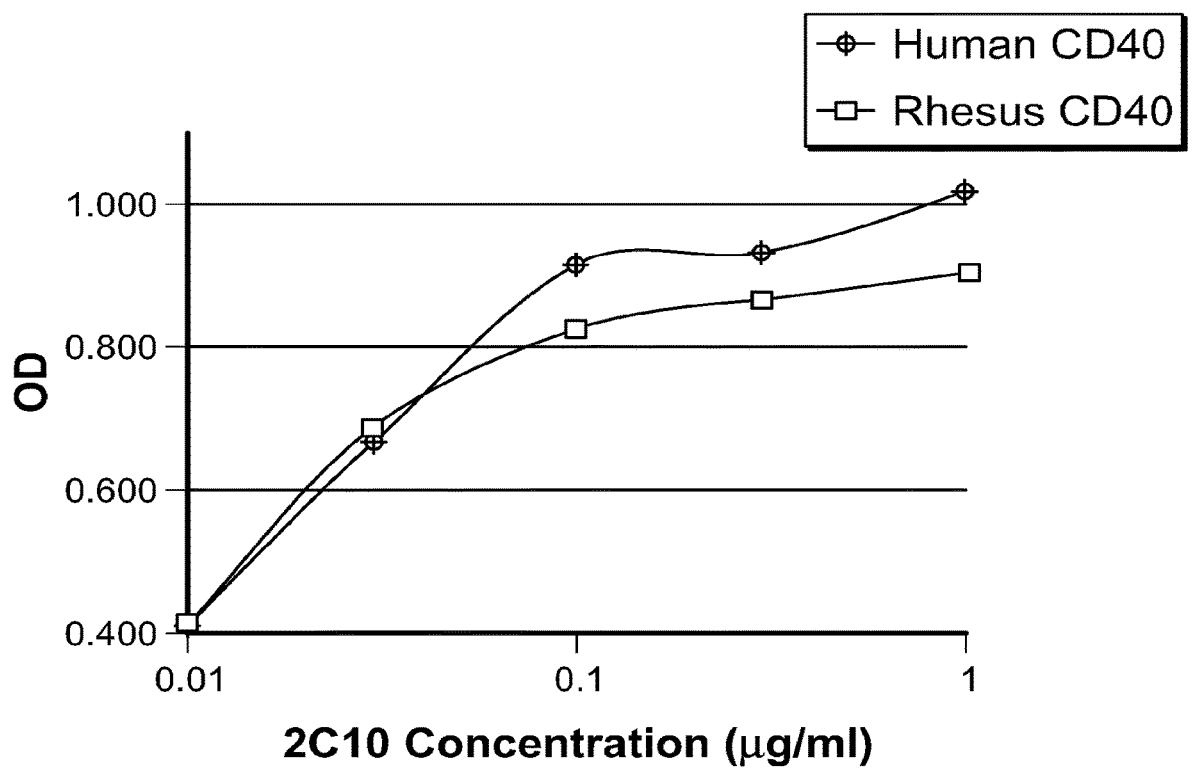

FIG. 2b is a plot showing CD40 adsorption data from ELISA assays with a varying concentrations of 2C10 to confirm the binding of 2C10 to human and rhesus CD40 as detected using goat anti-mouse IgG-HRP.

Figure 3:
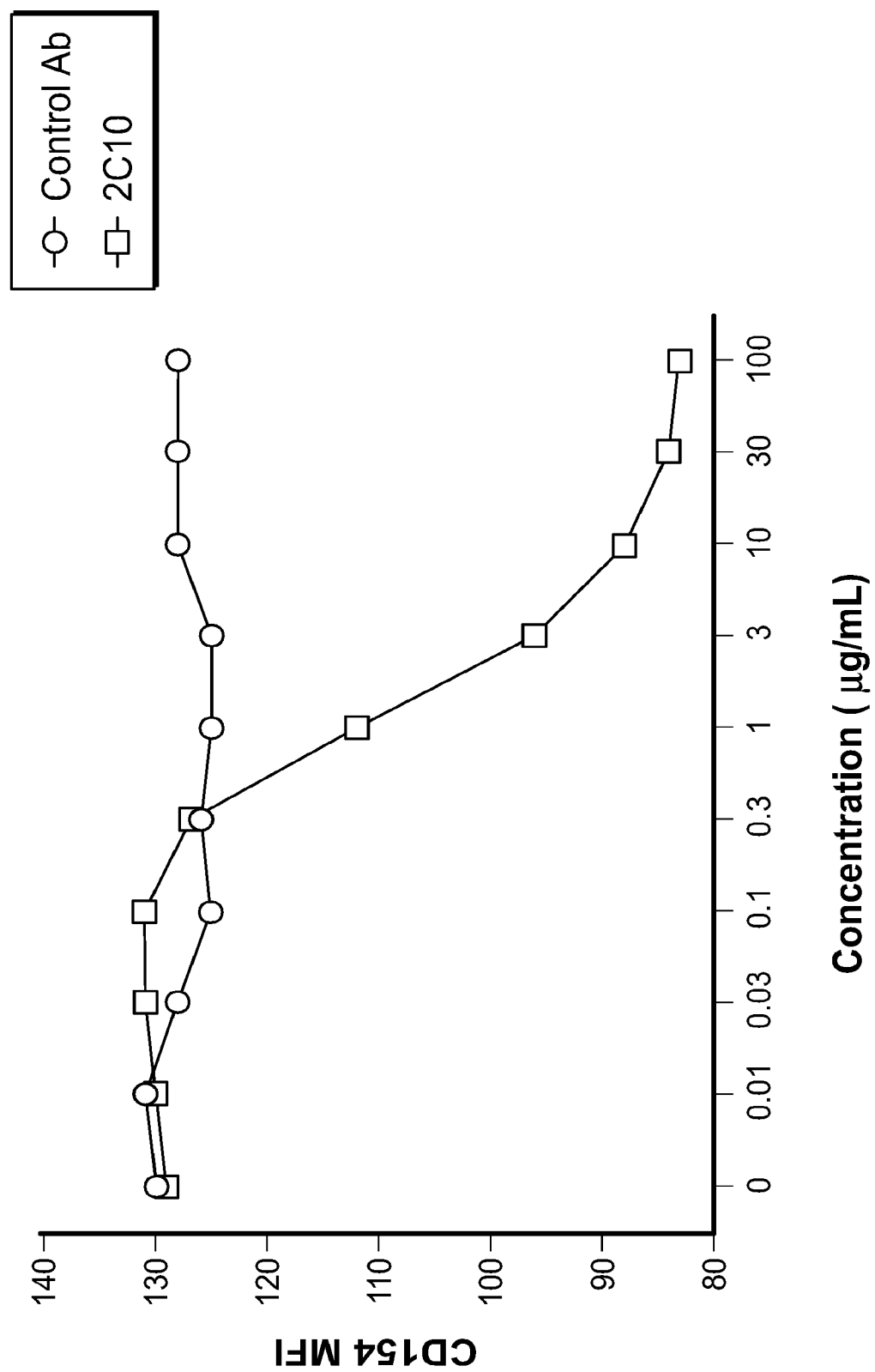

FIG. 3 is a graph showing the dose-dependent inhibition of CD154 binding to human B cells by 2C10. B cells were analyzed for CD154 binding by incubating with histidine-tagged soluble CD154 and analyzing for histidine expression. Results are representative of multiple repetitions of the experiment.

Figure 4:
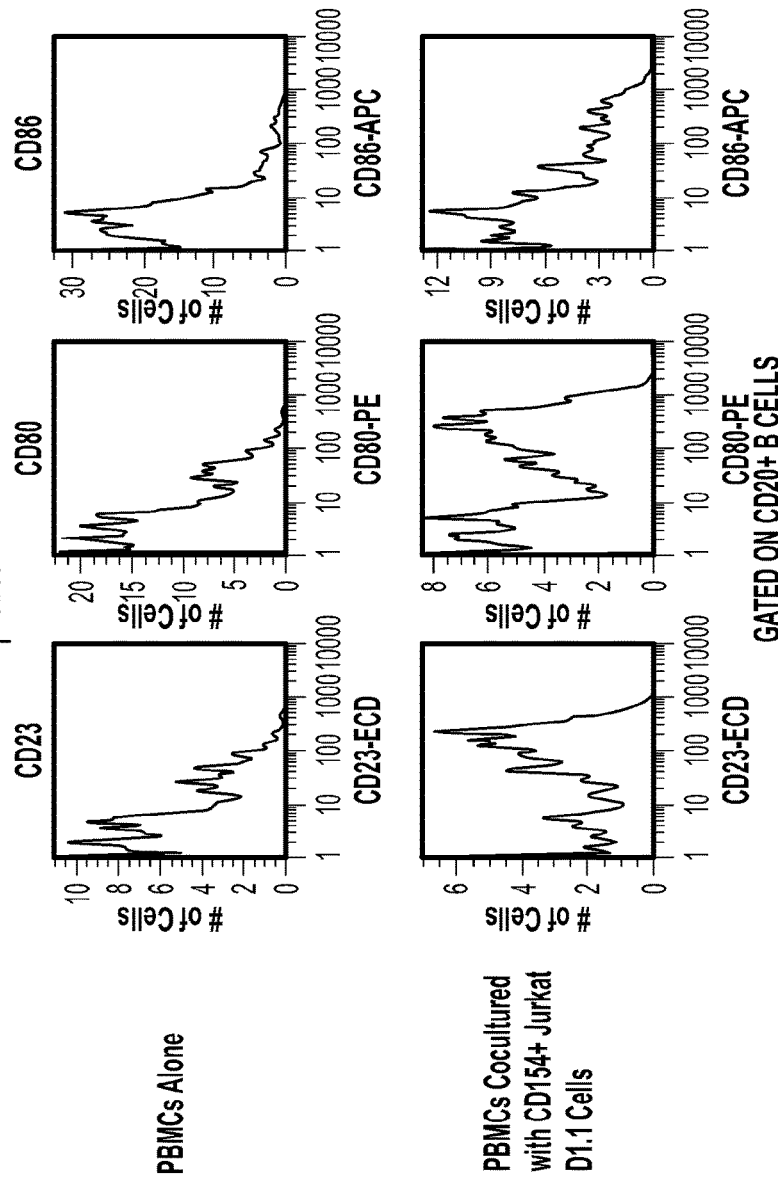

FIG. 4 is a schematic diagram and graphs showing the principle of the assay involving rhesus or human peripheral blood mononuclear cells (PBMCs) and Jurkat cells.

Figure 5:
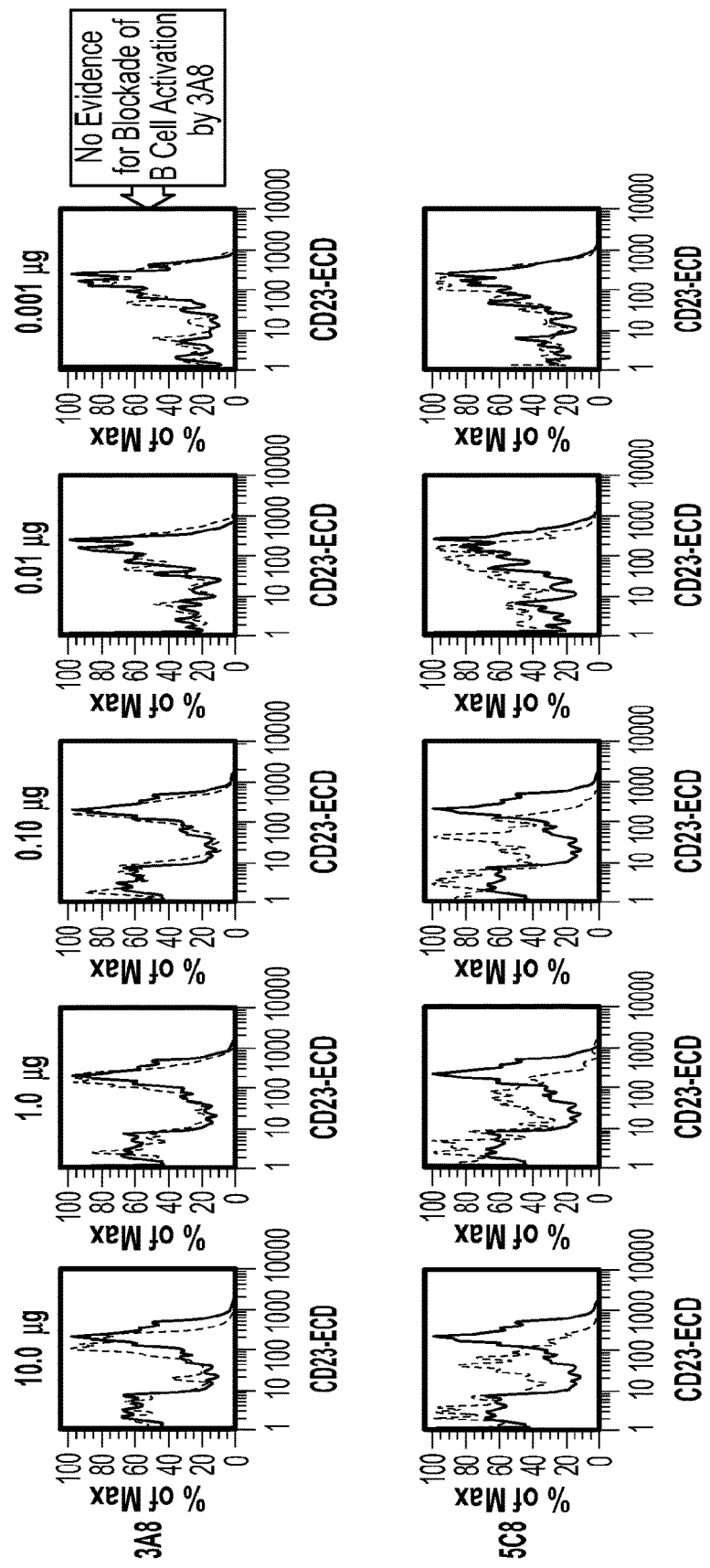
Figure 5:
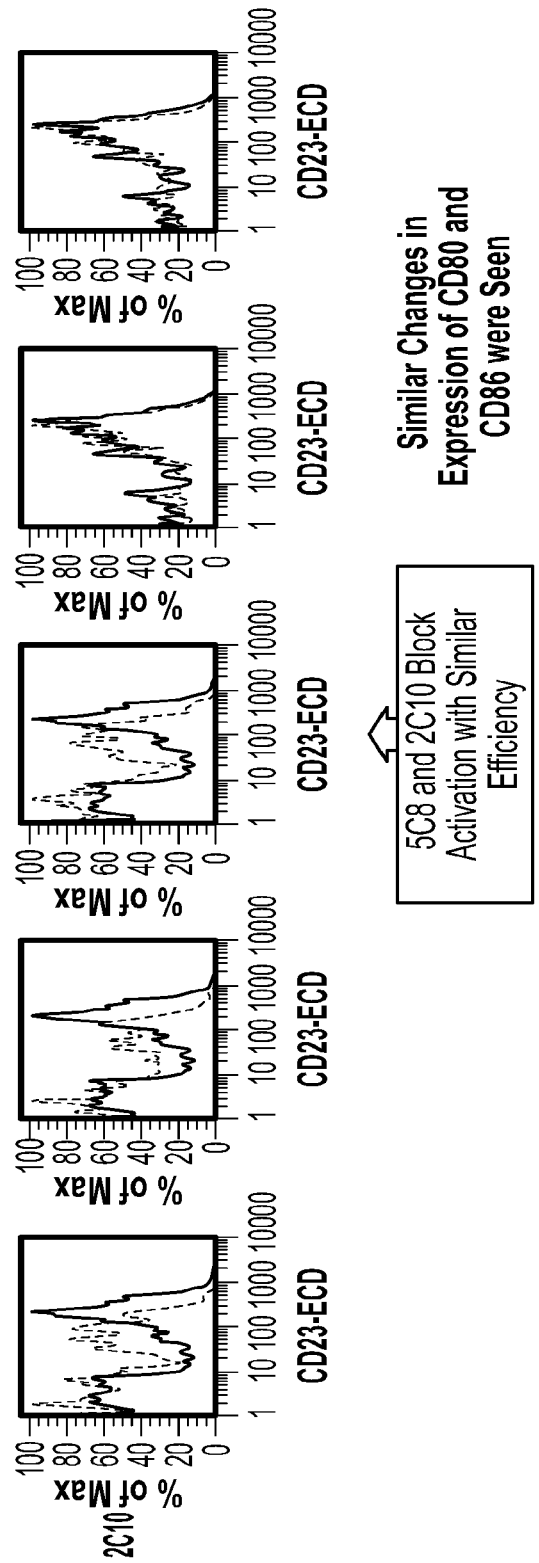

FIG. 5 is a set of graphs showing CD23 expression in CD20+ cells taken from co-cultures of rhesus PBMCs and Jurkat cells in the presence of variable concentrations of 3A8, 5C8, or 2C10 antibodies.

Figure 6:
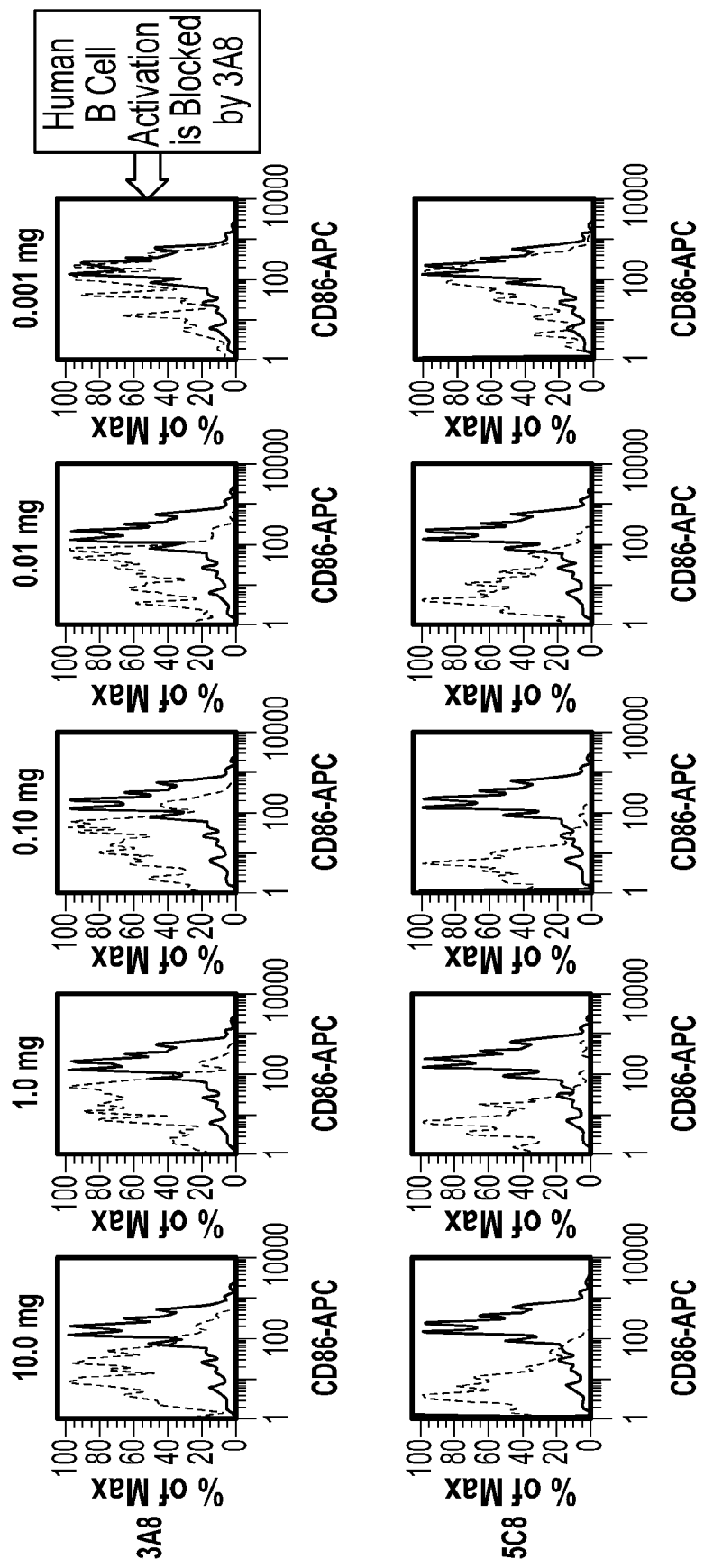
Figure 6:
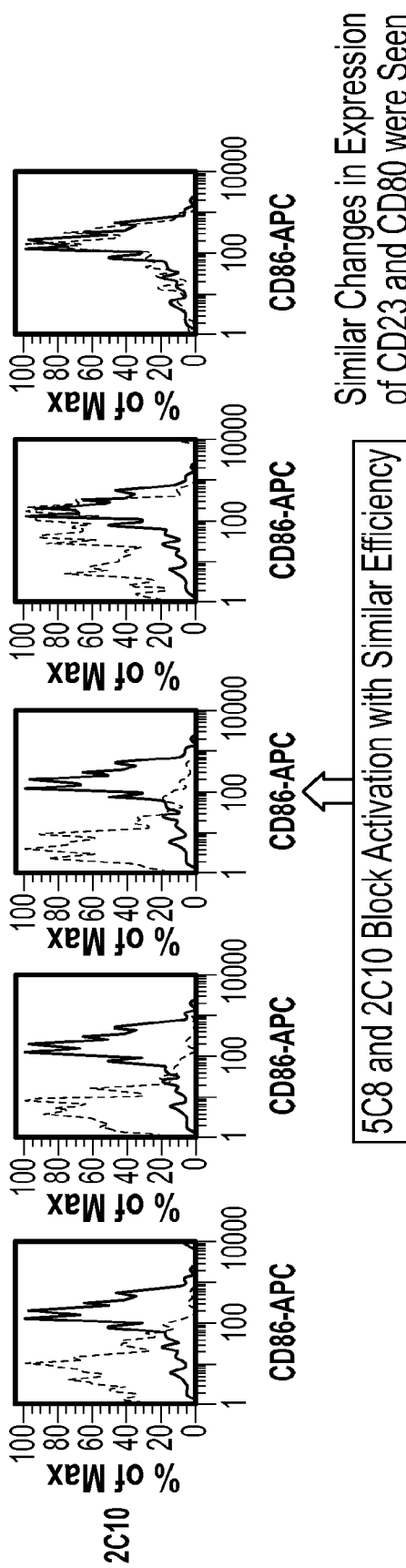

FIG. 6 is a set of graphs showing CD86 expression in CD20+ cells taken from co-cultures of human PBMCs and Jurkat cells in the presence of variable concentrations of 3A8, 5C8, or 2C10 antibodies.

Figure 7:
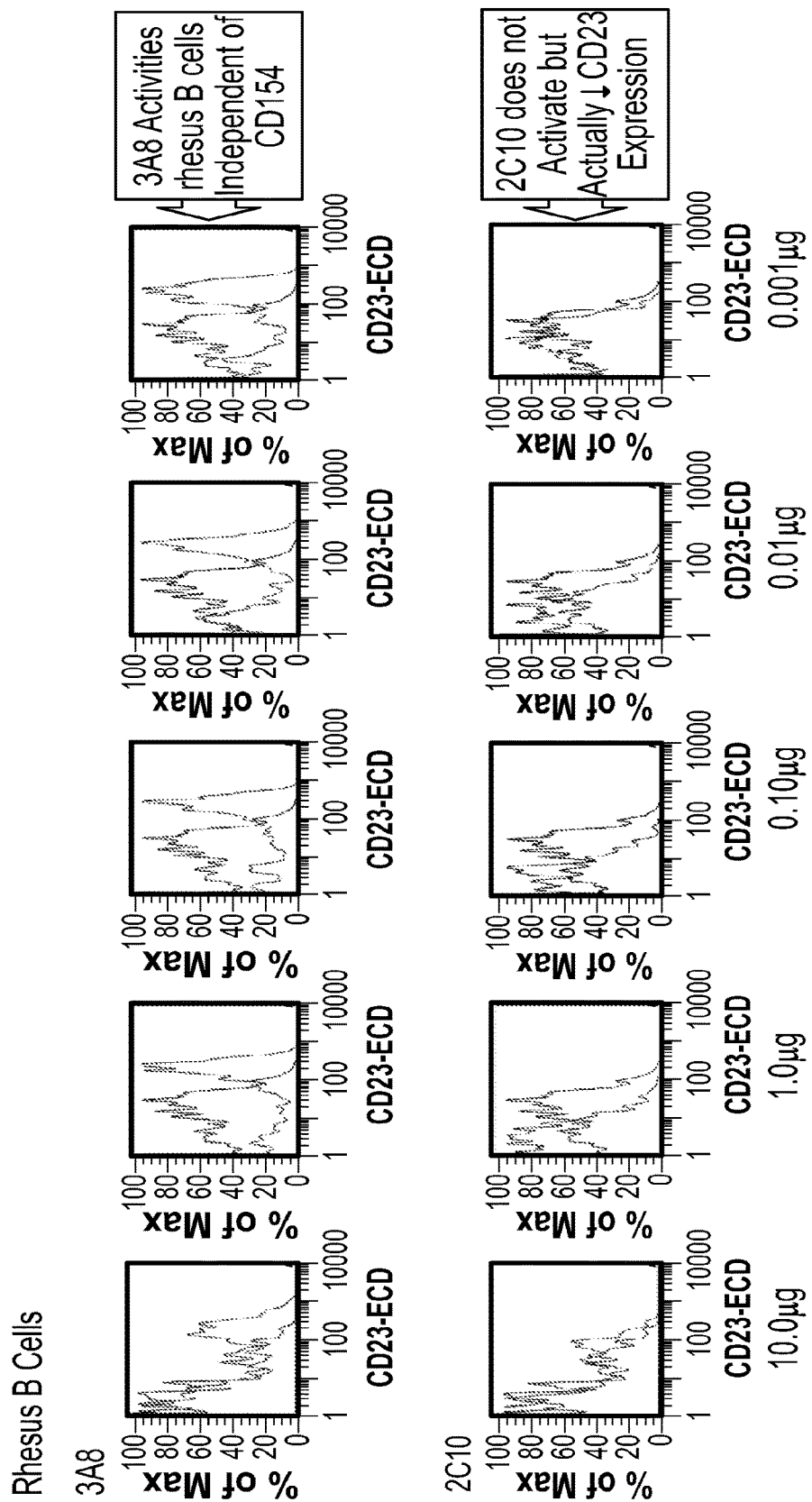
Figure 7:
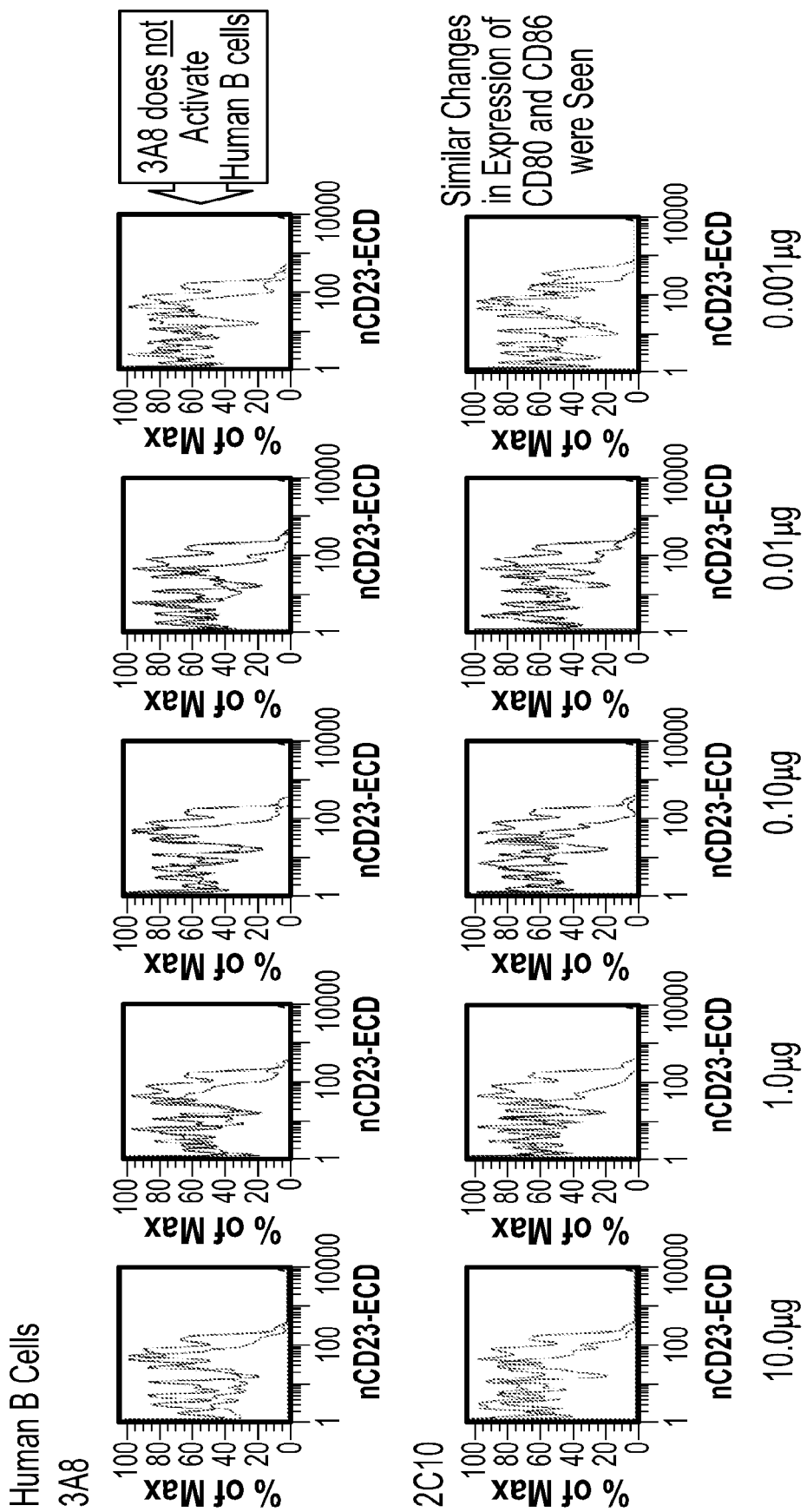

FIG. 7 is a set of graphs showing CD23 expression CD20' cells front either human or rhesus PSMCs cultured without Jutkat cells in the presence of cither the 3A8 or the 2C10 antibody.

Figure 8:
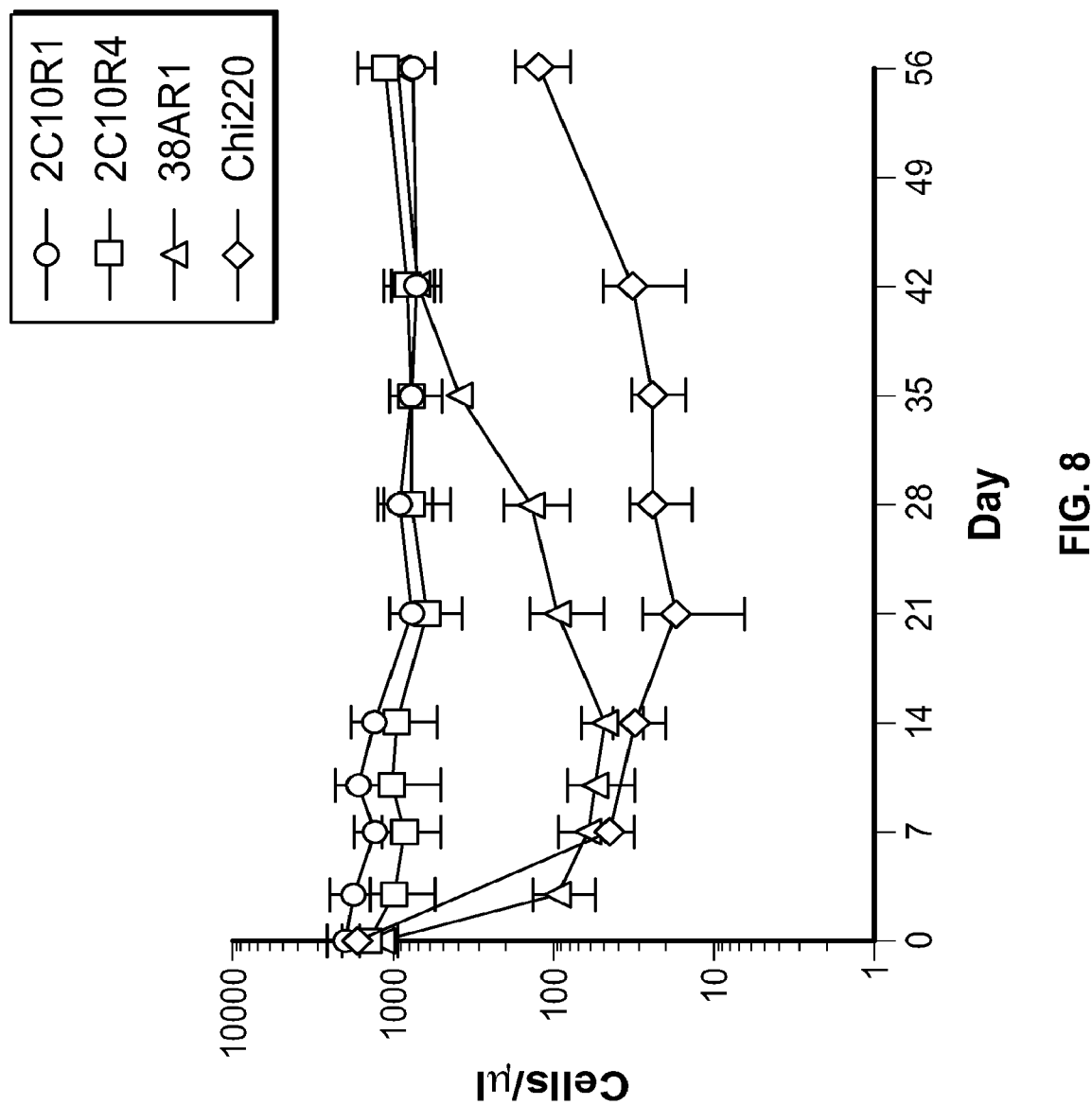

FIG. 8 is a graph showing peripheral B cell count of rhesus macaques treated with mouse-rhesus chimeric forms of 2C10 engineered to contain either rhesus IgG1 (2C10R1) or IgG4 I2C10R4) heavy chain constant regions, and chimeric IgG1 forms of anti-CD40 3A8 (3A8R1) or anti-CD40 Chi220 (Chi220).

Figure 9:
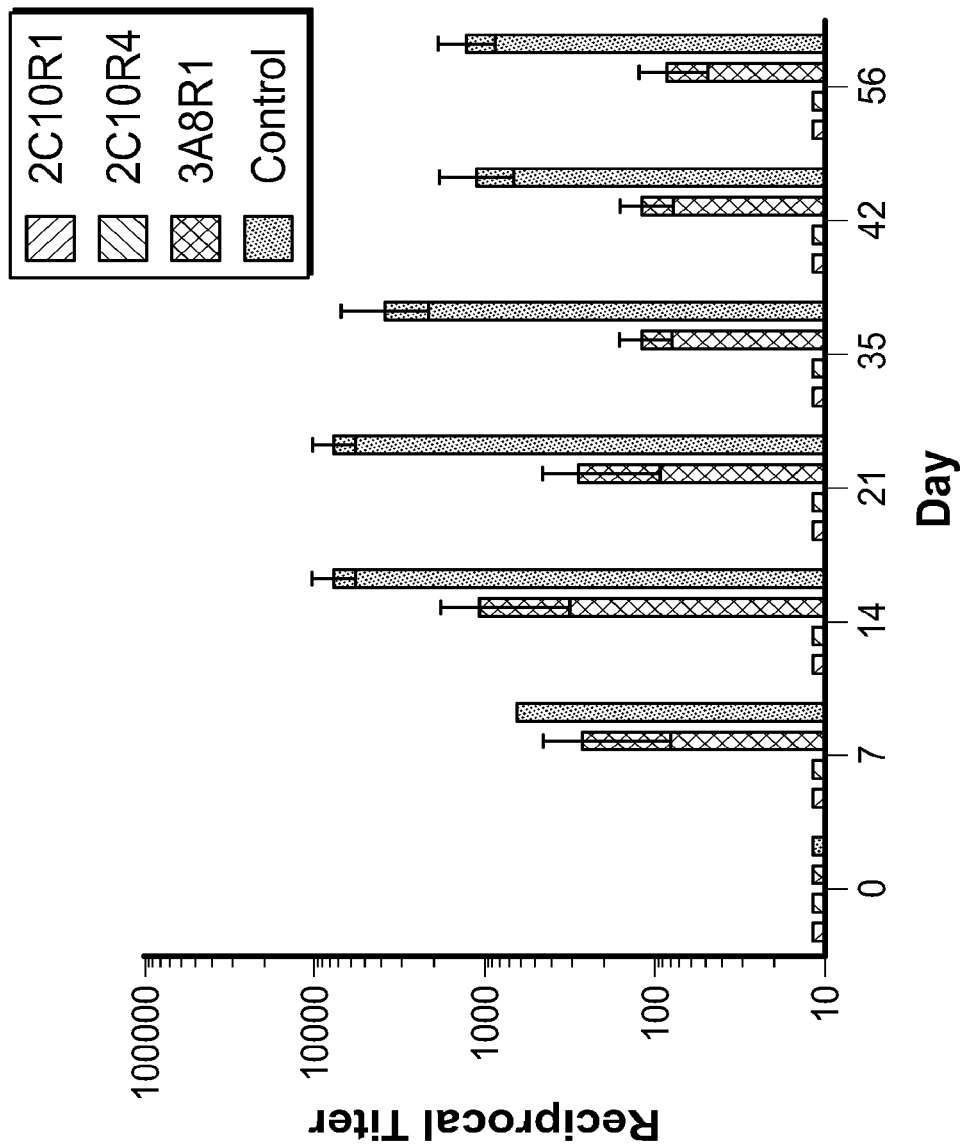

FIG. 9 is a graph showing T cell-dependent antibody responses in macaque monkeys treated with 2C10R1, 2C10R4, or 3A8R1 antibody. All animals were immunized with 4-hydroxy-3-nitrophenylacetyl-conjugated keyhole limpet hemocyanin (KLH) after the first antibody treatment.

Figure 10:
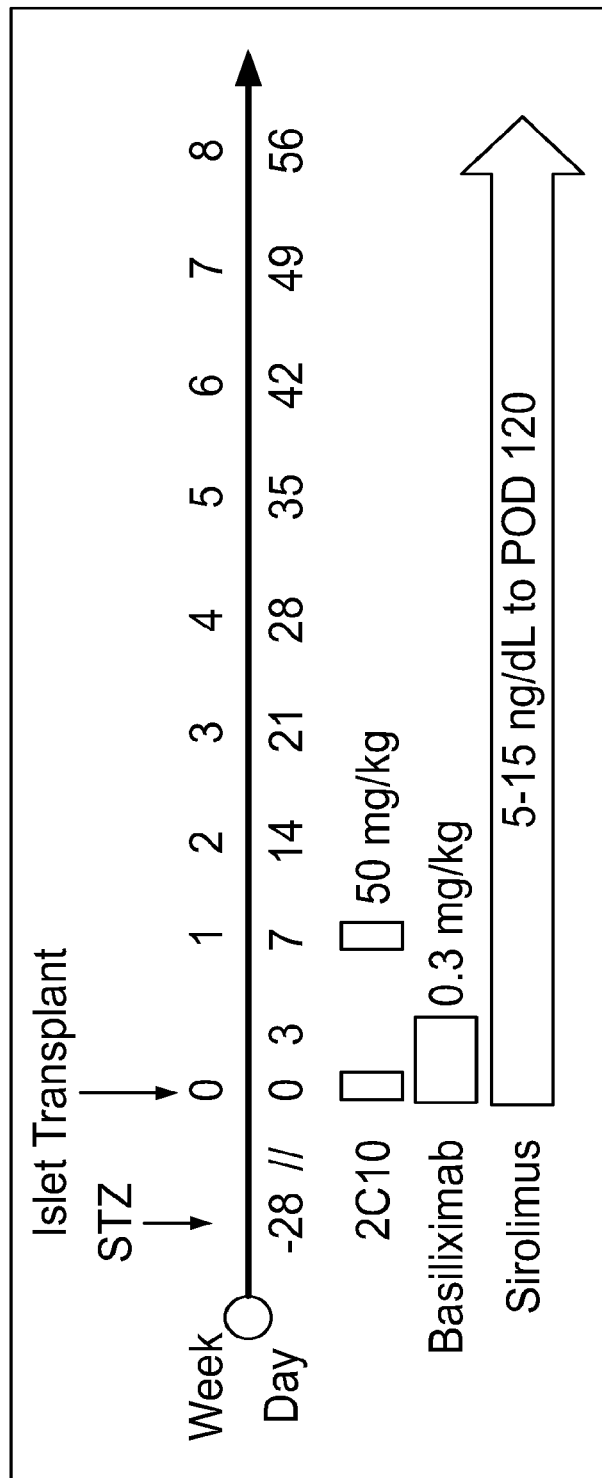

FIG. 10 is a diagram showing the standard macaque model of allogeneic islet transplantation. Diabetes was induced in macaque monkeys using streptozotocin. Diabetic monkeys were transplanted with allogeneic islets and immunosuppression initiated with basiliximab and sirolumus. Experimental animals received 2C10R4 treatment on days 0 and 7 post-transplantation.

Figures 11A, 11B:
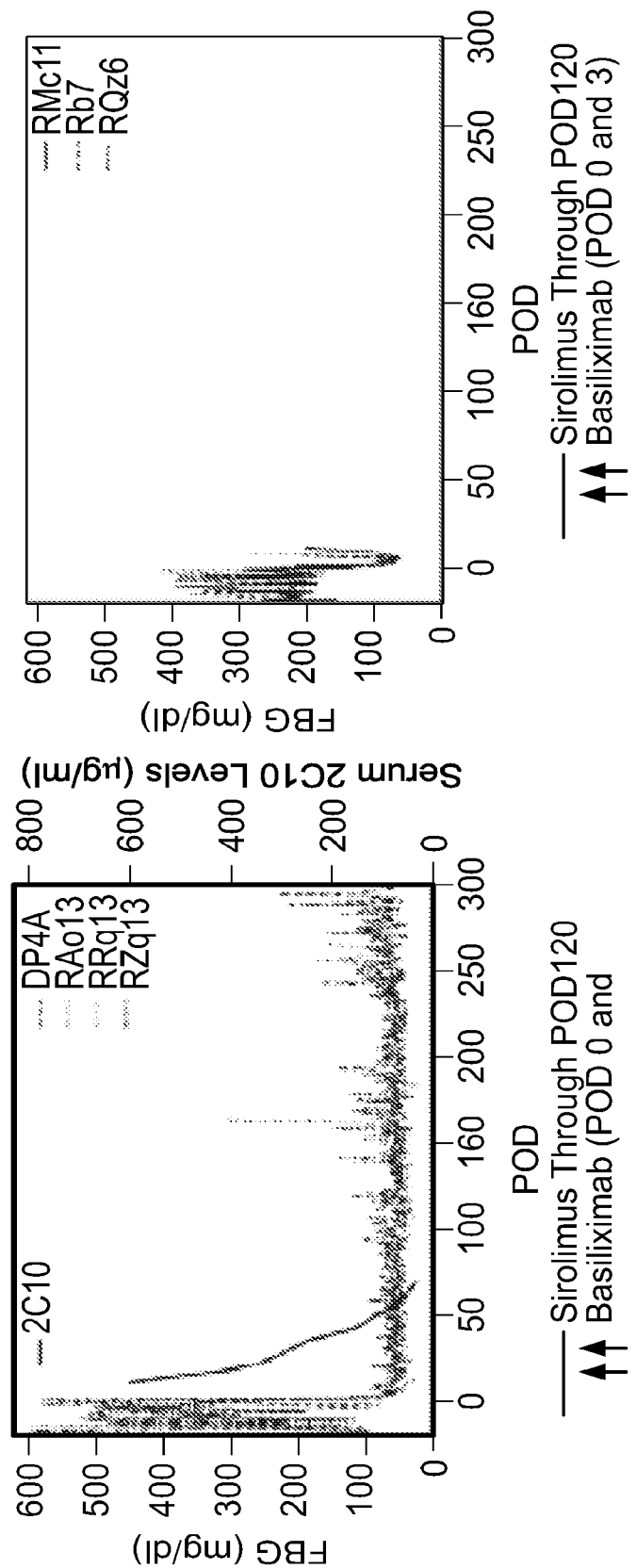

FIG. 11a is a plot showing free blood glucose levels (FBG) in 4 macaques following islet transplantation, background immunosuppression, and treatment with 2C10R4. The solid line on the plot represents the level of 2C10 in the plasma.

FIG. 11b is a plot showing FBG in macaques that received only background immunosuppression.

Figure 12:
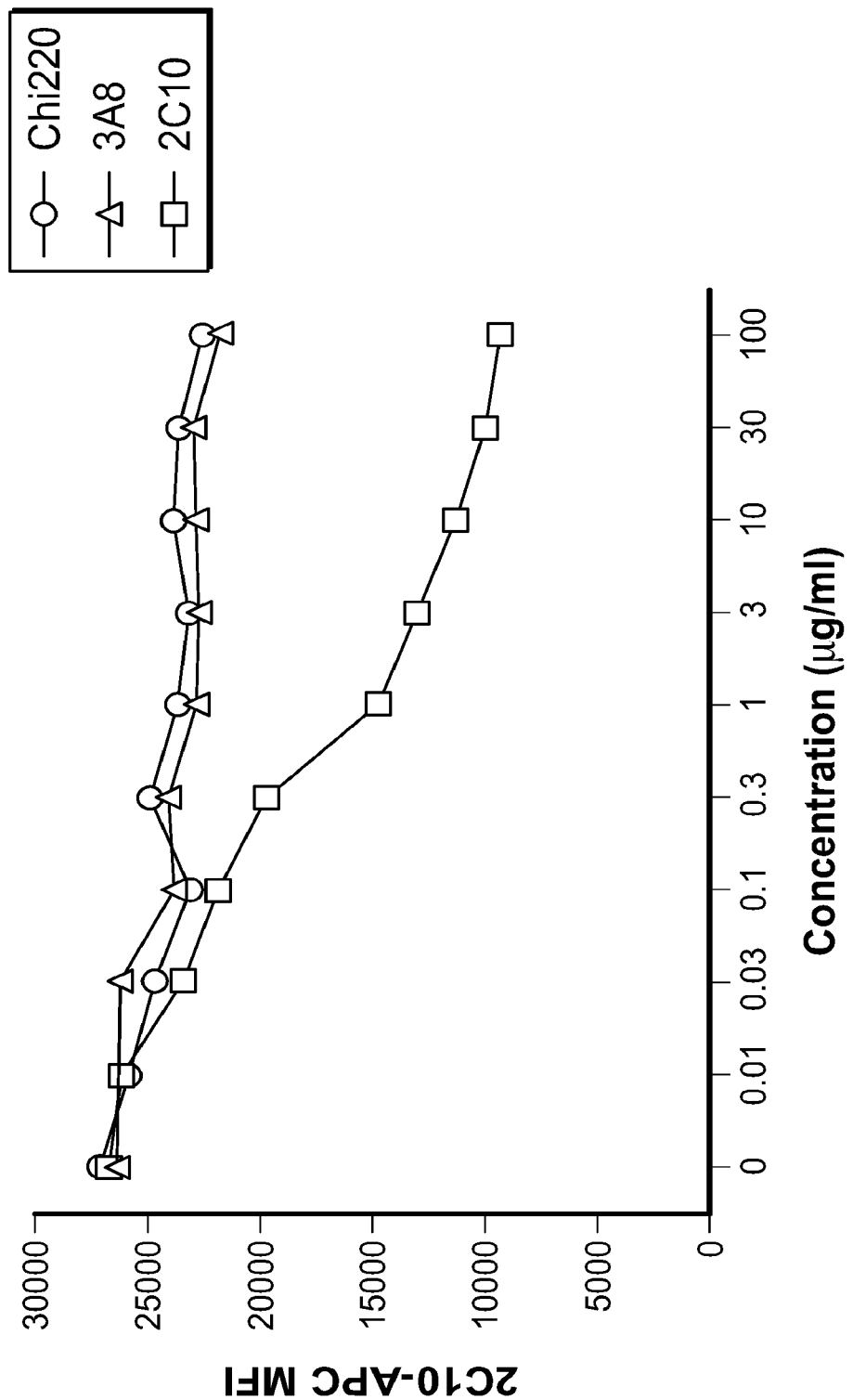

FIG. 12 is a graph showing results from a competitive blockade assay using human PBMCs incubated with increasing concentrations of 2C10, 3A8, or Chi220 antibodies and stained with an APC-conjugated 2C10 to assess the ability of each antibody to cross-block 2C10.

FIGS. 13a and 13b show sequence alignment of humanized 2C10 variable regions. FIG. 13a: Murine 2C10 VH sequence was aligned against human germline VH1-3 and three humanized sequences 2C10_h1, 2C10_h2, and 2C10_h3. FIG. 13b: Murine 2C10 VL sequence was aligned against human germline VH3-11 and two humanized sequences 2C10_l1 and 2C10_l2. The 2C10 CDRs are bolded. The murine residues in humanized sequences are underlined.

FIG. 14 shows amino acid changes in framework 3 between 2C10HP and 2C10HB1, as well as 2C10HB2 constructs.

FIG. 15 shows the sequences of heavy chain and light chain variable regions for humanized 2C10 antibodies. The heavy chain and light chain variable regions include 2C10HP, 2C10HB1, 2C10HB2, 2C10KP, 2C10KB1, and 2C10KB2.

Figure 16:
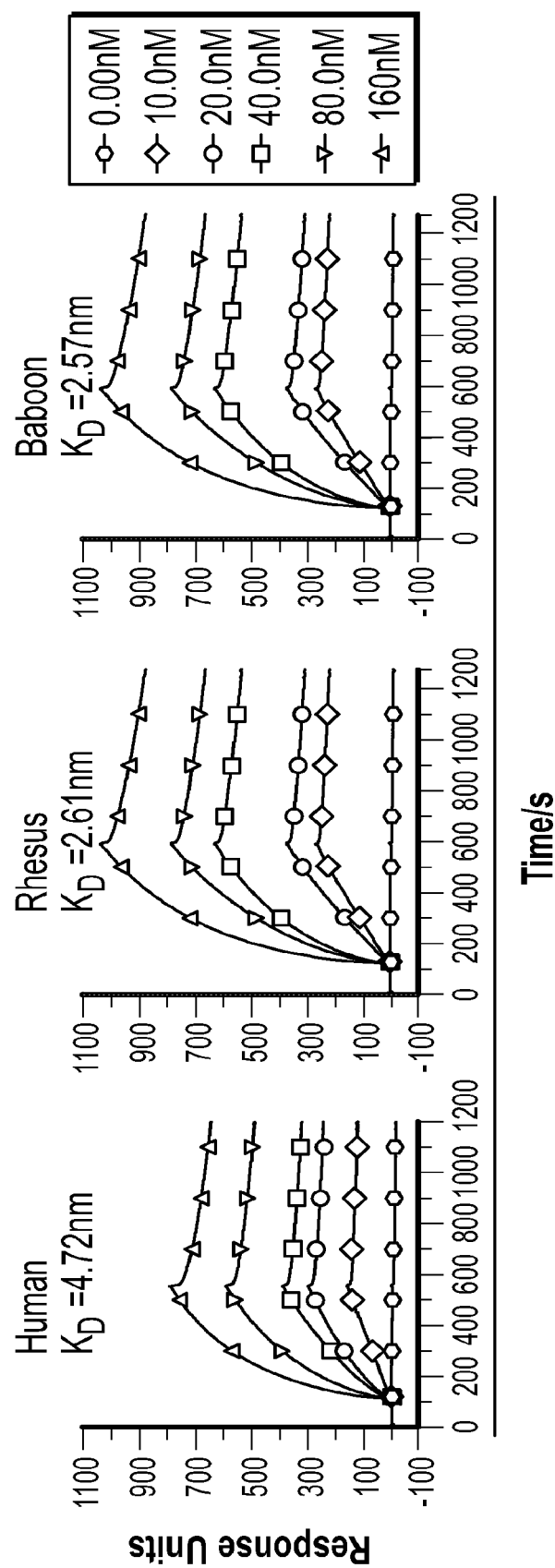

FIG. 16 shows binding affinity of humanized 2C10 antibody to CD40 from different primate species. Humanized 2C10 antibodies (h2C10) were immobilized to the surface of CM5 chip by amine coupling. Different concentrations of CD40-MBP fusions of human, rhesus, and baboon were analyzed for affinity on a BIACore 3000. The binding affinity was calculated with BIAevaluation software version 4.1.1.

Figure 17:
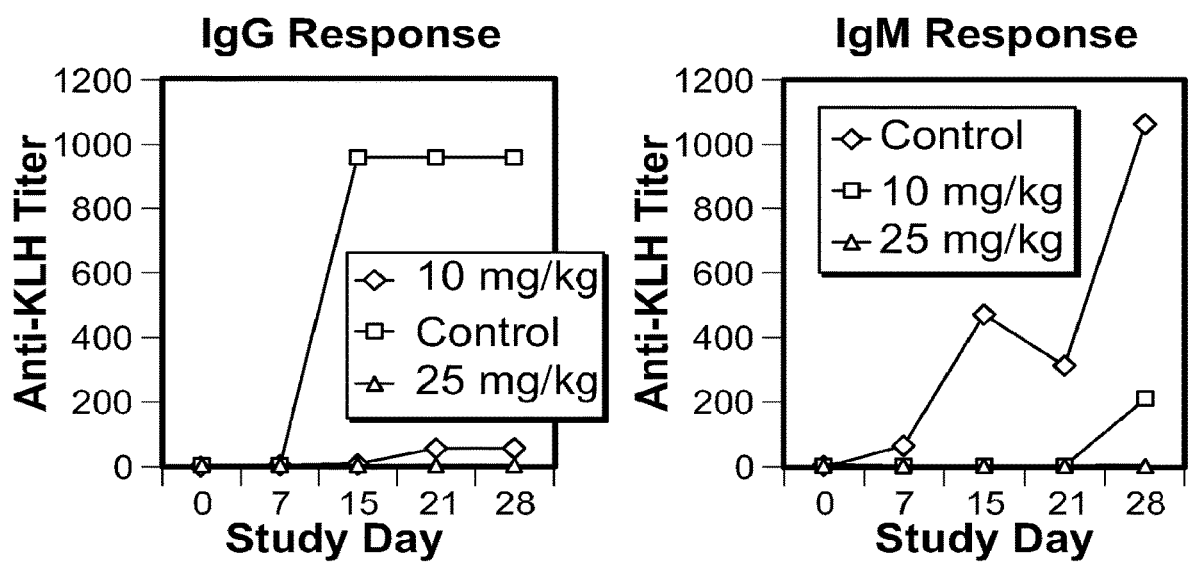

FIG. 17 shows that induction of anti-KLH antibody response (IgM and IgG) was determined in monkeys immunized with KLH 3 hrs after receiving either saline, 10 or 25 mg/kg h2C10. All control animals exhibited IgG or IgM antibody responses to the KLH antigen. Individual monkeys treated with 10 mg/kg, but no animals treated with 25 mg/kg 2C10 developed either an IgG or IgM antibody responses to KLH.

Figure 18:
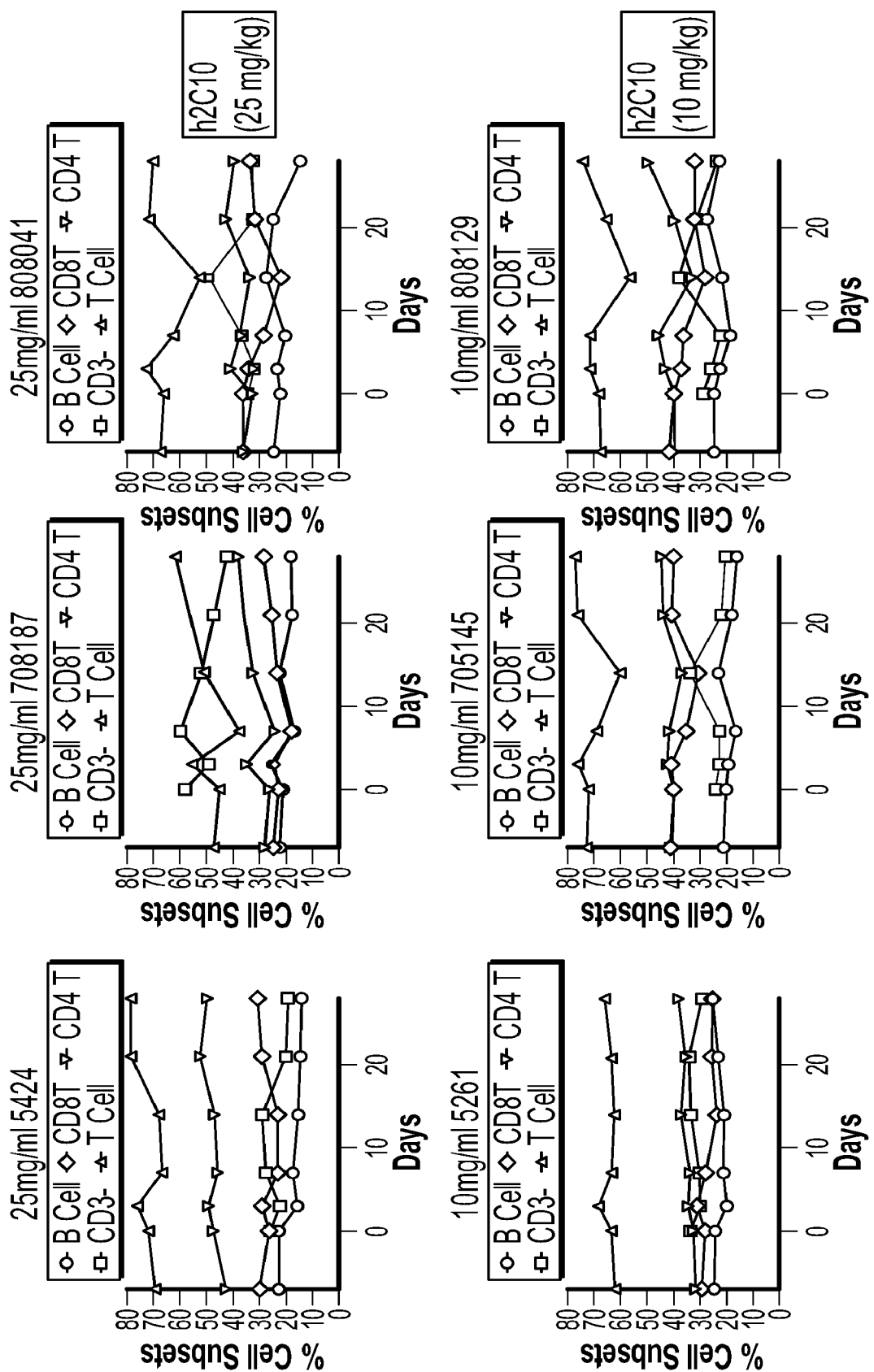
Figure 18:
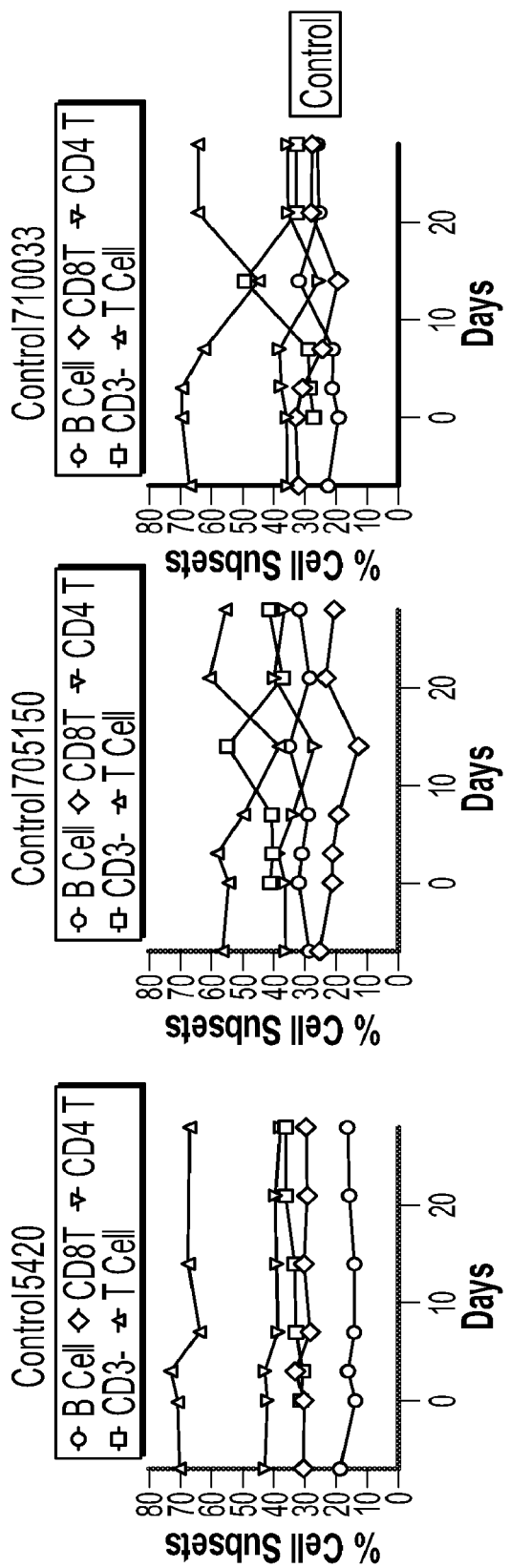

FIG. 18. Whole blood was used for phenotyping B and T lymphocyte subsets after treatment with 25 mg/kg h2C10 (Top row) or 10 mg/kg h2C10 (Middle row), or control animals (Bottom Row). Neither dose of h2C10 had any apparent effect on the lymphocyte populations. The absence of appreciable B cell depletion was also evident in the earlier, dose-response evaluation of the primate chimeric form that included a detailed analysis of mature and immature B cell populations.

Figure 19:
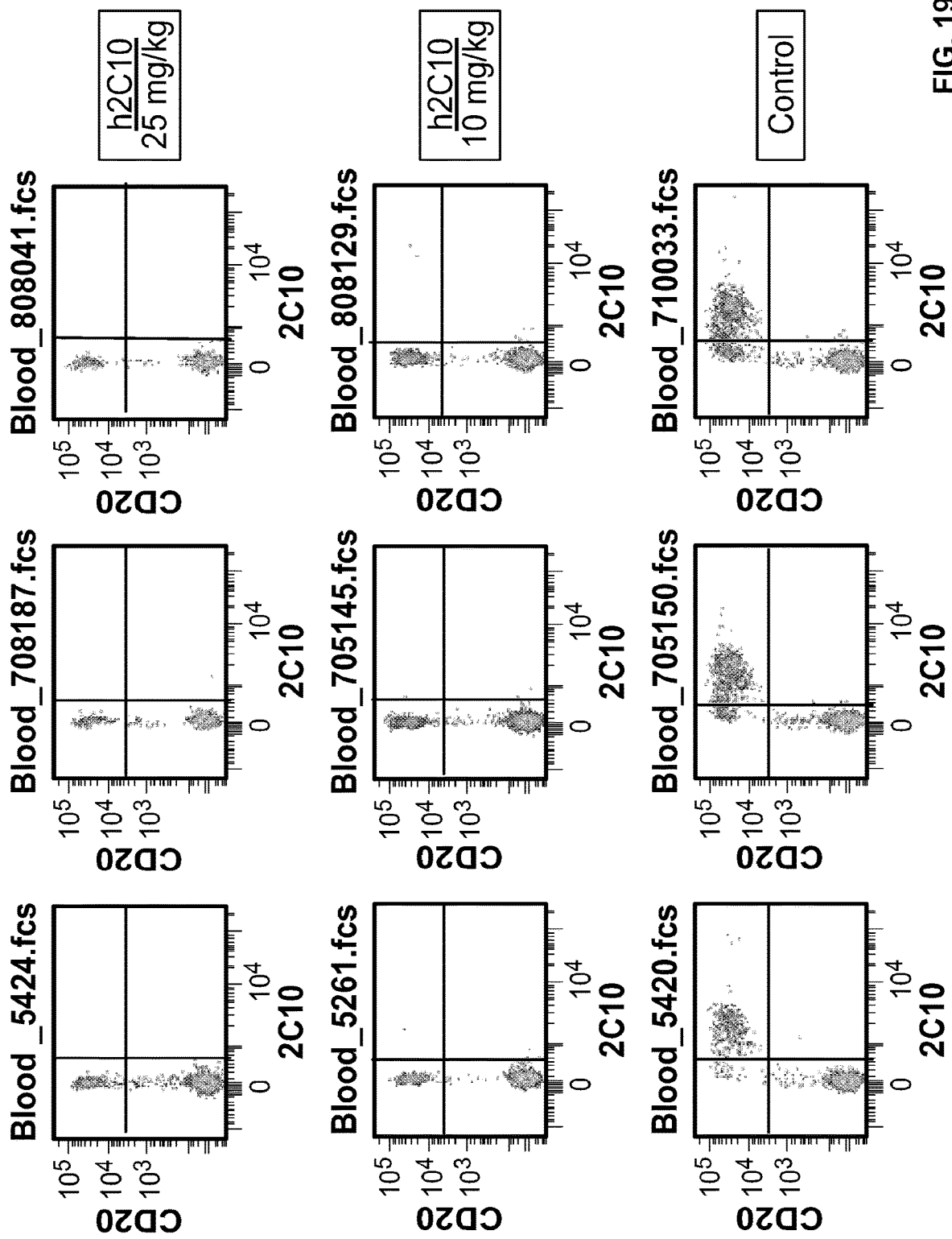

FIG. 19. Day 28 Humanized 2C10 fully saturated CD40 binding sites on B cells. H2C10 administered in vivo completely blocked the binding of fluorescently labeled 2C10 binding to B cells. Data illustrate results from humanized 2C10-treated and control monkeys 28 days after a single dose of 25 mg/kg (top row), 10 mg/kg (middle row) or 0 mg/kg (control, bottom row). Similar results were obtained on Days 3, 7, 14, and 21 post infusion.

Figure 20:
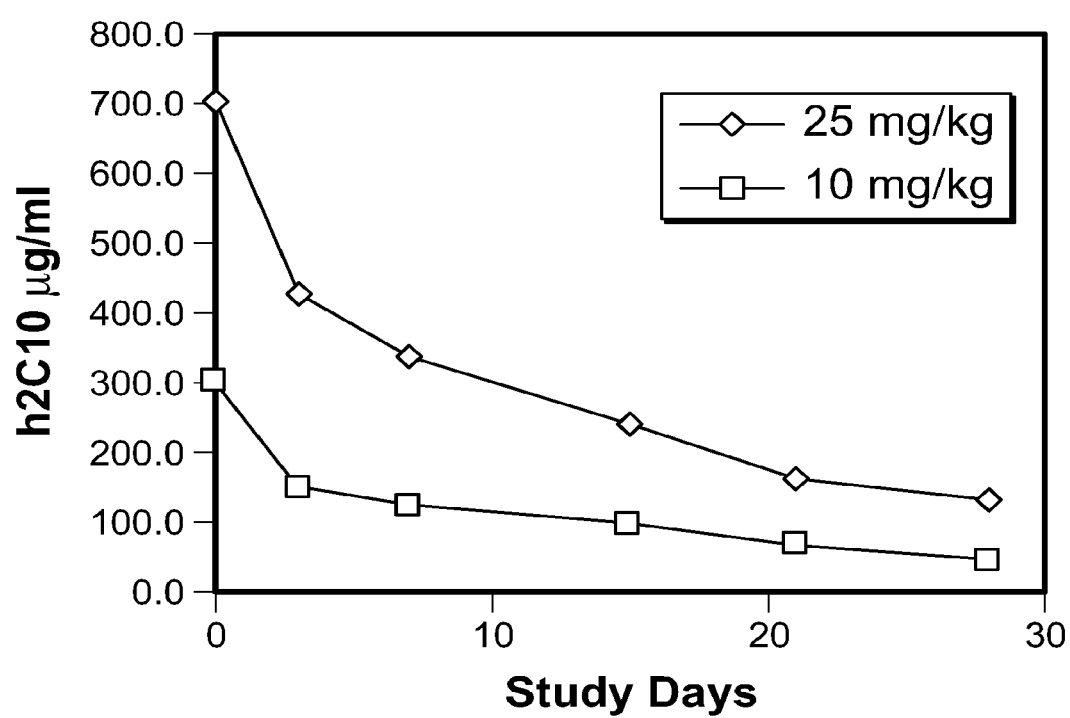

FIG. 20. Mean serum concentrations of h2C10 for up to 28 days after treatment of monkeys with either 10 or 25 mg/kg. Concentrations of 2C10 slowly decline over time, and levels are detected over the entire duration of the study.

FIGS. 21a and 21b show the DNA and amino acid sequences of the humanized 2C10 (h2C10) in the stabilized IgG4 format. FIG. 21a shows the DNA and amino acid sequences of the heavy chain. FIG. 21b shows the DNA and amino acid sequences of the light chain SEQ ID NO: 32: DNA sequence of the heavy chain; SEQ ID NO: 33; amino acid sequence of the heavy chain, SEQ ID NO: 34; DNA sequence of the light chain; SEQ ID NO: 35; amino acid sequence of the light chain.

DETAILED DESCRIPTION

The present disclosure relates to anti-CD40 antibodies and antibody fragments (e.g., antigen-binding portions of the antibody) that may be used in various therapeutic, prophylactic, diagnostic and other methods. The antibodies can block the ability of CD40 to bind CD154 and do so without activating the cell expressing CD40 (e.g., a B cell). The present antibodies or fragments thereof may be used so reduce complications associated with organ or tissue transplantation.

The antibodies, or antigen-binding portions thereof, include, but are not limited to, humanized antibodies, human antibodies, monoclonal antibodies, chimeric antibodies, polyclonal antibodies, recombinantly expressed antibodies, as well as antigen-binding portions of the foregoing. An antigen-binding portion of an antibody may include a portion of an antibody that specifically binds to CD40.

The present disclosure also provides for compositions and methods for reducing the likelihood of transplant rejection, treat transplant rejection, inducing immunosupression, and/or treating an autoimmune disorder. The compositions contain antibodies or fragments thereof that specifically bind CD40.

In one embodiment, the present disclosure provides for a method of treating or ameliorating graft-versus-host disease and/or transplant rejection in a subject comprising administering to the mammal a composition comprising an antibody of the invention (or its fragment) in an amount sufficient to decrease one or more of the symptoms of graft-versus-host disease and/or transplant rejection in the subject.

In another embodiment, the antibody or antigen-binding fragment is administered to a subject having an inflammatory disease or an immune disorder such as an autoimmune disease. The inflammatory disease or autoimmune disease may be associated with CD40-expressing cells.

The invention features methods of reducing the likelihood of transplant rejection, treat transplant rejection, inducing immunosuppression, and/or treating an autoimmune disorder in a subject by administering to the subject the present antibody or antigen-binding portion thereof in an effective amount.

Also encompassed by the present disclosure is a method, of blocking the function of CD40 in a mammal comprising administering to the mammal a composition comprising the present antibodies, or antigen-binding portions thereof, in an amount sufficient to block a CD40-mediated immune response in the mammal.

Another method of the disclosure relates to inhibiting the growth and/or differentiation of cells expressing CD40, comprising administering the present antibody or antigen-binding fragment to the cells, wherein the binding of the antibody or antigen-binding fragment to CD40 inhibits the growth and/or differentiation of the cells.

The present disclosure provides for a method of treating a subject having a CD40-associated disorder, comprising administering to the subject the present antibody or antigen-binding fragment, wherein the binding of the antibody or antigen-binding fragment to CD40 inhibits the growth and or differentiation of cells of the CD40-associated disorder. The cells may be, but are not limited to, B lymphoblastoid cells, pancreatic, lung cells, breast cells, ovarian cells, colon cells, prostate cells, skin cells, head and neck cells, bladder cells, bone cells or kidney cells.

The present method may be used to treat chronic lymphocytic leukemia, Burkitt's lymphoma, multiple myeloma, a T cell lymphoma, Non-Hodgkin's Lymphoma, Hodgkin's Disease, Waldenstrom's macroglobulmemia or Kaposi's sarcoma.

Additional methods of the present disclosure include inhibiting antibody production by B cells in a subject comprising administering to the subject, an effective amount of an anti-CD40 antibody or its fragment of the present disclosure. In one embodiment, the antibody is administered in an amount effective to inhibit B cell differentiation and antibody isotype switching in the subject. In another embodiment, the antibody is administered in an amount effective to inhibit cytokine and chemokine production, and/or inhibit up-regulation of adhesion molecules in T-cells and macrophages in the subject. In a third embodiment, the antibody is administered in an amount effective to inhibit activation of dendritic cells in the subject.

In addition to the present antibody or its fragment, the present methods may further comprise administering a second therapeutic agent such as an immunosuppressant, a tumor necrosis factor antagonist (a TNF-antagonist), a CTLA4-antagonist, an anti-IL-6 receptor antibody, an anti-CD20 antibody, or a combination thereof.

The present antibodies, or antigen-binding portions thereof, may specifically bind to human CD40 and/or rhesus CD40, including recombinant and native human CD40.

As used herein, a cell that expresses CD40 is any cell characterized by the surface expression of CD40, including, but not limited to, normal and neoplastic B cells, interdigitating cells, basal epithelial cells, carcinoma cells, macrophages, endothelial cells, follicular dendritic cells, tonsil cells, and bone marrow-derived plasma cells.

Humanized Antibodies

The humanized antibody of the present disclosure is an antibody from a non-human species where the amino acid sequences in the non-antigen binding regions (and/or the antigen-binding regions) have been altered so that the antibody more closely resembles a human antibody, and still retains its original binding ability.

An antibody light or heavy chain variable region consists of three hypervariable regions, referred to as complementarity determining regions (CDRs). CDRs are supported within the variable regions by framework regions (FRs). In one embodiment, the heavy chain variable region (or light chain variable region) contains three CDRs and four framework regions (FRs), arranged from amino-terminus to carboxyl-terminus in the following order: FR1, CDR1, FR2, CDR2, FR3, CDR3, FR4. Kabat, E. A., et al. Sequences of Proteins of Immunological Interest, Fifth Edition, U.S. Department of Health and Human Services. NIH Publication No. 91-3242, 1991. Chothia, C. el al., *J. Mol. Biol.* 196: 901-917, 1987.

In certain embodiments, humanized antibodies are antibody molecules from non-human species having one, two, three or all CDRs from the non-human species, and one, two, three, four or all framework regions from a human immunoglobulin molecule.

The CDRs of the present antibodies or antigen-binding portions thereof can be from a non-human or human source. The framework of the present antibodies or antigen-binding portions thereof can be human, humanized, non-human (e.g., a murine framework modified to decrease antigenicity in humans), or a synthetic framework (e.g., a consensus sequence). In one embodiment, the present antibodies, or antigen-binding portions thereof contain at least one heavy chain variable region and/or at least one light chain variable region.

The humanized antibodies of the present disclosure can be produced by methods known in the art. For example, a humanized antibody can have one or more amino acid residues introduced into it from a source which is non-human. These non-human amino acid residues are often referred to as "import" residues, which are typically taken from an "import" variable domain. Humanization can be performed following the method of Winter and co-workers (Jones et. al., *Nature* 321:522-5, 1986; Riechmann et. al., *Nature* 332:323-7, 1988; Verhoeyen et al., *Science* 239: 1534-6, 1988), by substituting hypervariable region sequences for the corresponding sequences of a human antibody. Accordingly, in such humanized antibodies substantially less than an intact human variable domain has been substituted by the corresponding sequence from a non-human species. In certain embodiments, humanized antibodies are human antibodies in which at least some hypervariable region residues as well as other variable region residues are substituted by residues from analogous sites in non-human antibodies.

The choice of human variable domains, both light and heavy, to be used in making the humanized antibodies, may reduce antigenicity. According to the "best-fit" method, the sequence of the variable domain of a non-human (e.g., rodent such as mouse) antibody is screened against the entire library of known human variable domain sequences, the human sequence which is closest to that of the non-human is then accepted as the human framework for the humanized antibody. See. e.g., Sims et al., *J. Immunol.* 151:2296-308, 1993; Chothia et. al., *J. Mol. Biol.* 196:901-17, 1987. Another method uses a particular framework derived from the consensus sequence of all human antibodies of a particular subgroup of light or heavy chains. The same framework may be used for several different humanized antibodies. See, e.g., Carter et al., *Proc. Natl. Acad. Sci. USA* 89:42855-9, 1992; Presta et al., *J. Immunol.* 151:2623-32, 1993.

Humanized antibodies can be generated by replacing sequences of the variable region that are not directly involved in antigen binding with equivalent sequences from human variable regions. Those methods include isolating, manipulating and expressing the nucleic acid sequences that encode all or part of variable regions from at least one of a heavy or light chain. Sources of such nucleic acid are well known to those skilled in the art and, for example, may be obtained from a hybridoma producing an antibody against CD40. The recombinant DNA encoding the humanized antibody, or fragment thereof, can then be cloned into an appropriate expression vector.

In another example, once non-human (e.g., murine) antibodies are obtained, variable regions can be sequenced, and the location of the CDRs and framework residues determined. Kabat, E. A., et. al. (1991) Sequences of Proteins of Immunological Interest, Fifth Edition, U.S. Department of Health and Human Services, NIH Publication No. 91-3242. Chothia, C. et. al. (1987) *J. Mol. Biol.,* 196:901-917. The light and heavy chain variable regions can, optionally, be ligated to corresponding constant regions. CDR-grafted antibody molecules can be produced by CDR-grafting or CDR substitution. One, two, three or all CDRs of an immunoglobulin chain can be replaced. For example, all of the CDRs of a particular antibody may be from at least a portion of a non-human animal (e.g., mouse such as CDRs shown in Table 1) or only some of the CDRs may be replaced. It is only necessary to keep the CDRs required for binding of the antibody to a predetermined antigen (e.g., CD40). Morrison, S. L., 1985, Science, 229:1202-1207. Oi et al., 1986, BioTechniques, 4:214. U.S. Pat. Nos. 5,585,089, 5,225,539, 5,693,761 and 5,693,762. EP 519596. Jones et al. 1986, Nature, 321:552-525. Verhoeyan et. al., 1988, Science, 239:1534. Beidler et al., 1988, J. Immunol., 141:4053-4060.

It may be desirable that antibodies be humanized with retention of high affinity for the antigen and other favorable biological properties. To achieve this goal, according to one method, humanized antibodies are prepared by a process of analysis of the parental sequences find various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic such as increased affinity for the target antigen(s), is achieved.

In some embodiments, a humanized anti-CD40 antibody also includes at least a portion of an immunoglobulin constant region, typically that of a human immunoglobulin. In one embodiment, the antibody will contain both the light chain as well as at least the variable domain of a heavy chain. The antibody also may include one or more of the constant domain CH1, hinge, CH2, CH3, and/or CH4 of the heavy chain, as appropriate.

In some aspects of the present disclosure, one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-CD40 antibody in prokaryotic and eukaryotic host cells.

Also encompassed by the present disclosure are antibodies, or antigen-binding portions thereof, containing one, two, or all CDRs as disclosed herein, with the other regions replaced by sequences from at least one different species including, but not limited to, human, rabbits, sheep, dogs, cats, cows, horses, goats, pigs, monkeys, apes, gorillas, chimpanzees, ducks, geese, chickens, amphibians, reptiles and other animals.

Human Antibodies

Human antibodies of the disclosure can be constructed by combining Fv clone variable domain sequencers selected from human-derived phage display libraries with known human constant domain sequencer(s) (Hoogenboom et al., *J. Mol. Biol* 227:381-8, 1992; Marks et al., *J. Mol. Biol* 222:581-97, 1991). Alternatively, human antibodies can be made by the hybridoma method. Human myeloma and mouse-human heteromyeloma cell lines for the production of human monoclonal antibodies have been described, for example, by Kozbor, *J. Immunol.* 133:3001-5, 1984, Brodeur et al., *Monoclonal Antibody Production Techniques and Applications*, pp. 51-63 (Marcel Dekker, Inc., New York. 1987): and Boerner et al., *J. Immunol.* 147:86-95, 1991.

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining legion (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See. e.g. Jakobovits et al., *Proc. Natl. Acad. Sci. USA* 90:2551-5, 1993: Jakobovits et al., *Nature* 362:255-8, 1993; Brüggemann et al., *Year Immunol.* 7:33-40, 1993.

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab where the human chain restores the antigen binding site destroyed upon removal of the corresponding non-human chain in the primary phage display clone, i.e., the epitope governs (imprints) the choice of the human chain partner. When the process is repeated in order to replace the remaining non-human chain, a human antibody is obtained (see PCT Publication WO 93/06213). Unlike traditional humanization of non-human antibodies by CDR grafting, this technique provides completely human antibodies, which have no FR or CDR residues of non-human origin.

Chimeric Antibodies

A chimeric antibody is a molecule in which different portions are derived from different animal species. For example, an antibody may contain a variable region derived from a murine antibody and a human immunoglobulin constant region. Chimeric antibodies can be produced by recombinant DNA techniques. Morrison, et al., Proc Natl Acad Sci, 81:6851-6855 (1984). For example, a gene encoding a murine (or other species) monoclonal antibody molecule is digested with restriction enzymes to remove the region encoding the murine Fc, and the equivalent portion of a gene encoding a human Fc constant region is substituted. Chimeric antibodies can also be created by recombinant DNA techniques where DNA encoding murine V regions can be ligated to DNA encoding the human constant regions. Better et al., Science. 1988, 240:1041-1043, Liu et al. PNAS, 1987 84:3439-3443. Liu et al., J. Immunol., 1987, 139:3521-3526. Sun et al. PNAS, 1987, 84:214-218. Nishimura et al., Canc. Res., 1987, 47:999-1005. Wood et al. Nature, 1985, 314:446-449. Shaw et al., J. Natl. Cancer Inst., 1988, 80:1553-1559. International Patent Publication Nos. WO1987002671 and WO 86/01533. European Patent Application Nos. 184, 187; 171,496; 125,023; and 173,494. U.S. Pat. No. 4,816,567.

Variable Regions and CDRs

The heavy chain variable regions, light chain variable regions and CDRs of the murine 2C10 antibody and certain humanized anti-CD40 antibodies, are shown in Table 1.

| Name | Chain, Region | Sequence | SEQ ID NO. |
|---|---|---|---|
| 2C10 (Murine antibody) | Heavy chain, variable region | QVQLQQSGAELAKPGASVKMSCKASG<u>YTFT NYWMH</u>WVKQRPGQGLEWIG<u>YINPSNDYTKY NQKFKD</u>KATLTADKSSNTAYMQLGSLTSEDS AVYYCAR<u>QGFPY</u>WGQGTLVTVSA | 11 |
| 2C10 | Light chain, variable region | QIVLTQSPAIMSASPGEKVTMTC<u>SASSSVSYM HWYH</u>QRSGTSPKRWIY<u>DTSKLAS</u>GVPARFSG SGSGTSYSLTISSMEAEDAATYYC<u>HQLSSDPF TF</u>GSGTKLEIK | 12 |
| 2C10 | Heavy chain, CDR1 | YTFTNYWMH | 13 |
| 2C10 | Heavy chain, CDR2 | YINPSNDYTKYNQKFKD | 14 |
| 2C10 | Heavy chain, CDR3 | QGFPY | 15 |
| 2C10 | Light chain, CDR1 | SASSSVSYMH | 16 |
| 2C10 | Light chain, CDR2 | DTSKLAS | 17 |
| 2C10 | Light chain, CDR3 | HQLSSDPFT | 18 |
| 2C10_h1 | Heavy chain, variable region | QVQLVQSGAEVKKPGASVKVSCKASG<u>YTFT NYWMH</u>WVRQAPGQRLEWMG<u>YINPSNDYTK YNQKFKD</u>RVTITRDTSASTAYMELSSLRSEDT AVYYCAR <u>QGFPY</u>WGQGTLVTVSS | 19 |
| 2C10_h2 | Heavy chain, variable region | QVQLVQSGAEVKKPGASVKVSCKASG <u>YTFTNYWMH</u> WVRQAPGQRLEWMG <u>YINPSNDYTKYNQKFKD</u> RVTITADKSASTAYMELSSLRSEDTAVYYCA R <u>QGFPY</u> WGQGTLVTVSS | 20 |
| 2C10_h3 | Heavy chain, variable region | QVQLVQSGAEVKKPGASVKVSCKASG <u>YTFTNYWMH</u> WVRQAPGQRLEWIG <u>YINPSNDYTKYNQKFKD</u> RATLTADKSANTAYM ELSSLRSEDTAVYYCAR <u>QGFPY</u> WGQGTLVTVSS | 21 |
| 2C10_l1 | Light chain, variable region | EIVLTQSPATLSLSPGERATLSC <u>SASSSVS YMH</u> WYQQKPGQAPRLLIY <u>DTSKLAS</u> GIPARFSGSGSGTDFTLTISSLEPEDFAVYYC <u>HQLSSDPFT</u> FGGGTKVEIK | 22 |
| 2C10_l2 | Light chain, variable region | EIVLTQSPATLSLSPGERATLSC <u>SASSSVSYMH</u> WYQQKPGQAPRRWIY <u>DTSKLAS</u> GVPARFSGSGSGTDYTLTISSLEPEDFAVYYC <u>HQLSSDPFT</u> FGGGTKVEIK | 23 |
| 2C10HP | Heavy chain, variable region | QVQLVQSGAEVKKPGASVKVSCKASG<u>YTFT NYWMH</u>WVRQAPGQRLEWIG<u>YINPSNDYTKY NQKFKD</u>RATLTADKSANTAYMELSSLRSEDT AVYYCAR<u>QGFPY</u>WGQGTLVTVSS | 24 |
| 2C10HB1 | Heavy chain, variable region | QVQLVQSGAEVKKPGASVKVSCKASG<u>YTFT NYWMH</u>WVRQAPGQRLEWIG<u>YINPSNDYTKY NQKFKD</u>RATLTADT STNTAYMELSSLRSEDT AVYYCAR<u>QGFPY</u>WGQGTLVTVSS | 25 |
| 2C10HB2 | Heavy chain, variable region | QVQLVQSGAEVKKPGASVKVSCKASG<u>YTFTN YWMH</u>WVRQAPGQGLEWIG<u>YINPSNDYTKYN QKFKD</u>KATITADESTNTAYMELSSLRSEDTA VYYCAR<u>QGFPY</u>WGQGTLVTVSS | 26 |
| 2C10KP | Light chain, variable region | EIVLTQSPATLSLSPGERATLSC<u>SASSSVSYMH</u> WYQQKPGQAPRRWIY<u>DTSKLAS</u>GVPARFSGS GSGTDYTLTISSLEPEDFAVYYC<u>HQLSSDPFT</u>F GGGTKVEIK | 27 |

| Name | Chain, Region | Sequence | SEQ ID NO. |
|---|---|---|---|
| 2C10KB1 | Light chain, variable region | DIQMTQSPSTLSASVGDRVTITCSASSSVSYM HWYQQKPGKAPKLLIYDTSKLASGVPARFSG SGSGTEFTLTISSLQPDDFATYYCHQLSSDPFT FGQGTKVEVK | 28 |
| 2C10KB2 | Light chain, variable region | EIVLTQSPATLSLSPGERATLSCSASSSVSYMH WYQQKPGQAPRLLIYDTSKLASGIPARFSGSG SGTDFTLTISSLEPEDFAVYYCHQLSSDPFTFG QGTKLEIK | 29 |
| VH1-3 | Heavy chain, variable region | QVQLVQSGAEVKKPGASVKVSCKASGYTFTS YAMHWVRQAPGQRLEWMGWINAGNGNTK YSQKFQGRVTITRDTSASTAYMELSSLRSEDT AVYYCARWGQGTLVTVSS | 30 |
| VK3-11 | Light chain, variable region | EIVLTQSPATLSLSPGERATLSCRASQSVSSYL AWYQQKPGQAPRLLIYDASNRATGIPARFSG SGSGTDFTLTISSLEPEDFAVYYCFGGGTKVEI K | 31 |

In certain embodiments the antibodies or antigen-binding portions thereof include a heavy chain variable region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a heavy chain variable region amino acid sequence as set forth in any of SEQ ID NOs: 11, 19, 20, 21, 24, 25 and 26.

In certain embodiments, the antibodies or antigen-binding portions thereof include a light chain variable region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to a light chair, variable region amino acid sequence as set forth in any of SEQ ID NOs 12, 22, 23, 27, 28 and 29.

In certain embodiments, the antibodies or antigen-binding portions thereof each include both a heavy chain variable region comprising an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to a heavy chain variable region amino acid sequence as set forth in any of SEQ ID NOs: 11, 19, 20, 21, 24, 25 and 26, and a light chain variable region including an amino acid sequence at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87, about 88%, about 89%, about 90%, about 91%, about 92%, about 93%, about 94%, about 95%, about 96%, about 97%, about 98%, about 99% or about 100% identical to a variable light chain amino acid sequence as set forth in SEQ ID NOs: 12, 22, 23, 27, 28 and 29.

A heavy chain variable region of the antibodies or antigen-binding portions thereof can comprise one, two, three or more complementarity determining regions (CDRs) that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to the CDRs of a heavy chain variable region of the 2C10 antibody (CDR1, CDR2 and CDR3 as set forth in SEQ ID NOs: 13, 14, 15, respectively).

A light chain variable region of the antibodies or antigen-binding portions thereof can comprise one, two, three or more CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to the CDRs of a light chain variable region of the 2C10 antibody (CDR1, CDR2 and CDR3 as set forth in SEQ ID NOs 16, 17, 18, respectively).

A heavy chain variable region of the present antibodies, or antigen-binding portions thereof can comprise one, two, three or more complementarity determining regions (CDRs) that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to the CDRs of a heavy chain variable region of the 2C10 antibody (CDR1, CDR2 and CDR3 as set forth in SEQ ID NOs: 13, 14, 15, respectively), and a light chain variable region of the antibodies or antigen-binding portions thereof can comprise one, two, three or more CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 04%, about 95%, about 96%, about 97%, about 98%, about 99% or about 100% identical to the CDRs of a light chain variable region of the 2C10 antibody (CDR1, CDR2 and CDR3 as set forth in SEQ ID NOs. 16, 17, 18, respectively.

A heavy chain variable region of the antibodies or antigen-binding portions thereof can include three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to the CDRs of a heavy chain variable region of the 2C10 antibody (CDR1, CDR2 and CDR3 as set forth in SEQ ID NOs: 13, 14, 15, respectively).

In one embodiment, a light chain variable region of the antibodies or antigen-binding portions thereof includes three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the CDRs of a light chain variable region of the 2C10 antibody (CDR1, CDR2 and CDR3 as set forth in SEQ ID NOs: 16, 17, 18 respectively).

In one embodiment, a heavy chain variable region of the antibodies or antigen-binding portions thereof includes three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 97%, about 98%, about 99% or about 100% identical to the CDRs of a heavy chain variable region of the 2C10 antibody (CDR1, CDR2 and CDR3 as set forth in SEQ ID NOs: 13, 14, 15, respectively), and a light chain variable region of the antibodies or antigen-binding portions thereof includes three CDRs that are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to the CDRs of a light chain variable region of the 2C10 antibody (CDR1, CDR2 and CDR3 as set forth in SEQ ID NOs: 16, 17, 18, respectively).

In certain embodiments, a heavy chain variable region of the antibodies or antigen-binding portions thereof includes three CDRs that are identical to CDRs of a heavy chain variable region of the 2C10 antibody (CDR1, CDR2 and CDR3 as set forth in SEQ ID NOs: 13, 14, 15, respectively), and a light chain variable region of the antibodies or antigen-binding portions thereof includes three CDRs that are identical to CDRs of a light chain variable region of the 2C10 antibody (CDR1, CDR2 and CDR3 as set forth in SEQ ID NOs: 16, 17, 18, respectively).

Encompassed by the present disclosure are antibodies with a heavy chain variable region and a light chain variable region having amino acid sequences at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about about 93%, about 94%, about 95%, about 96%, about 97%, about 98%, about 99%, or about 100%, identical to the heavy chain variable region (SEQ ID NO: 11) and light chain variable region (SEQ ID NO: 12) of the antibody 2C10, respectively.

In related embodiments, anti-CD40 antibodies or antigen-binding portions thereof include, for example, the CDRs of heavy chain variable regions and/or light chain variable regions of 2C10.

In one embodiment, the antibody or antigen-binding portion thereof contains a heavy chain variable region and a light chain variable region identical to a heavy chain variable region and light chain variable region of the 2C10 antibody (SEQ ID NO: 11 and SEQ ID NO: 12, respectively).

In various embodiments, the antibodies or antigen-binding portions thereof specifically bind to an epitope that overlaps with, or are at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100%, identical to an epitope bound by the 2C10 antibody. The epitope may be present within the sequence of SEQ ID NO: 6, or may be present within the sequence of amino acids 8-40 of SEQ ID NO: 6.

In certain embodiments, CDRs corresponding to the CDRs in Table 1 have sequence variations. For example, CDRs, in which 1, 2, 3, 4, 5, 6, 7 or 8 residues, or less than 20%, less than 30%, or less than about 40%, of total residues in the CDR, are substituted or deleted can be present in an antibody for antigen-binding portion thereof) that binds CD40.

Also within the scope of the disclosure are antibodies or antigen-binding portions thereof in which specific amino acids have been substituted, deleted or added. These alternations do not have a substantial effect on the peptide's biological properties such as binding activity. For example, antibodies may have amino acid substitutions in the framework region, such as to improve binding to the antigen. In another example, a selected small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247; 1306-1310 (1990). Cunningham et al., Science, 244; 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243: 307-31 (1994). Gonnet et al., Science 256: 1443-45 (1992).

The present peptides may be the functionally active variant of antibodies of antigen-binding portions thereof disclosed herein, e.g., with less than about 30%, about 25%, about 20%, about 15%, about 10%, about 5% or about 1% amino acid residues substituted or deleted but retain essentially the same immunological properties including, but not limited to, binding to CD40.

The antibodies or antigen-binding portions thereof may also include variants, analogs, orthologs, homologs and derivatives of peptides, that exhibit a biological activity, e.g., binding of an antigen such as CD40. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, an immunosuppressant, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. Cytotoxic agents may include radioactive isotopes, chemotherapeutic agents, and toxins such as enzymatically active toxins of bacterial, fungal, plant, or animal origin, and fragments thereof. Such cytotoxic agents can be coupled to the humanized antibodies of the present disclosure using standard procedures, and used, for example, to treat a patient indicated for therapy with the antibody.

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) homobifunctional (e.g., disuccinimidyl substrate). Useful detectable agents with which a protein can be derivatized (or labeled) include fluorescent agents, various enzymes, prosthetic groups, luminescent materials, bioluminescent materials, and radioactive materials. Non-limiting, exemplary fluorescent detectable agents include fluorescein, fluorescein isothiocyanate, rhodamine, and phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

In another embodiment, the humanized anti-CD40 antibody or its fragment is used unlabeled and detected with a labeled antibody that binds the humanized anti-CD40 antibody or its fragment.

Antibody Fragments

The antibodies can be full-length or can include a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by The present disclosure. Bird et al. Science, 1988, 242:423-426. Huston et al., Proc. Natl. Acad. Sci. USA, 1988, 85:5879-5883.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

Fv is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation for Fab' in which the cysteine residue(s) of the constant domains bear a free thiol group. F(ab')$_2$ antibody fragments originally were produced as pairs of Fab' liagments which have hinge cysteines between them. Other chemical couplings of antibody fragments are also known.

Single-chain Fv or scFx antibody fragments comprise the $V_H$ and $V_L$ domains of antibody, where these domains are present in a single polypeptide chain. Generally, the scFv polypeptide further comprises a polypeptide linker between the $V_H$ and $V_L$ domains which enables the scFv to form the desired structure for antigen binding. For a review of scFv, see, e.g., Pluckthün, in *The Pharmacology of Monoclonal Antibodies*, vol. 113, Roseuburg and Moore, eds., (Springer-Verlag, New York, 1904). pp 269-315

Diabodies are antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, European Patent No. 404,097; PCT Publication WO 1993/01161; Hudson et al., *Nat. Med.* 9:129-34, 2003; and Hollinger et al., *Proc. Natl. Acad. Sci. USA* 90:6444-8, 1993. Triabodies and tetrabodies are also described in Hudson et al., *Nat. Med.* 9:129-34, 2003.

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. *Nat. Med.* 9:129-134, 2003.

Various techniques have been developed for the production of antibody fragments. Traditionally these fragments were derived via proteolytic digestion of intact antibodies (see e.g., Morimoto et al., *J. Biochem. Biophys. Methods* 24:107-17, 1992; and Brennan et al., *Science* 229:81-3, 1985). However, these fragments can now be produced directly by recombinant host cells. Fab, Fv, and ScFv antibody fragments can all be expressed in and selected from *E. Coli*, thus allowing the facile production of large amounts of these fragments. Antibody fragments can be isolated from the antibody phage libraries. Alternatively Fab'-SH fragments can be directly recovered from *E. coli* and chemically coupled to form F(ab')$_2$ fragments (Carter et al., *Bio/Technology* 10:163-7, 1992). In another approach, F(ab')$_2$ fragments are isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner.

The present antibody or antigen-binding portion thereof may comprise at least one constant domain, such as, (a) an IgG constant domain; (b) an IgA constant domain, etc.

All antibody isotypes are encompassed by the present disclosure, including IgG (e.g., IgG1, IgG2, IgG3, IgG4), IgM, IgA, (IgA1, IgA2), IgD or IgE. The antibodies or antigen-building portions thereof may be mammalian (e.g., mouse, human) antibodies or antigen-binding portions thereof. The light chains of the antibody may be of kappa or lambda type. An alternative humanized anti-CD40 antibody can comprise sequences from more than one immunoglobulin class or isotype, and selecting particular constant domains to optimize desired effector functions is within the ordinary skill in the art.

The antibodies or antigen-binding portions thereof of The present disclosure may be monospecific, bi-specific or multi-specific. Multi-specific or bi-specific antibodies or fragments thereof may be specific for different epitopes of one target polypeptide (e.g., CD40) or may contain antigen-binding domains specific for more than one target polypeptide (e.g., antigen-binding domains specific for CD40 and other antigen relating to transplant rejection or autoimmune disease). In one embodiment, a multispecific antibody or antigen-binding portion thereof comprises at least two different variable domains, wherein each variable domain is capable of specifically binding to a separate antigen or to a different epitope on the same antigen. Tutt et al., 1991, J. Immunol. 147:60-69. Kufer et al., 2004. Trends Biotechnol 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for CD40, and she other arm of the immunoglobulin is specific for a second therapeutic target or is conjugated to a therapeutic moiety such as an immunosuppressant.

Production of Antibodies

The present disclosure provides for methods for making an antibody or antigen-binding portion thereof that specifically binds to CD40.

For example, a non-human animal is immunized with a composition that includes CD40, and then a specific antibody is isolated from the animal. The method can further include evaluating binding of the antibody to CD40.

In one embodiment, the present disclosure provides for a method for making a hybridoma that expresses an antibody that specifically binds to CD40. The method contains the following steps: immunizing an animal with a composition that includes CD40 or its fragment, isolating splenocytes from the animal, generating hybridomas from the splenocytes; and selecting a hybridoma that produces an antibody that specifically binds to CD40. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

In one embodiment, CD40 is used to immunize mice intraperitoneally or intravenously. One or more boosts may or may not be given. The titers of the antibodies in the plasma can be monitored by, e.g., ELISA (enzyme-linked immunosorbent assay) or flow cytometry. Mice with sufficient titers of anti-CD40 antibodies are used for fusions. Mice may or may not be boosted with antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-CD40 monoclonal antibodies. The antibody secreting hybridomas are replated, screened again, and if still positive for anti-CD40 monoclonal antibodies, can be subcloned by limiting dilution.

Adjuvants that may be used to increase the immunogenicity of CD40 include any agent or agents that act to increase an immune response to peptides or combination of peptides. Non-limiting examples of adjuvants include alum, aluminum phosphate, aluminum hydroxide, MF59 (4.3% w/v squalene, 0.5% w/v polysorbate 80 (Tween 80), 0.5% w/v sorbitan trioleate (Span 85)). CpG-containing nucleic acid, QS21 (saponin adjuvant), MPL (Monophosphoryl Lipid A), 3DMPL (3-O-deacylated MPL) extracts from Aquilla, ISCOMS (see, e.g., Sjolander et al. (1998) J. Leukocyte Biol. 64:713; WO09/03184; WO96/11711; WO 00/48630; WO98/36772; WO00/41720; WO06/134423 and WO07/026190), LT/CT mutants, poly(D,L-lactide-co-glycolide) (PLG) microparticles, Quil A., interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

The immunized animal can be any animal that is capable of producing recoverable antibodies when administered an immunogen, such as, but not limited to, rabbits, mice, rats, hamsters, goats, horses, monkeys, baboons and humans. In one aspect, the host is transgenic and produces human antibodies, e.g., a mouse expressing the human immunoglobulin gene segments. U.S. Pat. No. 8,236,311; 7,625,559 and 5,770,429, the disclosure of each of which is incorporated herein by reference in its entirety. Lonberg et al., Nature 368(6474): 856-859, 1994. Lonberg, N., Handbook of Experimental Pharmacology 113:49-101, 1994. Lonberg, N. and Huszar, D. Intern. Rev. Immunol. 13: 65-93, 1995 Harding, F. and Lonberg N., Ann. N.Y. Acad. Sci., 764:536-546, 1995.

The present antibodies or portions thereof can be produced by host cells transformed with DNA encoding light and heavy chains (or portions thereof) of a desired antibody. Antibodies (or portions thereof) can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding at least a portion of either or both of the light and heavy chains that is not necessary for binding, e.g., the constant region.

The invention also encompasses a nucleic acid or polynucleotide encoding at least one of the present antibody or antigen-binding portion thereof that specifically binds to CD40. The nucleic acid may be expressed in a cell to produce the present antibody or antigen-binding portion thereof. The isolated nucleic acid or polynucleotide of the present disclosure comprises at least one sequence encoding a peptide at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to any of SEQ ID NOs: 11-29.

The invention also features expression vectors including at least one nucleic acid or polynucleotide encoding a peptide at least about 70%, at least about 75%, at least about 80%, at least about 85%, at least about 90%, at least about 95%, at least about 99%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical to any of SEQ ID NOs: 11-29.

Nucleic acid molecules encoding a functionally active variant of the present antibody or antigen-binding portion thereof are also encompassed by the present disclosure. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: (1) medium stringency hybridization conditions: 6×SSC at about 45° C., followed by one or more washes in 0.2×SSC, 0.1% SDS at 60° C.; (2) high stringency hybridization conditions: 6×SSC at about 45° C., followed by one or more washes in 0.2×SSC, 0.1% SDS at 65° C.; and (3) very high stringency hybridization conditions; 0.5 M sodium phosphate, 7% SDS at 65° C. followed by one or more washes at 0.2×SSC, 1% SDS at 65° C.

A nucleic acid or polynucleotide encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al., Proc Natl Acad Sci USA, 86; 10029-10033 (1989).

The present nucleic acids can be expressed in various suitable cells, including prokaryotic and eukaryohc cells, e.g., bacterial cells, (e.g., $E.$ $coli$), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g. COS-1, COS-7), HEK293, baby hamster kidney (BHK, e.g., BHK21), Chinese hamster ovary (CHO), NS0, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present disclosure also provides for cells comprising the nucleic acids described herein. The cells may be a hybridoma or transfectant. The present antibody or antigen-binding portion thereof can be expressed in various cells. The types of the cells are discussed herein.

When using recombinant techniques to produce, e.g. the humanized antibody or the antigen-binding portion thereof, the antibody or its portion can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of $E.$ $coli.$ Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems may be first concentrated using a commercially available protein concentration filter, for example, an Amicon or Millipore Pellicon ultrafiltration unit. A variety of methods can be used to isolate the antibody from the host cell.

The antibody or its portion prepared from the cells can be purified using, for example, hydroxylapalite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see. e.g., Lindmark et al., 1983 J. Immunol. Meth. 62:1-13). Protein G is recommended for all mouse isotypes and for human gamma3 (see, e.g., Guss et al, 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elation buffer at a pH between about 2.5-4.5, typically performed at low salt concentrations (e.g., from about 0-0.25M salt).

Hybridomas or other cells that produce antibodies that bind, preferably with high affinity, to CD40 can then be subcloned and further characterized. One clone from each hybridoma or cell, which retains the reactivity of the parent cells (by ELISA), can then be chosen for making a cell bank, and for antibody purification.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989) Methods in Molecular Biology, Vol 35: Peptide Synthesis Protocols (ed. M W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

Additional antibodies (e.g., monoclonal polyclonal, polyspecific, or monospecific antibodies) against the CD40 epitope recognized by 2C10 can be made, e.g., using a suitable method for making antibodies. In an example, a coding sequence for an epitope recognized by the 2C10 antibody is expressed as a C-terminal fusion with glutathione S-transferase (GST) (Smith et al., Gene 67:31-40, 1988). The fusion protein is purified on glutathione-Sepharose beads, eluted with glutathione, cleaved with thrombin (at an engineered cleavage site), and purified for immunization of rabbits. Primary immunizations are carried out with Freund's complete adjuvant and subsequent immunizations with Freund's incomplete adjuvant. Antibody titers are monitored by Western blot and immunoprecipitation analyses using the thrombin-cleaved protein fragment of the GST fusion protein. Immune sera are affinity purified using CNBr-Sepharose-coupled protein. Antiserum specificity can be determined using a panel of unrelated GST proteins.

As an alternate or adjunct immunogen to GST fusion proteins, peptides corresponding to relatively unique immunogenic regions of a polypeptide of the invention can be generated and coupled to keyhole limpet hemocyanin (KLH) through an introduced C-terminal lysine. Antiserum to each of these peptides is similarly affinity purified on peptides conjugated to BSA, and specificity is tested by ELISA or Western blot analysis using peptide conjugates, or by Western blot or immunoprecipitation using the polypeptide expressed as a GST fusion protein.

Alternatively, monoclonal antibodies that specifically bind the CD-40 epitope recognized by the 2C10 antibody can be prepared using standard hybridoma technology (see, e.g., Kohler et al., Nature 256:495-7, 1975; Kohler et al., Eur. J. Immunol 6:511-9, 1976; Kohler et al., Eur. J. Immunol. 6:292-5, 1976, Hammerling et al., Monoclonal Antibodies and T Cell Hybridomas, Elsevier, N.Y., 1981). Once produced, monoclonal antibodies can also be tested for specific recognition by Western blot or immunoprecipitation analysis. Alternatively, monoclonal antibodies can be prepared using the polypeptide of the invention described above and a phage display library (Vaughan et al., Nat. Biotechnol. 14:309-14, 1996).

Epitopic fragments can be generated by standard techniques, e.g., using PCR and cloning the fragment into a pGEX expression vector. Fusion proteins are expressed in E. coli and purified using a glutathione agarose affinity matrix. To minimize potential problems of low affinity or specificity of antisera, two or three such fusions are generated for each protein, and each fusion is injected into at least two rabbits. Antisera are raised by injections in a series, and can include, for example, at least three booster injections.

In order to generate polyclonal antibodies on a huge scale and at a low cost an appropriate animal species can be chosen. Polyclonal antibodies can be isolated from the milk or colostrum of, e.g., immunized cows. Bovine colostrum contains 28 g of IgG per liter, while bovine milk contains 1.5 g of IgG per liter (Ontssouka et al., J. Dairy Sci. 86; 2005-11, 2003). Polyclonal antibodies can also be isolated from the yolk of eggs from immunized chickens (Sarker et al., J. Pediatr. Gastroenterol. Nutr. 32:19-25, 2001).

Assays

Various methods can be used to assay the antibodies or antigen-binding portions thereof to confirm their specificity for the antigen of interest and/or to study their properties. One method of conducting such assays is a sera screen assay as described in U.S. Patent Publication No. 2004/0126829. Anti-CD40 antibodies can be characterized for binding to CD40 by a variety of known techniques. For example, in an ELISA, microliter plates are coated with CD40 or a fragment of CD40 in PBS, and then blocked with irrelevant proteins such as bovine serum albumin (BSA) diluted in PBS. Dilutions of plasma from CD40-immunized mice (or solutions containing anti-CD40 antibodies) are added to each well and incubated. The plates are washed and then incubated with a secondary antibody conjugated to an enzyme (e.g., alkaline phosphatase). After washing, the plates are developed with the enzyme's substrate (e.g., ABTS), and analyzed at a specific OD. In other embodiments, to determine if the selected monoclonal antibodies bind to unique epitopes, the antibody can be biotinylated which can then be detected with a streptavidin labeled probe. Anti-CD40 antibodies can be tested for reactivity with CD40 by Western blotting.

Antibodies, or antigen-binding fragments, variants or derivatives thereof of the present disclosure can also be described or specified in terms of their binding affinity to an antigen. The affinity of an antibody for an antigen can be determined experimentally using any suitable method (see, e.g., Berzofsky et al., "Antibody-Antigen Interactions," In Fundamental Immunology, Paul W. E., Ed., Raven Press; New York, N. Y. (1984); Kuby, Janis Immunology, W. H. Freeman and Company: New York, N.Y. (1992), and methods described herein. The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The present antibodies or antigen-binding portions thereof specifically bind to CD40 with a dissociation constant of less than about $10^{-7}$ M, less than about $10^{-8}$ M, less than about $10^{-9}$ M, less than about $10^{-10}$ M, less than about $10^{-11}$ M, less than about $10^{-12}$ M, from about $10^{-7}$ M to about $10^{-12}$ M, from about $10^{-8}$ M to about $10^{-11}$ M, from about $10^{-9}$ to about $10^{-10}$ M, or from about $10^{-8}$ to about $10^{-12}$ M.

Assays may also be used to test the ability of an antibody (or its fragment) to block CD40 binding to CD154, or inhibit or decrease CD40-mediated responses.

As used herein, the terms "inhibits binding" and "blocks binding" (e.g., inhibition/blocking of binding of CD154 to CD40) are used interchangeably and encompass both partial and complete inhibition blocking. Inhibition and blocking are also intended to include any measurable decrease in the binding of CD154 to CD40 when in contact with an anti-CD40 antibody or portions thereof as disclosed herein as compared to ligand not in contact with an anti-CD40 antibody, e.g., the blocking of CD154 to CD40 by at least about 10%, 20%, 30%, 40%, 50%, 60%, 65%, 70%, 75%, 80%, 85%, 90%, 91%, 92%, 93%, 94%, 95%, 96%, 97%, 98%, 99% or 100%.

In one embodiment, activation of B cells, or inhibition thereof, may be determined by measuring expression of one or more markers selected from CD23, CD80, CD86, and any additional suitable marker on CD20+ cells.

The present antibodies or fragments thereof may be characterized by their effects on T cell-mediated antibody responses. For example, the antibodies or fragments thereof may inhibit IgM and/or IgG production in a mammal, when the antibody, or an antigen-binding portion thereof, is administered to the mammal at a dosage ranging from about 1 mg/kg body weight to about 50 mg/kg body weight, from about 2 mg/kg body weight to about 40 mg/kg body weight, from about 3 mg/kg body weight to about 30 mg/kg body weight, from about 5 mg/kg body weight, to about 20 mg/kg body weight, from about 8 mg/kg body weight to about 13 mg/kg body weight, about 1 mg/kg body weight, about 2 mg/kg body weight, about 5 mg/kg body weight, about 10 mg/kg body weight, about 15 mg/kg body weight, about 20 mg/kg body weight, about 25 mg/kg body weight, about 30 mg/kg body weight, about 35 mg/kg body weight, about 40 mg/kg body weight, about 50 mg/kg body weight, about 60 mg/kg body weight, about 70 mg/kg body weight, or about 80 mg/kg body weight.

The present antibodies or fragments thereof may be characterized by their effects on prolonging graft survival post transplantation. The present antibodies or fragments thereof, alone or in combination with one or more other immunosuppressants, may prolong graft survival by about 30%, about 40%, about 50%, about 60%, about 70%, about 80%, about 90%, about 2 fold, about 5 fold, about 10 fold, about 15 fold, about 20 fold, about 25 fold, about 30 fold, about 35 fold, about 40 fold, about 45 fold, about 50 fold, about 55 fold, greater than about 40%, greater than about 50%, greater than about 60%, greater than about 70%, greater than about 80%, or greater than about 00%, greater than about 2 fold, greater than about 5 fold, greater than about 10 fold, greater than about 20 fold, greater than about 30 fold, or greater than about 40 fold. For example, the present antibodies or fragments thereof may prolong islet allograft survival.

In certain embodiments, the present antibody, or antigen-binding fragment thereof: a) may block binding of CD40 to CD154; c) may block activation of antigen presenting cells (e.g., B cells, dendritic cells, macrophages, etc.); d) may or may not induce depletion of B cells; e) may or may not inhibit or decrease cytokine release from antigen presenting cells; f) may or may not induce tumor cell apoptosis, g) may or may not inhibit tumor cell proliferation; h) may or may not kills tumor cell; i) may or may not stimulate anti-tumor T cell responses; and/or j) may or may not reduce established tumors. The antibodies described herein may have or induce a combination of any one or more of these attributes or activities. Tai, et al., Cancer Res. 2005, 1; 65(13):5898-906; Luqman et al., Blood 112:711-720, 2008. The antibodies or portions thereof described herein may also be tested for effects on CD40 internalization, in vitro and in vivo efficacy, etc. Such assays may be performed using well-established protocols known to the skilled person (see e.g., Current Protocols in Molecular Biology (Greene Publ. Assoc, Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

Conditions to be Treated

The present antibodies or antigen-binding portions thereof have in vitro and in vivo therapeutic, prophylactic, and or diagnostic utilities. For example, cells can be cultured in vitro in culture medium and contacted by the anti-CD40 antibody or fragment thereof. The antibodies or antigen-binding portions thereof can be administered in a subject, as part of an in vivo (e.g., therapeutic or prophylactic) protocol. For in vivo embodiments, the contacting step is effected in a subject and includes administering an anti-CD40 antibody or portion thereof to the subject under conditions effective to permit binding of the antibody or portion thereof to CD40 in the subject. The antibodies or antigen-binding portions thereof can be administered to reduce the likelihood of, or increase the duration prior to, transplant rejection, inducing immunosuppression, or treating an autoimmune disorder.

The antibodies or antibody fragments described herein may be used in any situation in which immunosuppression is desired (e.g., transplant rejection or autoimmune disorders). These antibodies are particularly useful for treating transplant rejection e.g., reducing the likelihood that a particular transplant is rejected by the host or increasing the time before rejection takes place. The antibodies or antibody fragments described herein can be used in conjunction with transplantation of any organ or any tissue that is suitable for transplantation. Non-limiting exemplary organs include heart, kidney, lung, liver, pancreas, intestine, and thymus; non-limiting exemplary tissues include bone, tendon, cornea, skin, heart valve, vein, and bone marrow. The antibodies and antibody fragments can also be used to treat autoimmune disorders. In one embodiment, the autoimmune disorder may be associated with or caused by the presence of an autoantibody. Autoimmune diseases that may be treated with the present antibodies or fragments thereof include, but are not limited to, systemic lupus erythematosus (SLE), CREST syndrome (calcinosis, Raynaud's syndrome, esophageal dysmotility, sclerodactyl, and telangiectasia), opsoclonus, inflammatory myopathy (e.g., polymyositis, dermatomsositis, and inclusion-body myositis), systemic scleroderma, primary biliary cirrhosis, celiac disease (e.g., gluten sensitive enteropathy), dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis, Lambert-Eaton myasthenic syndrome, Hashimoto's thyroiditis, Graves' disease, Paraneoplastic cerebellar degeneration, Stiff person syndrome, limbic encephalitis, Isaacs Syndrome, Sydenham's chorea, pediatric autoimmune neuropsychiatric disease associated with Streptococcus (PAN- DAS), encephalitis, diabetes mellitus type 1, and Neuromyelitis optica. Other autoimmune disorders include pernicious anemia, Addison's disease, psoriasis, inflammatory bowel disease, psoriatic arthritis, Sjögren's syndrome, lupus erythematosus (e.g., discoid lupus erythematosus, drug-induced lupus erythematosus, and neonatal lupus erythematosus), multiple sclerosis and reactive arthritis.

Additional disorders that may be heated using the methods of the present disclosure include, for example, polymyositis, dermatomyositis, multiple endocrine failure, Schmidt's syndrome, autoimmune uveitis, adrenalitis, thyroiditis, autoimmune thyroid disease, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia pemphigus vulgaris, pemphigus, alopecia areata, pemphigoid, scleroderma, progressive systemic sclerosis, adult onset diabetes mellitus (e.g., type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermantis, atopic rhinitis, Goodpasture's syndrome, Chagas' disease sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps Evan's syndrome, and autoimmune gonadal failure.

In another embodiment, the present antibody or its fragment can be used in the treatment of various disorders associated with the expression of CD40.

A disorder may be any condition that would benefit from treatment with the present antibody or its fragment. This includes chronic and acute disorders or diseases including those pathological conditions that predispose the mammal to the disorder in question. Non-limiting examples of disorders to be treated herein include autoimmune diseases, immunologic disorders, inflammatory disorders, cancer, hematological malignancies, benign and malignant tumors, leukemia, lymphoid malignancies, and angiogenic disorders.

As used herein, the term "CD40-associated disorder" or "CD40-associated disease" refers to a condition in which modification or elimination of cells expressing CD40 is indicated. These include CD40-expressing cells demonstrating abnormal proliferation or CD40-expressing cells that are associated with cancerous or malignant growth. CD40-associated disorders include, but are not limited to, diseases and disorders of the immune system, such as autoimuume disorders and inflammatory disorders. Such conditions include, but are not limited to, rheumatoid arthritis (RA), systemic lupus erythematosus (SLE), scleroderma, Sjogren's syndrome, multiple sclerosis, psoriasis, inflammatory bowel disease (e.g., ulcerative colitis and Crohn's disease, pulmonary inflammation, asthma, and idiopathic thrombocytopenic purara (ITP). More particular examples of cancers that demonstrate abnormal expression of CD40 antigen include B lymphoblastoid cells, Burkitt's lymphoma, multiple myeloma, T cell lymphomas, Kaposi's sarcoma, osteosarcoma, epidermal and endothelial tumors, pancreatic, lung, breast, ovarian, colon, prostate, head and neck, skin (melanoma), bladder, and kidney cancers. Such disorders also include, but are not limited to, leukemias, lymphomas, including B cell lymphoma and non-Hodgkin's lymphoma, multiple myeloma, Waldenstrom's macroglobulmemia; solid tumors, including sarcomas, such as osteosarcoma, Ewing's sarcoma, malignant melanoma, adenocarcinoma, including ovarian adenocarcinoma, Kaposi's sarcoma/Kaposi's tumor and squamous cell carcinoma. U.S. Pat. No. 9,090,696.

CD40-expressing cancers that can be treated or prevented by the present antibodies or fragments thereof also include, for example, leukemia, such as acute leukemia, acute lymphocytic leukemia, acute myelocytic leukemia (e.g., myeloblastic, promyelocytic, myelomonocytic, monocytic or erythroleukemia), chronic leukemia, chronic myelocytic (granulocytic) leukemia, or chronic lymphocytic leukemia; Polycythemia vera; Lymphoma (e.g., Hodgkin's disease or Non-Hodgkin's disease), multiple myeloma, Waldenstrom's macroglobulinemia; heavy chain disease: solid tumors such sarcomas and carcinomas (e.g., fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenoearcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, or esophageal carcinoma).

Also encompassed are methods of treating disorders of B lymphocytes (e.g., systemic lupus erythematosus, Goodpasture's syndrome, rheumatoid arthritis, and type I diabetes), of Th1-lymphocytes (e.g., rheumatoid arthritis, multiple sclerosis, psoriasis, Sjorgren's syndrome, Hashimoto's thyroiditis, Graves's disease, primary biliary cirrhosis, Wegener's granulomatosis, tuberculosis, or graft versus host disease), or of Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease).

In some embodiments, the immunological disorder is a T cell-mediated immunological disorder, such as a T cell disorder in which activated T cells associated with the disorder express CD40. Anti-CD40 antibodies or agents can be administered to deplete such CD40-expressing activated T cells. In a specific embodiment, administration of anti-CD40 antibodies or agents can deplete CD40-expressing activated T cells, while resting T cells are not substantially depleted by the anti-CD40 or agent. In this context, "not substantially depleted" means that less than about 60%, or less than about 70% or less than about 80% of resting T cells are not depleted.

Combination Therapy

The present antibody or antigen-binding portion thereof can be administered alone or in combination with one or more other therapeutic agents (e.g., a second therapeutic agent). In some embodiments, the pharmaceutical compositions comprising the anti-CD40 antibody or its fragment can further comprise a second therapeutic agent, either conjugated or unconjugated to the antibody or its fragment. In one embodiment, the second agent is another monoclonal or polyclonal antibody or antigen-binding portion thereof. In another embodiment, the second agent is an immunosuppressant. In a third embodiment, the second agent is a cytotoxic or cytostatic agent. In a fourth embodiment, the second agent may target a receptor or receptor complex other than CD40 on the surface of activated lymphocytes, dendritic cells or CD40-expressing cancer cells.

Such combination therapy can have an additive or synergistic effect on condition parameters (e.g., severity of a symptom, the number of symptoms, or frequency of relapse).

The present anti-CD40 antibody or its fragment may be administered concurrently with the second therapeutic agent. In another specific embodiment, the second therapeutic agent is administered prior or subsequent to administration of the anti-CD40 antibody or its fragment.

The antibodies and antibody fragments described herein can be formulated or administered in combination with an immunosuppressant. Examples of immunosuppressants include, but are not limited to, calcineurin inhibitors (e.g., cyclosporin A (Sandimmune®), cyclosporine G tacrolimus (Prograf®, Protopic®)), mTor inhibitors (e.g., sirolimus (Rapamune®, Neoral®), temsirolimus (Torisel®), zotarolimus, and everolimus (Certican®)), fingolimod (Gilenya™), myriocin, alemtuzumab (Campath®, MabCampath®, Campath-1H®), rituximab (Rituxan®, MabThera®), an anti-CD4 monoclonal antibody (e.g., HuMax-CD4) an anti-LFA1 monoclonal antibody (e.g., CD11a), an anti LFA3 monoclonal antibody, an anti-CD45 antibody (e.g., an anti-CD45RB antibody), an anti-CD19 antibody (see, e.g., U.S. Patent Publication 2006/0280738), monabatacept (Orencia®), belatacept, indolyl-ASC (32-indole ether derivatives of tacrolimus and ascomycin), azathioprine (Azasan®, Imuran®), lymphocyte immune globulin and anti-thymocyte globulin [equine] (Atgam®), mycophenolate mofetil (Cellcept®), mycophenolate sodium (Myfortic®), daclizumab (Zenapax®), basiliximab (Simutlec®), cyclophosphamide (Endoxan®, Cytoxan®, Neosar™, Procytox™, Revimmune™), prednisone, prednisolone, leflunomide (Arava®), FK778, FK779, 15-deoxyspergualin (DSG), busulfan (Myleran®, Busulfex®), fludarabine (Fludara®), methotrexate (Rheumatrex®, Trexall®), etanercept (Enbrel®), adalimumab (Humira®), 6-mercaptopurine (Purinethol®), 15-deoxyspergualin (Gusperimus), LF15-0195, bredinin, brequinar, and muromonab-CD3 (Orthoclone®).

Methods for assessing immunosuppressive activity of an agent are known in the art. For example, the length of the survival time of the transplanted organ in vivo with and without pharmacological intervention serves as a quantitative measure for the suppression of the immune response. In vitro assays may also be used, for example, a mixed lymphocyte reaction (MLR) assay (see, e.g., Fathman et al., J. Immunol. 118:1232-8, 1977); a CD3 assay (specific activation of immune cells via an anti-CD3 antibody (e.g., OKT3)) (see, e.g., Khanna et al., Transplantation 67:882-9, 1999; Khanna et al. (1999) Transplantation 67:S58); and an IL-2R assay (specific activation of immune cells with the exogenuously added cytokine IL-2) (see e.g., Farrar et al., J Immunol 126:1120-5, 1981).

Cyclosporine A (CsA; CAS No. 59865-13-3, U.S. Pat. No. 3,737,433) and its analogs may be used as an immunosuppressant. A number of other cyclosporines and their derivatives and analogs that exhibit immunosuppressive activity are known. Cyclosporines and their formulations are described, for example, in 2004 Physicians' Desk Reference® (2003) Thomson Healthcare, 58th ed., and U.S. Pat. Nos. 5,766,629; 5,827,822; 4,220,641; 4,639,434; 4,289,851; 4,384,996; 5,047,396; 4,388,307; 4,970,076; 4,990,337; 4,822,618; 4,576,284; 5,120,710; and 4,894,235.

Tacrolimus (FK506) is a macrolide which exerts effects largely similar to CsA, both with regard to its molecular mode of action and its clinical efficacy (Liu, Immunol. Today 14:290-5, 1993; Schreiber et al., Immunol. Today, 13:136-42, 1992); however, these effects are exhibited at doses that are 20 to 100 times lower than CsA (Peters et al., Drugs 46:746-94, 1993). Tacrolimus and its formulations are described, for example, in 2004 Physicians' Desk Reference® (2003) Thomson Healthcare 58th ed, and U.S. Pat. Nos. 4,894,360; 4,929,611 and 5,164,495.

Sirolimus (rapamycin) is an immunosuppressive lactam macrolide produceable, for example by Streptomyces hygroscopicus. Numerous derivatives of sitolimus and its analogs and their formulations are known and described, for example, in 2004 Physicians' Desk Reference® (2003) Thomson Healthcare, 58th ed., European Patent EP 0467606, PCT Publication Nos. WO 94/02136, WO 94/09010, WO 92/05170, WO 93/11130, WO 94/02385, WO 95/14023 and WO 94/02136, and U.S. Pat. Nos. 5,023,262; 5,120,725; 5,120,727, 5,177,203; 5,258,389; 5,118,677; 5,118,678; 5,100,883; 5,151,413; 5,120,842; and 5,256,790.

In some embodiments, the second agent is a cytotoxic agent which may be a convention chemotherapeutic such as, for example, doxorubicin paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to the anti-CD40 antibodies or agents thereof.

In additional embodiments, the second agent is a humanized anti-HER2 monoclonal antibody, RITUXAN (rituximab: Genentech, Inc., South San Francisco, Calif.), a chimeric anti-CD20 monoclonal antibody), OVAREX (AltaRex Corporation, MA); PANOREX (Glaxo Wellcome, N.C.; a murine IgG2a antibody); ERBITUX (cetuximab) (Imclone Systems Inc., N.Y.; an anti-EGFR IgG chimeric antibody); VITAXIN (MedImmune, Inc., MD); CAMPATH I/H (Leukosite, Mass.; a humanized IgG1 antibody); Smart M195 (Protein Design Labs, Inc., CA; a humanized anti- CD33 IgG antibody); LymphoCide (Immunomedics, Inc., NJ; a humanized anti-CD22 IgG antibody); Smart ID10 (Protein Design Labs, inc., CA; a humanized anti-HLA-DR antibody), Oncolym (Techniclone, Inc., CA; a radiolabeled murine anti-HLA-Dr10 antibody); ALLOMUNE (BioTransplant, Calif.; a humanized anti-CD2 mAb): AVASTIN (Genemech, Inc., CA; an anti-VBGF humanized antibody); Epratuzamab (Imnunomedics, Inc., NJ and Amgen, CA; an anti-CD22 antibody); and CEAcide (Immunonedics, NJ; a humanized anti-CEA antibody).

Other suitable antibodies that may be used as the second agent include, but are not limited to, antibodies against the following antigens: CA125, CA15-3, CA19-9, L6, Lewis Y, Lewis X, alpha fetoprotein, CA 242 placental alkaline phosphatase, prostate specific antigen prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen IL-2 receptor, CD20, CD52, CD33, CD22, human chorionic gonadotropin, CD38, mucin, P21, MPG, and Neu oncogene product.

Non-Therapeutic Uses

The antibodies described herein are useful as affinity purification agents. In this process, the antibodies or fragments thereof are immobilized on a solid phase such a Protein A resin, using methods well known in the art. The immobilized antibody or its fragment is contacted with a sample containing the CD40 protein (or fragment thereof) to be purified, and thereafter the support is washed with a suitable solvent that will remove substantially all the material in the sample except the CD40 protein, which is bound to the immobilized antibody. Finally, the support is washed with another suitable solvent that will release the CD40 protein from the antibody.

The present anti-CD40 antibodies are also useful in diagnostic assays to detect and/or quantify CD40 protein, for example, detecting CD40 expression in specific cells, tissues, or serum.

The antibodies described herein may be employed in any known assay method, such as competitive binding assays, direct and indirect sandwich assays, and immunoprecipitation assays. See. e.g., Zola, Monoclonal Antibodies: A Manual of Techniques, pp. 147-158 (CRC Press, Inc. 1987).

Pharmaceutical Compositions

The present disclosure provides a composition, e.g., a pharmaceutical composition, containing an antibody, or antigen-binding portion(s) thereof, of The present disclosure, formulated together with a pharmaceutically acceptable carrier. In another embodiment, the composition may contain an isolated nucleic acid encoding the present antibody or antigen-binding portion thereof, and a pharmaceutically acceptable carrier. The composition may be effective to reduce the likelihood of or increase the duration prior to transplant rejection, to induce immunosuppression, or to treat an autoimmune disorder in a subject. The present composition may be effective in any of the methods described herein.

Pharmaceutically acceptable carriers include any and all suitable solvents, dispersion media, coatings, antibacterial and antifungal agents, isotonic and absorption delaying agents, and the like that, are physiologically compatible. Depending on the route of administration the present antibodies (or antigen-binding portion(s) thereof) may be coated in a material to protect the antibodies (or antigen-binding portion(s) thereof) from the action of acids and other natural conditions that may inactivate the antibodies (or antigen-binding portion(s) thereof). The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In certain embodiments, the present composition may include isotonic agents, for example, sugars, polyaleohols such as mannitol, sorbitol, or sodium chloride in the composition. Prolonged absorption of the injectable compositions can be brought about by including in the composition an agent that delays absorption, for example, monostearate salts and gelatin.

Pharmaceutical compositions of the invention may contain the present antibody or its fragment, and the second therapeutic agent as described herein (e.g., one or more immunosuppressants).

The composition may be in the form of a solution, a suspension, an emulsion, an infusion device, or a delivery device for implantation, or it may be presented as a solid form (e.g., a dry powder) to be reconstituted with water or another suitable vehicle before use. The compositions may be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nontesorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the vaccine.

The composition can be in the form of a pill, tablet, capsule, liquid, or sustained release tablet for oral administration or a liquid for intravenous intrathecal, subcutaneous or parenteral administration, or a polymer or other sustained release vehicle for local administration.

In one aspect, a solution of the composition is dissolved in a pharmaceutically acceptable carrier, e.g., an aqueous carrier if the composition is water-soluble. Examples of aqueous solutions include, e.g., water saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamme oleate. Solid formulations can be used in The present disclosure. They can be formulated as, e.g., pills, tablets, powders or capsules. For solid compositions, conventional solid carriers can be used which include, e.g., mannitol, lactose, starch, magnesium stearate, sodium saccharin, talcum, cellulose, glucose, sucrose, magnesium carbonate, and the like. Suitable pharmaceutical excipients include e.g., starch, cellulose, talc, glucose, lactose, sucrose, gelatin, malt, rice, flour, chalk, silica gel, magnesium stearate, sodium stearate glycerol monostearate, sodium chloride, dried skim milk, glycerol, propylene glycol, water, ethanol.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.).

In one aspect, the pharmaceutical formulations comprising compositions or nucleic acids polypeptides, or antibodies of the invention are incorporated in lipid monolayers or bilayers. e.g., liposomes. U.S. Pat. Nos. 6,110,490; 6,096,716; 5,283,185 and 5,279,833. Aspects of the invention also provide formulations in which water soluble nucletc acids, peptides or polypeptides of the invention have been attached to the surface of the monolayer or bilayer. For example, peptides can be attached to hydrazide-PEG-(distearoylphosphatidyl) ethanolamine-containing liposomes (see, e.g., Zalipsky, Bioconjug. Chem 6: 705-708, 1995). Liposomes or any form of lipid membrane, such as planar lipid membranes or the cell membrane of an intact cell, e.g., a red blood cell, can be used. Liposomal formulations can be by any means, including admimstration intravenously, transdermally (see e.g., Vutla, J. Pharm. Sci. 85: 5-8, 1906), transmucosally, or orally. The invention also provides pharmaceutical preparations in which the nucleic acid, peptides and/or polypeptides of the invention are incorporated within micelles and or liposomes (see, e.g. Suntres, J. Pharm. Pharmacol 46: 23-28, 1904, Woodle. Pharm. Res. 9; 260-265, 1992). Liposomes and liposomal formulations can be prepared according to standard methods and are also well known in the art. Akimaru, Cytokines Mol. Ther. 1; 197-210, 1995. Alving, Immunol. Rev. 145: 5-31, 1995. Szoka, Ann. Rev. Biophys. Bioeng. 9: 467, 1980. U.S. Pat. Nos. 4,235,871; 4,501,728 and 4,837,028.

In one aspect, the compositions are prepared with carriers that will protect the peptide against rapid elimination from the body, such as a controlled release formulation including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. U.S. Pat. No. 4,522,811.

A composition of The present disclosure can be administered by a variety of methods known in the art. As will be appreciated by the skilled artisan, the route and/or mode of administration will vary depending upon the desired results. Administration may be parenteral, intravenous, intrathecal, subcutaneous, oral, topical, local, intramuscular, intradermal, transdermal, subdermal, rectal spinal, or epidermal. Intravenous delivery by continuous infusion is one exemplary method for administering the present antibodies.

To administer the present agent by certain routes of administration, it may be necessary to coat the agent with, or co-administer the agent with, a material to prevent its inactivation. For example, the agent may be administered to a subject in an appropriate carrier, for example, liposomes, or a diluent. Pharmaceutically acceptable diluents include saline and aqueous buffet solutions. Liposomes include water-in-oil-in-water CGF emulsions as well as conventional liposomes (Strejan et al., *J. Neuroimmunol.* 7:27-41, 1984)

Parenteral administration can include modes of administration other than enteral and topical administration, usually by injection, and include, without limitation, intravenous, intramuscular intraarterial intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Examples of suitable aqueous and nonaqueous earners which may be employed in the pharmaceutical compositions of the invention include water, ethanol polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials such as lecithin, by the maintenance of the required particle size in the case of dispersions, and by the use of surfactants.

Methods for preparing parenterally administrable compositions will be known or apparent to those skilled in the art and are described in detail. Bai, J. Neuroimmunol. 80: 65-75, 1997. Warren. J Neurol. Sci. 152: 31-38, 1997. Tonegawa, J. Exp. Med. 186:507-515, 1997. Formulations for parenteral administration may, for example, contain excipients, sterile water, saline polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the present agent. Nanoparticulate formulations (e.g., biodegradable nanoparticles, solid lipid nanoparticles, liposomes) may be used to control the biodistribution of the present agent. Other potentially useful delivery systems include ethylene-vinyl acetate copolymer particles, osmotic pumps, intrathecal pumps, implantable infusion systems, and liposomes. The concentration of the agent in the formulation varies depending upon a number of factors, including the dosage of the drug to be administered, and the route of administration.

Sterile injectable solutions can be prepared by incorporating the present agent in the required amount in an appropriate solvent with one or a combination of ingredients enumerated above, as required, followed by sterilization microfiltration. Generally, dispersions are prepared by incorporating the present agent into a sterile vehicle that contains a basic dispersion medium and the required other ingredients from those enumerated above. In the case of sterile powders for the preparation of sterile injectable solutions, the methods of preparation include vacuum drying and freeze-drying (lyophilization) that yield a powder of the active ingredient plus any additional desired ingredient from a previously sterile-filtered solution thereof. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous injection or once or twice monthly by subcutaneous injection. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active agent calculated to produce the desired therapeutic effect in association with the required pharmaceutical earner. The specification for the dosage unit forms of the invention are dictated by and directly dependent on (a) the unique characteristics of the active agent and the particular therapeutic effect to be achieved, and (b) the limitations inherent in the art of agenting such an active agent for the treatment of sensitivity in individuals.

When administered orally, the present compositions may be protected from digestion. This can be accomplished either by complexing the antibody or antigen-binding portion thereof with a composition to render it resistant to acidic and enzymatic hydrolysis or by packaging the antibody or antigen-binding portion thereof in an appropriately resistant carrier such as a liposome. Means of protecting agents from digestion are well known in the art. Fix, Pharm Res. 13:1760-1764, 1996. Samanen, J. Pharm. Pharmacol. 48:119-135, 1996, U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. Sayani Crit. Rev. Ther. Drug Carrier Syst. 13: 85-184, 1996. For topical, transdermal administration, the agents are formulated into ointments, creams, salves, powders and gels. Transdermal delivery systems can also include, e.g., patches.

The present compositions can also be administered in sustained delivery or sustained release mechanisms. For example, biodegradeable microspheres or capsules or other biodegradeable polymer configurations capable of sustained delivery of a peptide can be included in the formulations of the invention (see. e.g., Putney, Nat. Biotechnol. 16: 153-157, 1998).

For inhalation, the present compositions can be delivered using any system known in the art, including dry powder aerosols, liquids delivery systems, air jet nebulizers, propellant systems, and the like. Patton, Biotechniques 16:141-143, 1998. Also can be used in The present disclosure are product and inhalation delivery systems for polypeptide macro molecules by, e.g., Dura Pharmaceuticals (San Diego, Calif.), Aradigrn (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

Compositions can be administered in a single dose treatment or in multiple dose treatments on a schedule and over a time period appropriate to the age, weight and condition of the subject, the particular composition used, and the route of administration. The frequency of administration can vary depending on any of a variety of factors, e.g., severity of the symptoms, degree of immunoprotection desired, whether the composition is used for prophylactic or curative purposes, etc. For example, in one embodiment, the composition according to the invention is administered once per month, twice per month, three times per month, every other week (qow) once per week (qw), twice per week (biw), three times per week (tiw), four times per week, five times per week, six times per week, every other day (qod), daily (qd), twice a day (qid), or three times a day (tid).

The duration of administration of a polypeptide according to the invention, e.g., the period of time over which the composition is administered, can vary, depending on any of a variety of factors, e.g., subject response, etc. For example, the composition can be administered over a period of time ranging from about one day to about one week, from about two weeks to about four weeks, from about one month to about two months, from about two months to about four months, from about four months to about six mouths, from about six months to about eight months, from about eight months to about 1 year, from about 1 year to about 2 years, or from about 2 years to about 4 years or more.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agent calculated to produce the desired therapeutic effect in association with the required pharmaceutical carrier.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular agent being employed, the duration of the treatment, other drugs, agents and/or materials used its combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the agents of the invention employed in the pharmaceutical composition at levels lower than that required in order to achieve the desired therapeutic effect and gradually increase the dosage until the desired effect is achieved. In general, a suitable daily dose of a composition of the invention will be that amount of the agent which is the lowest dose effective to produce a therapeutic effect. Such an effective dose will generally depend upon the factors described above. If desired, the effective daily dose of a therapeutic composition may be administered as two, three, four, five, six or more sub-doses administered separately at appropriate intervals throughout the day, optionally, in unit dosage forms.

The data obtained from the cell culture assays and animal studies can be used in formulating a range of dosage for use in humans. In one embodiment, the dosage of such agents lies within a range of circulating concentrations that include the $ED_{50}$ with little or no toxicity. The dosage can vary within this range depending upon the dosage form employed and the route of administration utilized. In another embodiment the therapeutically effective dose can be estimated initially from cell culture assays. A dose can be formulated in animal models to achieve a circulating plasma concentration range that includes the $IC_{50}$ (i.e., the concentration of the test agent which achieves a half-maximal inhibition of symptoms) as determined in cell culture. Sonderstrup, Springer, Sem, Immunopathol. 25: 35-45, 2003. Nikula et al., Inhal. Toxicol 4(12): 123-53, 2000.

An exemplary, non-limiting range for a therapeutically or prophylactically effective amount of an antibody or antigen-binding portion of the invention is from about 0.001 to about 100 mg/kg body weight or more, about 0.1 to about 100 mg/kg body weight, about 0.01 to about 80 mg/kg body weight, about 0.001 to about 60 mg/kg body weight, about 0.01 to about 30 mg/kg body weight, about 0.01 to about 25 mg/kg body weight, about 0.5 to about 25 mg/kg body weight about 0.1 to about 15 mg/kg body weight, about 0.1 to about 20 mg/kg body weight, about 10 to about 20 mg/kg body weight, about 0.75 to about 10 mg/kg body weight, about 1 to about 10 mg kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight. The dosage administered to a subject may also be about 0.1 mg/kg to about 50 mg/kg, about 1 mg/kg to about 30 mg/kg about 1 mg/kg to about 20 mg/kg, about 1 mg/kg to about 15 mg/kg, or about 1 mg/kg to about 10 mg/kg of the subject's body weight. Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg of the subject's body weight WO 94/04188.

The composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging hum about 0.01 mg to about 10 g, from about 0.1 mg to about 9 g, from about 1 mg to about 8 g, from about 1 mg to about 7 g, from about 5 mg to about 6 g, from about 10 mg to about 5 g, from about 20 mg to about 1 g, from about 50 mg to about 800 mg, from about 10 mg to about 500 mg, from about 0.01 mg to about 10 g, from about 0.05 µg to about 1.5 mg, from about 10 µg to about 1 mg protein, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

Articles of Manufacture

In another aspect, an article of manufacture containing materials useful for the treatment of the conditions or disorders described herein is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition may be the humanized anti-CD40 antibody or its fragment, or any other antibody or its fragment as described herein. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

In one embodiment, the invention provides for a kit containing an anti-CD40 antibody or antigen-binding portion thereof. Additional components of the kits may include one or more of the following instructions for use; other reagents, a therapeutic agent, or an agent useful for coupling an antibody to a label or therapeutic agent, or other materials for preparing the antibody for administration; pharmaceutically acceptable carriers; and devices or other materials for administration to a subject.

The kit may or may not contain the second therapeutic agent as described herein. The agents can be mixed together, or packaged separately within the kit.

The kit may or may not contain at least one nucleic acid encoding anti-CD40 antibodies or fragment thereof, and instructions for expression of the nucleic acids. Other possible components of the kit include expression vectors and cells.

The present antibody or its fragment can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Epitope Mapping

Methods for identifying the particular epitope to which an antibody binds are known to those skilled in the art. Standard techniques include peptide scanning, in which overlapping, short peptides (for example, 10-30 amino acids, e.g., 20, in length) derived from the full length protein to which the antibody binds are individually tested for their ability to bind the antibody. From such experiments, the region of the protein to which the antibody binds can then be determined.

Site-directed mutagenesis can also be used to identify the antigenic region(s) of a particular protein. In this approach, point mutations are systematically introduced into the target polypeptide and the ability of the antibody to bind the peptide with mutations at various positions is used to determine whether a particular region of that protein contains the epitope to which the antibody binds.

Antibody epitopes can also be identified using high-throughput mutagenesis techniques, such as Shotgun Mutagenesis (Integral Molecular, Inc., Philadelphia, Pa.), which can be used to generate huge numbers of mutations within the target protein. Such methodologies permit efficient identification of epitopes within the protein.

To determine if various antibodies to CD40 bind similar epitopes, an in vitro competitive blockade assay may be performed. In one embodiment, the antibodies 2C10, 3A8 and Chi220, a chimeric IgG1 CD40-specific antibody, were used in the assay. 2C10 was conjugated to allophycocyanin (APC) using the Lightning Link antibody labeling kit (Novus Biologics, Littleton, Co.). Human PBMCs were incubated with escalating concentrations of 2C10, 3A8, or Chi220, and then stained with the APT-conjugated 2C10 to assess the ability of each antibody to cross-block 2C10. Binding of APC-conjugated 2C10 decreased with increasing concentrations of 2C10 but not Chi220 or 3A8 as shown in FIG. 12. The result indicates that 2C10 binds a unique epitope distinct from either Chi220 or 3A8.

CD40 Fragments

The invention also features fragments of CD40 that include the epitope that is specifically bound by the 2C10 antibody. The 2C10 antibody was raised against the extracellular portion of the CD40 polypeptide. The 2C10 antibody reacts with a portion of this sequence (SEQ ID NOs: 5 and 6).

The disclosure therefore features CD40 fragments (e.g., fewer than 150, 120, 100, 80, 70, 60, 50, 40, 30, 20, 18, 15, 12, 11, 10, 9, 8, or 7) amino acids in length that are specifically bound by the 2C10 antibody. In certain embodiments, the fragment is 8-10, 8-12, 8-15, 8-20, 8-30, 8-40, 8-50, 8-60, 8-70, 8-80, or 8-100 amino acids in length. In other embodiments, the fragment is 7-10, 7-12, 7-15, 7-20, 7-30, 7-40, 7-50, 7-60, 7-70, 7-80 or 7-100 in length. The 2C10 antibody binds to an epitope present within the sequence of amino acids 8-10, 8-12, 8-15, 8-20, 8-30, 8-40, 8-50, 8-60, 8-70, 8-80, 8-100, 7-10, 7-12, 7-15, 7-20, 7-30, 7-40, 7-50, 7-60, 7-70, 7-80, or 7-100, of SEQ ID NO: 6.

The invention also features fusion protein that includes a fragment described herein and a heterologous sequence. In certain embodiments, one of the fusion partners is the Fc protein (e.g., mouse Fc or human Fc). The fusion may also be a sequence useful for antibody production, e.g., a maltose binding protein or GST. In other embodiments, the fusion protein is a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments, the fusion partner may be a tag, such as c-myc, poly histidine, or FLAG. Each fusion partner may contain one or more domains e.g., a preprotrypsin signal sequence and FLAG tag.

The CD40 fragments and fusion proteins described herein may be produced by transformation of a suitable host cell with a polynucleotide molecule encoding the polypeptide fragment or fusion protein in a suitable expression vehicle.

Any of a wide variety of expression systems may be used. Exemplary expression systems include prokaryotic hosts (e.g., *E. coli*) and eukaryotic hosts (e.g., *S. cervisiae*, insect cells, e.g., Sf21 cells, or mammalian cells, e.g., NIH 3T3, HeLa, or preferably COS cells). Such cells are available from a wide range of sources (e.g., the American Type Culture Collection, Manassas, Va.). The method of transformation or transfection and the choice of expression vehicle will depend on the host system selected. Transformation and transfection methods are described e.g., in Kucherlapti et al. (*CRC Crit. Rev. Biochem.* 16:349-379, 1982) and in *DNA Transfer to Cultured Cells* (eds., Ravid and Freshney, Wiley-Liss, 1998); and expression vehicles may be chosen from those provided, e.g., in *Vectors: Expression Systems: Essential Techniques* (ed., Jones, Wiley & Sons Ltd., 1998).

Once the recombinant CD40 polypeptide fragment or fusion protein is expressed, it can be isolated e.g., using affinity chromatography. In one example, an antibody specific to CD40 (e.g., an antibody or its fragment as described herein) may be attached to a column and used to isolate the polypeptide fragment or fusion protein. Lysis and fractionation of fragment- or fusion protein-harboring cells prior to affinity chromatography may be performed by standard methods (see e.g., *Methods in Enzymeology*, volume 182, eds., Abelson, Simon, and Deutscher, Elsevier, 1990). Once isolated, the CD40 polypeptide fragment or fusion protein can, if desired, be further purified, e.g., by high performance liquid chromatography (see e.g., Fisher, *Laboratory Techniques in Biochemistry and Molecular Biology*, eds., Work and Burdon, Elsevier, 1980; and Scopes, *Protein Purification: Principles and Practice*, Third Edition, ed., Cantor, Springer, 1994).

The CD40 polypeptide fragments or fusion proteins can also be produced by chemical synthesis (e.g., by the methods described in *Solid Phase Peptide Synthesis,* 2nd ed., 1984. The Pierce Chemical Co., Rockford, Ill.; and Solid-Phase Synthesis: A Practical Guide, ed., Kates and Albericio, Marcel Dekker Inc., 2000).

The present antibodies, antigen-binding portions thereof, compositions and methods can be used in all vertebrates, e.g., mammals and non-mammals including human, mice, rats, guinea pigs, hamsters, dogs cats, cows, horses, goats, sheep, pigs, monkeys, apes, gorillas, chimpanzees, rabbits, ducks, geese, chickens, amphibians, reptiles and other animals.

The following examples of specific aspects for carrying out the present disclosure are offered for illustrative purposes only, and are not intended to limit the scope of the present disclosure in any way.

Example 1 Production and Identification of Anti-CD40 Murine Antibodies

Mice (strain AJ) were immunized with a fusion protein consisting of the extracellular domain of rhesus macaque (*M. mulatia*) CD40 (amino acid sequence: EPPTACREKQYLINSQCCSLCQPGQKLVSDCTEFT-ETECLPCSESEFLDTWNRETRCHQH KYCDPNLGL-RVQQKGTSETDTICTCEEGLHCMSESCESCV: SEQ ID NO: 5) fused to maltose binding protein (CD40-MBP). The amino acid sequence in this region of the rhesus macaque CD40 protein differs from human CD40 protein at five amino acid positions (human amino acid sequence: EPPTACREKQYLINSQCCSLCQPGQKLVSDCTEFT-ETECLPCGESEFLDTWNRETHCHQH KYCDPNLGL-RVQQKGTSETD TICTCEEGWHCTSEACESCV; SEQ ID NO: 6). CD40-MBP was administered to mice multiple times with complete Freund's adjuvant and incomplete Freund's adjuvant Splenocytes from immunized mice were fused with the mouse myeloma cell line SP2/0 and hybrids selected using standard hybridoma technology.

Antibodies were selected for reactivity in a second fusion protein consisting of the same rhesus CD40 domain fused to glutamine synthetase (CD40-GST). Antibodies reactive to CD40-GST by ELISA were further tested for reactivity to native CD40 expressed on rhesus macaque blood B cells, human blood B cells and rhesus macaque B-lymphoblastoid cell lines by flow cytometry. As a final level of selection, antibodies were tested in an in vitro assay for their ability to inhibit human or rhesus macaque B cell activation after co-culture CD154-expressing Jurkat D1.1 cells. A stable subclone of anti-CD40 antibody 2C10 was obtained by limiting dilution. The antibody is a mouse IgG1-kappa. Lowe et. al., A novel monoclonal antibody to CD40 prolongs islet allograft survival. Am. J Transplant (2012) 12(8):2079-87

Antibody Cloning

Variable regions of monoclonal antibodies can be cloned using any method known in the art. PCR-based methods for obtaining antibody variable region sequences for hybridoma cells are described, for example, in Larrick et al., *Nat. Biotechnol.* 7:934-8, 1989 and in Orlandi et al., *Proc. Natl. Acad. Sci. USA* 86:3833-7, 1989. Using these techniques or similar techniques, the variable regions of monoclonal antibodies can be cloned and subject to further manipulation. In the present case, the variable sequences from the heavy and light chains of the 2C10 antibody were cloned and were sequenced. The DNA representing the immunoglobulin heavy and light chain variable regions from the 2C10 hybridoma were cloned using 5' RACE PCR employing the following DNA primers:

```
Mouse kappa reverse:
                                    (SEQ ID NO: 7)
5'-CTA ACA CTC ATT CCT GTT GAA GCT CTTGAC;

Mouse kappa forward:
                                    (SEQ ID NO: 8)
5'-GCT GAT GCT GCA CCA ACT GTA TCC-3'

Mouse IgG1 reverse:
                                    (SEQ ID NO: 9)
5'-GGC AAC GTT GCA GGT CTC GC-3'

Mouse IgG1 forward:
                                    (SEQ ID NO: 10)
5'-CTG GAT CTG CTG CCC AAA CTA ACT CC-3'
```

PCR products were cloned into a commercial cloning vector and were sequenced using standard sequencing techniques. The resulting sequences are provided in FIG. 1.

The immunoglobulin variable region genes were cloned from the hybridomas secreting anti-CD40 antibody clone 2C10 and from anti-human CD40 clone 3A8 (Kwekkeboom et al., *Immunology* 79:439-44, 1993) (obtained from the American Type Culture Collection, ATCC, Vienna, Va.) using 5' rapid amplification of cDNA ends-polymerase chain reaction. The immunoglobulin heavy and light chain variable regions were subcloned into expression vectors containing rhesus IgG1 or rhesus IgG4 heavy chain and rhesus kappa light chain constant region sequences.

Recombinant heavy and light chains were subcloned into expression vectors and packaged in retroviral vectors used to transduce Chinese hamster ovary cells using the GPEx™ expression technology (Catalent Pharma Solutions, Middleton, Wis.). A pool of transduced cells was grown in serum-free medium and secreted antibody was purified by protein A affinity chromatography. The purified chimeric rhesus IgG1 (2C10R1, 3A8R1) and IgG4 (2C10R4) antibodies were diafiltered into phosphate buffer; endotoxin levels were confirmed to be less than 1 endotoxin unit/mg.

Antibody Characterization

2C10 Binds to CD40 and Prevents Binding of CD154

To assess the ability of 2C10 to bind to both rhesus and human CD40, recombinantly expressed human or rhesus CD40 were adsorbed to ELISA plates and reacted with varying concentrations of 2C10. Binding of 2C10 to CD40 was detected using goat anti-mouse IgG-HRP in an ELISA. The results in FIG. 2B show that 2C10 has similar binding affinities to rhesus and human CD40, which is important for clinical translation of 2C10. To confirm the ability of 2C10 to block binding of its cognate ligand, CD154, rhesus and human B cells were incubated with escalating concentrations of 2C10 or an isotype control and then incubated with histidine-tagged soluble CD154 (R&D Systems, Minneapolis, Minn.) and analyzed for histidine expression. 2C10 blocked the binding of CD154 in a dose-dependent manner (FIG. 3), indicating that 2C10 can effectively block the interaction of T cell-bound CD154 with CD40 on B cells and antigen-presenting cells.

TABLE 2

CD40 Receptor Binding Kinetics of 2C10

| Anti-CD40 Antibodies | 2C10 | 3A8 | 5D12 | 4D11 | Chi220 |
| --- | --- | --- | --- | --- | --- |
| $K_{on}$ (M$^{-1}$ s$^{-1}$) | 2.73 × 10$^3$ | 0.223 × 10$^3$ | 1.51 × 10$^3$ | 1.25 × 10$^3$ | 0.413 × 10$^3$ |
| $K_{off}$ (s$^{-1}$) | 1.86 × 10$^{-6}$ | 4.15 × 10$^{-6}$ | 1.54 × 10$^{-5}$ | 1.58 × 10$^{-6}$ | 2.5 × 10$^{-5}$ |
| $K_D$ (M) | 2.73 × 10$^{-10}$ | 1.86 × 10$^{-8}$ | 1.02 × 10$^{-8}$ | 2.28 × 10$^{-9}$ | 6.07 × 10$^{-8}$ |

2C10 Blocks B Cell Activation in Rhesus Monkey and Human Peripheral Blood Mononuclear Cells The anti-CD40 antibody 2C10 was characterized with respect to its ability to affect B cell activation both using rhesus monkey and human peripheral blood mononuclear cells (PBMCs). CD20 expression was chosen as being an indicator of B cells, and expression of CD23, CD80, and CD86 is associated with B cell activation. 2C10 was first assessed for its ability to bind to CD20. Rhesus or human PBMCs were incubated with fluorochrome-conjugated 2C10 and an anti-CD20 antibody. Flow cytometric analysis was used to confirm the binding of 2C10 to human and rhesus CD20+ B cells (FIG. 2A). In another set of experiments, PBMCs from either rhesus monkey or humans were cultured either in the presence or absence of CD154+ Jurkat D1.1 cells, an immortalized T lymphocyte cell line. Activation of B cells was determined by measuring expression of three markers (CD23, CD80, and CD86) in CD20+ cells present in the PBMCs. The general scheme of this assay is shown in FIG. 4. As shown in FIG. 4, culturing PBMCs in the presence of Jurkat cells resulted in increased expression of all three markets, indicating that B cells are activated by the CD154 Jurkat cells.

To test the ability of antibodies to block B cell activation, PBMCs and Jurkat cells were co-cultured in the presence or absence of one of three antibodies: 3A8, 5C8, and 2C10. The 3A8 antibody is a mouse anti-human CD40 antibody (ATCC Deposit No. HB-12024), and 5C8 is an anti-CD154 antibody (ATCC Deposit No. CRL-10915). Each was used as a positive control. Co-cultures were conducted over a range of five orders of magnitude of antibody concentration (0.001 µg to 10 µg). As shown in FIG. 5, 3A8 did not block B cell activation in rhesus PBMCs, as measured by CD23 expression, whereas both 2C10 and 5C8 were able to block activation with similar efficiency. Corresponding changes were also observed with CD80 and CD86 expression. These results indicate that 2C10 binds to a different epitope on CD40 than 3A8. These results also indicate that 2C10 acts primarily as a CD40 antagonist in contrast to 3A8 which has previously been shown to act as partial agonists with weak stimulatory potential (Adams et al., *J. Immunol.* 174:542-50, 2005, Badell et al., *Am. J. Transplant accepted for publication,* 2011). When a similar experiment was performed using human, rather than rhesus, PBMCs, both 2C10 and 5C8 were again observed to block B cell activation, as measured by CD86 expression, with similar efficiency. Here, the 3A8 antibody, unlike with the rhesus PBMCs, blocked B cell activation (FIG. 6).

The 2C10 and 3A8 antibodies were also tested for their ability to activate B cells in the absence of Jurkat cells using either rhesus monkey or human PBMCs. Here, PBMCs were cultured either in the presence or absence of either 2C10 or 3A8. Expression of CD23, CD80, and CD86 was then measured in CD20+ cells. As shown in FIG. 7, CD23 expression in rhesus cells was increased in the presence of the 3A8, but not the 2C10, antibody. By contrast, neither 3A8 nor 2C10 activated human B cells. The differences in activity observed between the 3A8 and 2C10 antibody indicate that the 2C10 antibody binds to an epitope different from that of the 3A8 antibody.

2C10 Prevents a T Cell-Dependent Antibody Response

Having established that 2C10 binds to a unique epitope on CD40 inhibits B cell activation similarly to an anti-CD154 antibody, and lacks agonistic properties, we then characterized the effects of 2C10 in vivo. Recombinant mouse-rhesus chimeric forms of 2C10 were generated using either rhesus IgG1 (2C10R1) or IgG4 (2C10R4) heavy chain and rhesus kappa light chain constant legion sequences. A chimeric rhesus IgG1 form of 3A8 (3A8R1) was also generated for use as a control.

Rhesus macaques were immunized once on day zero with 4-hydroxy-3-nitrophenylacetyl-conjugated keyhole limpet hemocyanin (KLH, 10 mg IM) antigen (Biosearch Technologies, Novato, Calif.). Prior to immunization and at one week, cohorts of three animals received an intravenous dose (50 mg/kg) of 2C10R1, 2C10R4, 3A8R1, or saline. All animals were observed for 70 days, and flow cytometry was performed weekly. Treatment with either recombinant 2C10 isotypes resulted in modest change in peripheral B cell counts (FIG. 8) compared to the previously reported significant and prolonged depletion of peripheral B cells occurring in animals receiving either 3A8R1 (Badell et al., *Am. J. Transplant.* 10:214, 2010) or Chi220 (Adams et al., *J. Immunol.* 174:542-50, 2005).

T cell-dependent antibody responses to KLH-NP were tested by ELISA. Plates were coated with KLH (0.01 mg/ml. Sigma, St. Louis, Mo.) and blocked with Super Block (Thermo Scientific, Woodstock, Ga.). Pre- and post-treatment plasma samples were serially diluted, plated for 1 hr. and washed with phosphate-buffered saline/0.05% Tween. Anti-KLH antibodies were detected by incubating for 1 hr with monoclonal anti-rhesus IgG-horseradish peroxidase (clone 1B3, NHP Reagent Resource, Boston, Mass.). Plates were then incubated with Peroxidase Substrate Solution (KPL). Stop solution (KPL) was then added, and optical density was read on an ELISA plate reader at 450 nm. A sample was considered positive at a given dilution if the optical density reading of the post-treatment plasma exceeded the optical density of the pre-treatment plasma at the same dilution by 2-fold. Following KLH immunization, control animals developed high-titer KLH-specific IgG (FIG. 9). Animals that received 3A8R1 also developed anti-KLH responses, but titers were approximately 10-fold lower than controls despite significant depletion of B cells. In contrast, the generation of IgG anti-KLH antibodies was nearly completely blocked through day 56 in all animals that received either 2C10R1 or 2C10R4.

2C10 Significantly Prolongs Islet Allograft Survival in a Macaque Model of Allogeneic Islet Transplantation We further tested 2C10R4, the CD4 purified chimeric rhesus IgG4 antibody, in a nonhuman primate allogenic islet transplant model (FIG. 10). Rhesus macaques weighing 10-20 kg underwent donor pancreatectomy one day prior to non-plantation via a midline laparotomy. The pancreas was isolated and placed on ice after the animals were terminally exsanguinated. Islet isolation was performed using Collagenase Neutral protease (950 Wunsch units and 63 units, respectively; Serva, Heidelberg, Germany). The digested pancreas was purified on a four layer, discontinuous Euroficoll gradient (Mediateh, Manassas, Va.) and Cobe 2901 blood cell processor (CaridianBCT, Lakewood, Col.) Samples of the final islet preparation were counted and expressed as islet equivalents (IEQ). Isolated islets were cultured overnight, counted and suspended in Transplant Media (Mediatech).

Rhesus macaques weighing 3-5 kg were rendered diabetic using streptozotocin (1250 mg/m$^2$ IV; Zanosar, Teva Parenteral Medicines, Irvine, Calif.) four weeks prior to transplantation. Diabetes was confirmed by intravenous glucose tolerance test (IVGTT) with a 500 mg/kg bolus of dextrose and measurement of primate C-peptide. Glucose levels were monitored and C-peptide was measured at baseline and 10, 30, 60 and 90 after injection of dextrose. Diabetes was confirmed by measurement of elevated blood glucose levels in the absence of detectable serum C-peptide. Diabetic recipients underwent MHC-mismatched islet allotransplantation. A mean of 15,745 (±4,063) IEQ were infused via a small midline laparotomy and cannulation of a mesenteric vein.

Blood glucose levels were measured twice daily by earstick; NPH (Novolin; Novo Nordisk, Princeton, N.J.) and glargine (Lantus; Sanofi-Aventis, Bridgewater, N.J.) insulin were administered to maintain fasting blood glucose (FBG) less than 300 mg/dL pre-transplant and following graft rejection. IVGTT was performed periodically post-transplant to monitor graft function. Transplant recipients underwent weekly flow cytometric analysis to monitor T cell (CD3 V450, CD4 PerCP-Cy5.5, CD8 PerCp; BD Bioscience) and B cell (CD20 PE, BD Bioscience) populations. After islet engraftment rejection was defined as FBG greater than 130 mg/dL on two consecutive days. Primary endpoint was rejection-free islet graft survival.

Transplant recipients received either 2C10R4, basiliximab (Simulect, Novartis, Basel, Switzerland) and sirolimus, or basiliximab and sirolimus alone. 2C10R4 (50 mg/kg) was administered intravenously on post-operative day (POD) 0 and 7. Basiliximab (0.3 mg/kg) was administered intravenously on POD 0 and 3. Sirolimus was administered intramuscularly daily to achieve trough levels of 5-15 ng/ml through POD 120. All three animals receiving basiliximab and sirolimus alone are historic controls (Badell et al., *J. Clin. Invest.* 120:4520-312, 2010). Two of these historic controls (RQz6 and RIb7) underwent diabetes induction by pancreatectomy and received oral sirolimus.

Treatment with the regimens described above resulted in significantly prolonged islet graft survival (FIG. 11A) compared to controls receiving only basiliximab induction and sirolimus maintenance therapy (FIG. 11B). Median rejection-free graft survival time for animals receiving 2C10R4 is 280 days compared to 8 days for control animals (p=0.010), Table 3). Pharmacokinetic data predict that plasma 2C10R4 levels would be less than 1 μg/ml by POD 100. Because sirolimus was discontinued at POP120, the recipient with the longest survival (304 days) received no immunosuppression for approximately 24 weeks prior to rejection. No animals treated with 2C10R4 developed clinically relevant infectious complications or weight loss. These results reflect animals that received the IgG4 isotype of 2C10. Two additional annuals that received the IgG1 isotype of 2C10 (2C10R1) in combination with basiliximab and sirolimus achieved similarly prolonged graft survival of 220 and 162 days. Given the positive results with 2C10 used as induction therapy, the next step is to assess the effects on graft survival by administering 2C10 as maintenance therapy.

TABLE 3

| Recipient | Therapy | IEQ/kg | Graft Survival (days) | Comment |
|---|---|---|---|---|
| DP4A | 2C10R4/Basiliximab/Sirolimus | 21,973 | 296 | Rejection |
| RAo13 | 2C10R4/Basiliximab/Sirolimus | 14,388 | 304 | Rejection |
| RZq13 | 2C10R4/Basiliximab/Sirolimus | 15,881 | 265 | Rejection |
| RRq13 | 2C10R4/Basiliximab/Sirolimus | 20,596 | 163 | Rejection |
| RQz6 | Basiliximab/Sirolimus | 12,980 | 8 | Rejection |
| RIb7 | Basiliximab/Sirolimus | 10,903 | 8 | Rejection |
| RMc11 | Basiliximab/Sirolimus | 13,796 | 10 | Rejection |

Blockade of the CD40/CD154 Pathway in Conjunction with the CD28/B7 Pathway

Blockade of the CD40/CD154 pathway may prove useful in conjunction with other costimulation blockade agents Belatacept, a high affinity vetsion of CTLA4-Ig designed to block the CD28/B7 costimulatory pathways, has shown efficacy in nonhuman primate models of renal and islet transplantation and in phase II and III clinical trials in renal transplantation (Larsen, et al., *Transplantation* 90: 1528-35, 2010, Vincenti et al., *Am. J. Transplant*, 10:535-46, 2010, Adams et al., J. Immol. 174:542-50, 2005. Adams et al., Diabetes 51:205-70, 2002. Larsen et al., *Am. J. Transplant.* 5:443-53, 2005. Vincenti et al., N. Engl. J. Med. 358:770-81, 2005). The BENEFIT trial revealed superior renal function in patients treated with belatacept; however, these patients had a higher incidence and more severe grade of biopsy-proven acute rejection (Larsen et al., *Transplantation* 90:1528-35, 2010, Vincenti et al., *Am. J. Transplant.* 10:535-46, 2010). In light of this increased rate of acute rejection and the synergy between CD40 and B7 blockade (Larsen el al. *Nature* 381:434-8, 1996), we next will test the efficacy of combined 2C10 and belatacept therapy in nonhuman primate kidney transplantation.

Example 2 Humanized Anti-CD40 Antibodies

We have developed and characterised a novel humanized Ab to CD40 called h2C10 (humanized 2C10 antibody) that was selected as a full functional antagonist of CD40. The binding epitopes were carefully designed to confer unique binding properties that distinguish it from competitor molecules that either activate or deplete B cells or acts as partial agonists. The early mouse primate chimeric version of the antibody has been investigated in relevant preclinical in vitro and in vivo studies, including multiple studies in nonhuman primates that demonstrate promising efficacy against preventing transplant rejection and prolonging both allo- and xenograft survival, and a favorable nonclinical safety profile. We have also completed the humanization of 2C10 (h2C10), which exhibits excellent characteristics.

To produce the humanized anti-CD40 antibodies, the variable region sequences of the murine antibody 2C10 were used to search the human antibody database. The VH was found to be mostly related to germline antibody sequences VH1-46, VH1-69, and VH1-3 (SEQ ID NO: 30), whereas the VL was mostly related to germline antibody sequences VK3-11 (SEQ ID NO: 31), VK1-39, and VK6-21. The human VH1-3 and VK3-11 were chosen to be the acceptor framework for CDR grafting because of relative high usage in human repertoire and good conservation at the critical framework positions 3D models were built with both variable regions after grafting the CDRs from the murine 2C10 antibody into the human acceptor frameworks. Six murine VH framework residues that are different from the human counterparts were identified to be potentially in contact of the CDRs; M48, A67, L69, A71, K73, and N76. After modelling, three humanized VH sequences 2C10_h1, 2C10_h2 and 2C10_h3 were designed to contain 0, 2, and 6 murine framework residues, respectively (FIG. 13a). Similarly, live murine VK framework residues were identified to be potentially in contact of the CDRs; Q1, R46, W47, V58, and Y71. After modeling, two humanized VL sequences 2C10_l1 and 2C10_l2 were designed to contain 0 and 4 murine framework residues, respectively (FIG. 13b).

The parental murine 2C10 antibody was humanized CDR grafting. The human antibody VH1-3 and VK3-11 germline frameworks were chosen to be the acceptor. Three VH and two VL sequences were designed and all 6 humanized antibodies were produced and tested for human CD40 binding.

The 2C10-heavy-3 (2C10_h3) and 2C10_l2) constructs were found to produce the best antibody with CD40 binding affinity of 0.39 within 2-fold of that of the murine 2C10 (0.22 nM) (Table 2). The humanized variable regions were used to construct the clinical candidate humanized antibody as an IgG4 or a stabilized IgG4, which was cloned into the SwiMR expression system.

High producing stable CHO cell lines were isolated by FACS and screened by three rounds of ELISA and one round of fed-batch culture. Seven clones were isolated that produced more than 0.8 g/L of humanized 2C10 in a fed-batch culture. The best clone 3C9-I6 produced ~1.2 g/L under non-optimized conditions.

Construction of Antibody Expression Vectors

The humanized VH sequences were gene synthesized and cloned into vector pFUSE-CH1g-hG2a (Invivogen) containing the constant region of human IgG2 heavy chain to make expression vector LB300-302. The humanized VK sequences were gene synthesized and cloned into an expression vector containing the constant region of human kappa light chain to make expression vector LB303-304. The heavy and light chains were downstream of human EF1α promoter for strong and constitutive mammalian cell expression. The chimeric 2C10 antibody was also constructed similarly by using murine VH and VL to make expression vector LB305 and LB306, respectively. The antibody expression vectors were summarized in Table 4.

TABLE 4

Antibody expression vectors

| Plasmid | VH/VK | CH/CK | Promoter | Selection |
|---|---|---|---|---|
| LB300 | 2C10_h1 | hIgG$_2$ CH | hEF$_1$α | Zeocin |
| LB301 | 2C10_h2 | hIgG$_2$ CH | hEF$_1$α | Zeocin |
| LB302 | 2C10_h3 | hIgG$_2$ CH | hEF$_1$α | Zeocin |
| LB303 | 2C10_l1 | hCK | hEF$_1$α | Neomycin |
| LB304 | 2C10_l2 | hCK | hEF$_1$α | Neomycin |
| LB305 | 2C10_VH | hIgG$_2$ CH | hEF$_1$α | Zeocin |
| LB306 | 2C10_VK | hCK | hEF$_1$α | Neomycin |
| LB308 | 2C10_h3 | hIgG$_4$ CH | hEF$_1$α | Zeocin |
| LB309 | 2C10_h3 | hIgG$_4$ CH (S241P) | hEF$_1$α | Zeocin |

Each vector in Table 4 contains a heavy chain or light chain expression cassette under the control of human EF1a promoter. Vectors LB3000-302, LB305 contain the constant region of human IgG2 heavy chain. Vectors LB308-309 contain the constant region of human IgG4 heavy chain. Vectors LB303-304, LB306 contain the constant region of human Kappa light chain.

Production of the Humanized IgG4 Antibody

In order to further minimize the potential effector function, the humanized antibody with the best binding activity (2C10_h3 and 2C10_2) was converted into human IgG4 or stabilized human IgG4 (S241P). The heavy chain variable region 2C10_h3 was first cloned into vector pFUSE-CH1g-hG4 (Invivogen) containing the constant region of human IgG4 heavy chain, before the stabilizing mutation S241P was introduced (Table 4). The humanized IgG4 and IgG4 (S241P) were purified front 293F cells after transient transfection. The production yield was 25-35 mg/L, 2-fold higher than that of the IgG2 antibodies. The IgG4 antibody appeared to have small amount of half molecule, which was significantly reduced in the stabilized IgG4 antibody. The DNA and amino acid sequence of the stabilized IgG4 antibody is shown in FIG. 21.

Cloning of the Humanized IgG4 (S241P) Antibody in SwiMR Expression Vector

SwiMR expression was developed for facile development of antibody production cell lines, utilizing a switchable membrane reporter to facilitate isolation of highly productive cells via Fluorescence-activated cell sorting (FACS). An IRES-mediated bicistronic expression cassette of membrane-anchored GFP was placed downstream of the gene of interest (GOI). The IRES-GFP cassette was flanked by LoxP sites for later removal from the chromosome. The GFP expression level was used to mark the expression level of the GOI. Highly productive cells were isolated by FACS and then treated with Cre recombinase to remove the GPP cassette. The humanized 2C10 in the stabilized IgG4 format was cloned the SwiMR expression system to make vector LB312. The heavy and light chains were cloned in two separate expression cassettes under control of human EF1α promoters. The IRES-GFP cassette was placed downstream of the heavy chain sequence and was flanked by two LoxP sites. The plasmid carries a Puromycin resistant gene for mammalian cell selection and a β-lactamase gene for bacterial propagation.

Stable Selection of the CHO Cells and Isolation of the High Producing Cells 100 ml of CHOS cells ($\times 10^6$ cells/ml. Invitrogen) were transfected with 120 μg of LB312 linearized by restriction digestion of Asc I and 120 ul of Freestyle Max regent (Invitrogen). The cells were selected with 10-20 ug/ml of Puromycin for 2 weeks. The GFP expression profile of the stable pool was characterized by flow cytometry. The top 1% of the cells with the highest GFP signal was sorted out as Pool #1 containing 100,000 cells. After culturing for 2 weeks, the Pool #1 was analyzed again tor GFP expression by flow cytometry. The top 1% of the cells with the highest GFP signal was sorted out again as Pool #2 containing 100,000 cells. After culturing for 2 days, the Pool #2 was treated with 2 uM of recombinant membrane permeable DNA recombinase Cre (TAT-NLS-Cre, Excellgen). The GFP expression profile was analyzed after 1 week of culturing. ~10% of the cells completely lost the GFP expression indicating successful removal of the GFP expression cassette from the chromosome. The GFP negative cells were sorted out as single cells in 384-well plates. After 2 weeks, ~800 colonies grew out from 10×384-w plates.

Additional Humanized Antibodies

Humanized antibodies were also generated using two CDR grafted VH and two CDR grafted VL sequences cloned into a VH1-69 and a VL1-39 human germline framework. We made two heavy (HB1& HB2) and two light (KB1& KB2) chains in these additional experiments. The heavy and light chain sequences HP+KP serves as the positive control. The combination of these constructs was transiently expressed in HEK293 cells, antibody purified by protein-A chromatography and tested for hCD40 binding.

FIG. 14 shows amino acid changes in framework in between 2C10HP and 2C10HB1, as well as 2C10HB2 constructs. FIG. 15 shows the sequences of heavy chain and light chain variable regions for humanized 2C10 antibodies. The heavy chain and light chain variable regions include 2C10HP, 2C10HB1, 2C10HB2, 2C10KP, 2C10KB1, and 2C10KB2. Therefore, in certain embodiments an anti-CD40 antibody may include any of the following 2C10H-K combinations:

1. 2C10HP+2C10KP
2. 2C10HB1+2C10KB1
3. 2C10HB1+2C10KB2
4. 2C10HB1+2C10KP
5. 2C10HB2+2C10KB2
6. 2C10HB2+2C10KB1
7. 2C10HB2+2C10KP
8. 2C10HP+2C10KB1
9. 2C10HP+2C10KB2

In Vitro Binding of CD40 with Purified Antibodies

Humanized antibodies and the chimeric antibody were purified after transient transection of 100 or 200 ml of 293F cells. The antibodies were purified with a Protein A column from the conditioned media harvested 4 days after transfection.

Determination of CD40 Binding Kinetics

CD40 binding kinetics was determined on Forte Bio (contracted to Aragen Bioscience). The purified CD40 was biotinylated and immobilized on Strepiavidin biosensors.

Bioproduction for In Vivo Study

After transfection of CHO cells and selection of stably transfected cells, the antibody was purified by Protein A column, and followed by buffer exchange (20 mM Sodium Citrate, 50 mM NaCl, 5% Maltose, pH 6.0) and 0.2 μm filtration. The Pool #1 was used to setup 25 L wave bag culture in CD FortiCHO media (Invitrogen). The culture was fed three times on day 3, 5, and 7 with 10% CD Efficient Feed C (Invitrogen). The final yield of purified antibody was 1.6 g in total. The antibody was characterized by SDS-PAGE and SEC-HPLC analysis, and was 99.4% pure as monomeric antibody.

Cell Line Development

The single cell colonies were screened by 3 rounds of ELISA and 1 round of fed-batch production. The cells were kept in CD FortiCHO media throughout the screening process. All colonies from 384-well plates were picked into 96-well plates. 1.2 μl of culture media from each well were used to screen for antibody in ELISA plates coated with anti-human Fc antibody. The top 240 clones were expanded into 10×24-well plates. After culturing for 5 days, 1.2 μl of culture media was screened again for antibody level, the top 60 clones were expanded into 10×6-well plates and cultured in shaking incubator. After culturing for 5 days, the 6-well plates were duplicated by passaging the cells 1:10 into a new set of 6-well plates. The cultures in the original set of the 6-well plates were allowed to grow to extinction, followed by determination of antibody level by ELISA. The top 24 clones in the duplicated set of 6-well plates were expanded into 30 ml culture in 125 ml shake flasks. The clones were subjected to 30 ml fed-batch production. The feeding strategy was 7.5% of Ex-Cell Advanced CHO Feed 1 (Sigma) on day 3, 5, 7, 9, and 11. The top clone 3C9-I6 exhibited production titer of ~1.2 g/L.

In Vitro Pharmacology of Primate Chimeric 2C10 and Humanized 2C10

We identified the following important in vitro pharmacological attributes for our lead candidate:

Suppression of B-cell activation induced by CD154-CD40 engagement

No direct activation of B cells

High affinity antagonist of CD40 (e.g., $K_d$ is about $10^{-16}$M or lower, about $10^{-10}$ M to about $10^{-9}$M, or as described herein)

Through a novel immunization approach and an extensive in vitro screening approach, we have identified an anti-CD40 antibody that meets these criteria and represents a non-depleting/non-activating antagonist antibody to human CD40.

In vitro and in vivo studies have confirmed that the humanized form retains excellent properties.

As described in the previous section, the 2C10 mAb was humanized by CDR grafting into a human heavy and light chain frameworks. To maintain the properties of the original 2C10 mAb, the humanized 2C10 constructs were screened by Biacore for affinity 10 human CD40. All three top humanized 2C10 antibodies exhibited only slight reduction in affinity by approximately two-fold, relative to the parent 2C10 mAb (Table 5). Most importantly they all maintained the exceptional slow off rate of the parent 2C10 mAb. Among these antibodies, Clone 2.189.2 which exhibited the highest affinity at 390 pM; was selected as the lead humanized mAb (h2C10).

h2C10 between human CD40 and CD40 from those of nonhuman primate species used in preclinical evaluations. As shown in FIG. 16, h2C10 has comparable affinity for CD40 across these primate species.

In Vivo Characterization of Primate Chimeric and Humanized 2C10

The in vivo pharmacodynamics, pharmacokinetics and exploratory safety assessments of 2C10 were conducted in rhesus monkeys using the primate chimeric construct of 2C10 and the clinical candidate humanized h2C10 antibody. After selection of the lead humanized version of 2C10 (mAb 2.189.2: h2C10) based on in vitro binding kinetics, we advanced h2C10 into a PK/PD study in rhesus monkeys to characterize its additional properties. The data generated in these studies, which cover a broad range of critical experimental endpoints, clearly establish the excellent properties of h2C10.

Studies have been completed in rhesus monkeys examining PD, PK, and safety endpoints. Critical elements of the study designs including key endpoints and objectives are summarized in Table 6 (Pharmacodynamic (PD), Pharmacokinetic (PK) and Safety Studies of 2C10 in Rhesus Monkeys). The key outcomes and relevant comparative assessments on the key experimental endpoints included:

Effect on B and T lymphocyte number in blood

Effect on humoral immune response to the T cell-dependent antigen Keyhole Limpet Hemocyanin (KLH)

CD40 receptor occupancy on blood B cells (PD)

Pharmacokinetics (PK)

TABLE 5

CD40 Receptor Binding Kinetics of Humanized Versions of 2C10

| mAb | $K_D$ (M) | $K_{on}$ (1/Ms) | $K_{off}$ (1/s) | Rmax | Full X^2 | Full R^2 |
|---|---|---|---|---|---|---|
| 2C10 | 2.22E−10 | 1.48E+05 | 6.01E−05 | 0.3124 | 0.284838 | 0.993451 |
| 2.189.1 | 5.11E−10 | 1.98E+05 | 1.85E−04 | 0.3917 | 0.490659 | 0.991111 |
| 2.189.2 | 3.90E−10 | 1.79E+05 | 1.28E−04 | 0.3946 | 0.401784 | 0.991697 |
| 2.191.1 | 5.61E−10 | 1.84E+05 | 1.88E−04 | 0.3924 | 0.402934 | 0.992955 |

Comparing the binding kinetics of humanized 2C10 to competitors, the overall affinity of h2C10 remains substantially better than the competitors that have affinities in the nanomolar range. We also compared binding affinity of Immunogenicity as assessed by formation of anti-drug antibodies (ADA)

Exploratory toxicology include CBC, serum chemistry and complete necropsy

TABLE 6

PD, PK and Safety Studies of 2C10 in Rhesus Monkeys

| Expt. # | Key Objective(s) | Test Versions | Group Size | Test Doses/ Regimen | Follow-Up Period | Key Endpoints |
|---|---|---|---|---|---|---|
| 1 | Compare IgG1 and IgG4 forms, and Competitor 3A8 | Primate chimeric 2C10 | 3 | Two Doses; 50 mk/kg, IV on Days 0 and 7; Saline-Control | 56 Days | CBC Lymphocyte Subsets Primary TDAR (anti-KLH) |
| 2 | Dose-Response Evaluation | Primate chimeric 2C10 IgG4 | 3 | One Dose; 5, 10, 25, 50 mg/kg, IV; Irrelevant IgG Control | 56 Days | CBC Lymphocyte Subsets Detailed B Cell Subsets TDAR (primary and recall response to KLH) |
| 3 | Safety Assessment/ Exploratory Toxicology | Primate chimeric 2C10 IgG4 | 2 | Two Doses; 25 mg/kg, IV on Day 0 and 14; | 14 Days after second dose (28 | CBC Serum Chemistry Lymphocyte Subsets Necropsy Gross & |

TABLE 6-continued

PD, PK and Safety Studies of 2C10 in Rhesus Monkeys

| Expt. # | Key Objective(s) | Test Versions | Group Size | Test Doses/ Regimen | Follow-Up Period | Key Endpoints |
|---|---|---|---|---|---|---|
| 4 | PK, PD, Safety | Humanized 2C10 IgG4 | 3 | Historical Control On Dose; 10, 25 mg/kg, IV; Saline Control | Days in Total) 28 Days | Microscopic Pathology Receptor Occupancy CBC Serum Chemistry Lymphocyte Subsets Primary TDAR anti-KLH)PK ADA |

The study results are summarized in the following section, h2C10 may be used for treatment of conditions in which selective blockade of CD40 receptor activation in the absence of B cell depletion is expected to provide therapeutic benefit.

Effects on T Cell-Mediated Immunity

To prove in vivo that h2C10 blocks T-cell dependent antibody responses (TDAR) in vivo, monkeys were immunized with KLH 6 hours after the administration of h2C10. Antibody titers against KLH were measured weekly thereafter.

Doses of 10 and 25 mg/kg h2C10 were given to monkeys followed by a KLH challenge. Both IgG and IgM anti-KLH titers were determined weekly out to Day 28 after treatment. FIG. 17 shows that the humanized version of 2C10 achieved complete inhibition of the KLH antibody response at the highest test dose, and in most cases at the 10 mg/kg dose level. Both IgM and IgG responses were prevented.

As goals in the development of an antagonist CD40 antibody included minimizing the depletion of targeted. CD40+ cells, we analysed effects on lymphocyte subpopulations, especially the effect on B cells.

The treatment of monkeys with 10 or 25 mg kg of the humanized form of 2C10 (h2C10) also had no appreciable depleting effect on B cells even though the CD40 target is fully saturated by the antibody at these concentrations (see subsequent Section Receptor Occupancy).

Despite saturation of 2C10 binding sites on B cells lasting until the last day measured (Day 28), all monkeys that received either dose of h2C10 maintained normal B and T lymphocyte subsets (FIG. 18). These results demonstrate that injection with a dose as low as 10 mg/kg 2C10 can persistently bind CD40, its therapeutic target on B cells (and presumably monocytes and other antigen presenting cells) without causing undesired depletion of B cells in monkeys.

The demonstration that 2C10 does not deplete B cells suggests a clear advantage over competitors in addition to 3A8 and Chi220.

Pharmacodynamics

CD40 Receptor Occupancy

CD40 target, engagement and occupancy by the primate chimeric and humanized versions of 2C10 was determined by measuring the available binding sites for 2C10 to CD40 on CD20+ B cells by flow cytometry using fluorescently labeled 2C10 and a labeled, non-competing anti-CD40 antibody. Blood samples were collected on multiple days from control monkeys and monkeys treated with either primate chimeric IgG4 or humanized 2C10 and analyzed by FACS. The degree of target engagement (% receptor occupancy) was calculated directly from the mean fluorescent intensity recordings.

Humanized 2C10 antibodies were administered intravenously at single doses of 10 and 25 mg/kg. Surface CD40 on B cells was completely saturated by Day 3, and the effect persisted until the last day measured (Day 28) in all monkeys that received either dose of h2C10. Representative data from the flow cytometry analysts of blood collected from monkeys 28 days alter treatment with humanized 2C10 is shown FIG. 19.

These results demonstrate that a single injection of h2C10 at a dose as low as 10 mg/kg can fully saturate CD40 receptors on B cells for at least 28 days.

Pharmacokinetics and Anti-Drug Antibody Response

To establish a clear link between the pharmacodynamic effects of 2C10 based on CD40 receptor occupancy and the pharmacokinetics of 2C10 plasma concentrations of the 2C10 were measured in plasma from the same blood samples in which receptor occupancy had been determined. The plasma concentration analysis also enabled characterization of the pharmacokinetic profile of 2C10, most importantly its persistence in plasma as determined by its half-life. This determination provides guidance for the frequency of dosing that will be needed to maintain effective therapeutic concentrations.

The mean serum concentrations determined in monkeys treated with either 10 or 25 mg/kg humanized 2C10 are plotted in FIG. 20. These data demonstrate that the animals were exposed to 2C10 for the entire duration of the study, and that humanized 2C10 has a half-life in monkeys of approximately 15 days (ranging from 9-20 days). This half-life is in the range of that expected for a therapeutic antibody in primates, and should support a relatively infrequent dosing schedule in clinical investigations (e.g., no more than once every two weeks). Further modeling of the complete dataset will enable a robust estimate of the dose and frequency required to sustain effective antibody concentrations in initial clinical studies of h2C10.

Another assessment of humanized 2C10 was the potential development of antibodies against h2C10 (ADA). This can occur when biologies of epitopes from one species is administered to a different species (eg. Humanized mAb to primates) resulting in rapid clearance of the drug from plasma. In this study there was no evidence from the time course profile that antibodies against h2C10 were generated, as no animal exhibited measurable anti-2C10 titers during the study.

Preliminary Safety Evaluation

The experiments described in this section were conducted to determine potential adverse consequences of h2C10 on the immune system and for off-target effects. For biological therapies, these assessments are among the most critical for evaluating safety prior to human exposure to the drug, and developing risk mitigation plans for clinical testing. The absence of any unexpected or undesired outcomes on immune function or pathology in monkeys is viewed favorably for the overall safety assessment of h2C10. In addition, routine tests for alterations in hematological parameters, including platelet counts, and serum chemistry parameters in monkeys treated with 2C10 were conducted on several days post-dosing, and were unaffected by treatment with chimeric and humanized 2C10. Two animals that were treated twice with 25 mg/kg primate chimeric 2C10 were evaluated for gross and microscopic evidence of treatment related pathology; no treatment-related pathological changes were observed. In addition, to rule out thromoboemolic complications, all tissues were examined by special stains for fibrin deposition. No evidence of subclinical clotting abnormalities was detected. Importantly, relatively high doses were tested in the studies that appreciably exceeded the doses required to full occupy CD40 receptors and therefore approach the dose levels that will be tested in pivotal toxicology studies conducted during the IND-enabling phase. These preliminary safety evaluations show absence of any safety concerns for h2C10.

These combined data demonstrate in a relevant primate model that 2C10 has the desirable pharmacodynamic, pharmacokinetic and safety attributes for a monoclonal antibody intended to treat patients, where specific inhibition of CD40 actuation is desired without causing unwanted activation or depletion of CD40+ targets cells and without evidence of off-target toxicity.

While specific aspects of the invention have been described and illustrated, such aspects should be considered illustrative of the invention only and not as limiting the invention as construed in accordance with the accompanying claims. All publications and patent applications if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. A humanized anti-CD40 antibody or antigen-binding fragment thereof comprising a heavy chain variable region comprising an amino acid sequence with at least 80% sequence identity to the amino acid sequence set forth in any one of SEQ ID NOs: 19, 20, 21, 24, 25, and 26 and a light chain variable region comprising an amino acid sequence with at least 80% sequence identity to the amino acid sequence set forth in any one of SEQ ID NOs: 22, 23, 27, 28 and 29, wherein the heavy chain variable region comprises a CDR1, CDR2, and CDR3 with the amino acid sequences set forth in SEQ ID NOs: 13, 14, and 15, respectively, and wherein the light chain variable region comprises a CDR1, CDR2, and CDR3 with the amino acid sequences set forth in SEQ ID NOs: 16, 17, and 18, respectively.

2. The antibody or antigen-binding fragment thereof of claim 1, wherein the amino acid sequence of the heavy chain variable region has at least 90% sequence identity to the amino acid sequence set forth in any one of SEQ ID NOs: 19, 20, 21, 24, 25, and 26, and the amino acid sequence of the light chain variable region has at least 90% sequence identity to the amino acid sequence set forth in any one of SEQ ID NOs: 22, 23, 27, 28 and 29.

3. The antibody or antigen-binding fragment thereof of claim 2, wherein the amino acid sequence of the heavy chain variable region comprising an amino acid sequence has at least 95% identity to the amino acid sequences set forth in any one of SEQ ID NOs: 19, 20, 21, 24, 25, and 26, and the amino acid sequence of the light chain variable region has at least 95% sequence identity to the amino acid sequences set forth in any one of SEQ ID NOs: 22, 23, 27, 28 and 29.

4. The antibody or antigen-binding fragment thereof of claim 3, wherein the amino acid sequence of the heavy chain variable region comprises the amino acid sequence set forth in any one of SEQ ID NOs: 19, 20, 21, 24, 25, and 26, and the amino acid sequence of the light chain variable region comprises the amino acid sequence set forth in any one of SEQ ID NOs: 22, 23, 27, 28 and 29, wherein the antibody or antigen-binding fragment thereof does not comprise the heavy chain variable region comprising the amino acid sequence set forth in SEQ ID NO: 21 and the light chain variable region comprising the amino acid sequence set forth in SEQ ID NO: 23.

5. The antibody or antigen-binding fragment thereof of claim 1, wherein:
   a) the dissociation constant (KD) of the antibody or antigen-binding fragment thereof is less than about $1 \times 10^{-9}$ M;
   b) the antibody or antigen-binding fragment thereof is selected from the group consisting of: (a) a whole immunoglobulin molecule; (b) an scFv; (c) a Fab fragment; (d) an F(ab')$_2$; and (e) a disulfide linked Fv;
   c) the antibody or antigen-binding fragment thereof comprises at least one constant domain selected from the group consisting of: a) an IgG constant domain; and (b) an IgA constant domain;
   d) the antibody or antigen-binding fragment thereof comprises at least one human constant domain;
   e) the antibody or antigen-binding fragment thereof binds to CD40 extracellular domain;
   f) the CD40 is human or rhesus CD40;
   g) the antibody or antigen-binding fragment thereof blocks B lymphocyte activation by CD154-expressing Jurkat cells in vitro; and/or
   h) the antibody or antigen-binding fragment thereof inhibits B lymphocyte CD23, CD80, or CD86 expression.

6. A composition comprising the antibody or antigen-binding fragment thereof of claim 1 and a pharmaceutically acceptable carrier.

7. A method of suppressing the immune system in a subject comprising administering to the subject an effective amount of the antibody or antigen-binding fragment thereof of claim 1.

8. A method of treating transplant rejection or increasing the duration of time before transplant rejection occurs in a subject in need thereof comprising administering to the subject an effective amount of the antibody or antigen-binding fragment of claim 1.

9. The method of claim 8, wherein the subject has received, or is in need of, an organ or tissue transplantation.

10. The method of claim 9, wherein:
 a) the organ is selected from the group consisting of heart, kidney, lung, liver, pancreas, intestine, and thymus, or a portion thereof; or
 b) the tissue is bone, tendon, cornea, skin, heart valve, vein, or bone marrow.

11. The method of claim 8, wherein the antibody or antigen-binding fragment thereof is administered prior to the transplantation.

12. The method of claim 8, wherein the antibody or antigen-binding fragment thereof is administered for at least one month following the transplantation.

13. The method of claim 12, wherein the antibody or antigen-binding fragment thereof is administered for at least six months following the transplantation.

14. A method of treating graft-versus-host disease in a subject in need thereof comprising administering to the subject a therapeutically effective amount of the antibody or antigen-binding fragment thereof of claim 1.

15. A method of blocking the ability of CD40 to interact with CD154 in a subject comprising administering to the subject an effective amount of the antibody or antigen-binding fragment thereof of claim 1.

16. The method of claim 15, wherein the subject has an autoimmune disorder associated with or caused by the presence of an autoantibody.

17. The method of claim 15, wherein the subject has a disorder selected from the group consisting of systemic lupus erythematosus (SLE), CREST syndrome (calcinosis, Raynaud's syndrome, esophageal dysmotility, sclerodactyl, and telangiectasia), opsoclonus, inflammatory myopathy, systemic scleroderma, primary biliary cirrhosis, celiac disease, dermatitis herpetiformis, Miller-Fisher Syndrome, acute motor axonal neuropathy (AMAN), multifocal motor neuropathy with conduction block, autoimmune hepatitis, antiphospholipid syndrome, Wegener's granulomatosis, microscopic polyangiitis, Churg-Strauss syndrome, rheumatoid arthritis, chronic autoimmune hepatitis, scleromyositis, myasthenia gravis, Lambert-Eaton myasthenic syndrome, Hashimoto's thyroiditis, Graves' disease, Paraneoplastic cerebellar degeneration, Stiff person syndrome, limbic encephalitis, Isaacs Syndrome, Sydenham's chorea, pediatric autoimmune neuropsychiatric disease associated with *Streptococcus* (PANDAS), encephalitis, diabetes mellitus type 1, neuromyelitis optica, pernicious anemia, Addison's disease, psoriasis, inflammatory bowel disease, psoriatic arthritis, Sjögren's yndrome, lupus erythematosus, multiple sclerosis, reactive arthritis, polymyositis, dermatomyositis, multiple endocrine failure, Schmidt's syndrome, autoimmune uveitis, adrenalitis, thyroiditis, auto immune thyroid disease, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, alopecia arcata, pemphigoid, scleroderma, progressive systemic sclerosis, adult-onset diabetes mellitus, male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, endocarditis, endomyocardial fibrosis, endophthalmitis, erythema elevatum et diutinum, erythroblastosis fetalis, eosinophilic fasciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and non Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, mumps, Evan's syndrome, and autoimmune gonadal failure.

18. The method of claim 7, wherein the subject is a human.

19. The method of claim 7, wherein the antibody or antigen-binding fragment thereof is administered via parenteral, intravenous, subcutaneous, intramuscular, transdermal, oral, topical, intrathecal, or local routes.

20. The method of claim 7, wherein the method further comprises administering an immunosuppressant within six months of administering the antibody or antigen-binding fragment thereof.

21. The method of claim 20, wherein the immunosuppressant is selected from the group consisting of a calcineurin inhibitor selected from the group consisting, of cyclosporin A and cyclosporine G, tacrolimus, an mTor inhibitor, fingolimod, myriocin, alemtuzumab, rituximab, an anti-CD4 monoclonal antibody, an anti-LEA-1 monoclonal antibody, an anti-LEA-3 monoclonal antibody, an anti-CD45 antibody, an anti-CD19 antibody, monabatacept, belatacept, indolyl-ASC; azathioprine, lymphocyte immune globulin and anti thymocyte globulin, mycophenolate mofetil, mycophenolate sodium, daclizumab, basiliximab, cyclophosphamide, prednisone, prednisolone, leflunomide, FK778, FK779, 15-deoxyspergualin, busulfan, fludarabine, methotrexate, 6-mercaptopurine, 15-deoxyspergualin, LF15-0195, busulfan, fludarabine, methotrexate, 6-mercaptopurine, 15-deoxyspergualin, LF15-0195, bredinin, brequinar, and muromonab-CD3.

22. The method of claim 21, wherein the calcineurin inhibitor is cyclosporin A or cyclosporine G.

23. The method of claim 21, wherein the anti-CD45 antibody is an anti-CD45RB antibody.

24. The method of claim 21, wherein the immunosuppressant is belatacept.

25. The method of claim 21, wherein the antibody or antigen-binding fragment thereof and the immunosuppressant are administered within one month of each other.

26. The method of claim 25, wherein the antibody or antigen-binding fragment thereof and the immunosuppressant are administered within one week of each other.

\* \* \* \* \*